US012559770B2

(12) United States Patent
De Villiers-Zur Hausen et al.

(10) Patent No.: US 12,559,770 B2
(45) Date of Patent: Feb. 24, 2026

(54) MSBI SEQUENCES AS AN EARLY MARKER FOR THE FUTURE DEVELOPMENT OF CANCER AND DISEASES OF THE CNS AND AS A TARGET FOR THE TREATMENT AND PREVENTION OF THESE DISEASES

(71) Applicant: DEUTSCHES KREBSFORSCHUNGSZENTRUM STIFTUNG DES ÖFFENTLICHEN, Heidelberg (DE)

(72) Inventors: Ethel-Michele De Villiers-Zur Hausen, Wald-Michelbach (DE); Harald Zur Hausen, Wald-Michelbach (DE); Karin Gunst, Hirschberg (DE); Corinna Whitley, Viernheim (DE); Iranzu Lamberto-Pérez, Navarra (ES)

(73) Assignee: DEUTSCHES KREBSFORSCHUNGSZENTRUM STIFTUNG DES ÖFFENTLICHEN, RECHTS Heidelberg (DE)

( * ) Notice: Subject to any disclaimer, the term of this patent is extended or adjusted under 35 U.S.C. 154(b) by 1134 days.

(21) Appl. No.: 17/407,483

(22) Filed: Aug. 20, 2021

(65) Prior Publication Data

US 2022/0112518 A1     Apr. 14, 2022

Related U.S. Application Data

(60) Division of application No. 16/362,941, filed on Mar. 25, 2019, now abandoned, which is a continuation of application No. 15/402,579, filed on Jan. 10, 2017, now abandoned, which is a continuation-in-part of application No. PCT/EP2015/001399, filed on Jul. 9, 2015.

(30) Foreign Application Priority Data

Jul. 10, 2014     (EP) .................................... 14176624

(51) Int. Cl.
*C12N 15/86* (2006.01)
*C07K 16/28* (2006.01)
*C12N 5/0783* (2010.01)
*C12N 15/85* (2006.01)

(52) U.S. Cl.
CPC .............. *C12N 15/86* (2013.01); *C07K 16/28* (2013.01); *C12N 5/0636* (2013.01); *C12N 2015/8518* (2013.01)

(58) Field of Classification Search
None
See application file for complete search history.

(56) References Cited

U.S. PATENT DOCUMENTS 10,287,335 B2     5/2019   Zur Hausen et al.
2017/0198018 A1   7/2017   De Villiers-Zur Hausen et al.

OTHER PUBLICATIONS

Kriesel, J. D., Hobbs, M. R., Jones, B. B., Milash, B., Nagra, R. M., & Fischer, K. F. (2012). Deep sequencing for the detection of virus-like sequences in the brains of patients with multiple sclerosis: detection of GBV-C in human brain. PloS one, 7(3), e31886 (Year: 2012).*
5192Ap-5192A-a_00744c Viral Genomic Survey of Stool from South East Asian Children with Acute Flaccid Paralysis human gut metagenome genomic, genomic survey sequence, retrieved from EBI accession No. EM_GSS:FI584419 (Feb. 23, 2009).
Anderson, et al., Gene Discovery in the *Acanthamoeba castellanii* Genome, Protist (Aug. 2005) 156(2):203-214.
CM2-BT0368-171299-056-b03 BT0368 *Homo sapiens* cDNA, RNA sequence, retrieved from EBI accession No. EM_EST:BE068140 (Jun. 20, 2000).
EDCCM68TF A. castellanii, 6-8 kb library from total genomic DNA *Acanthamoeba castellanii* genomic clone EDCCM68, genomic survey sequence, retrieved from EBI accession No. EM_GSS:CW934145, Feb. 26, 2005.
Manuelidis, Nuclease resistant circular DNAs copurify with infectivity in scrapie and CJD, Journal of Neurovirology (Dec. 2010) 17(2):131-145.
Neto, et al. Shotgun Sequencing of the Human Transcriptome with ORF Expressed Sequence Tags, PNAS (Mar. 2000) 97(7):3491-3496.
Palenik, et al., Coastal Synechococcus Metagenome Reveals Major Roles for Horizontal Gene Transfer and Plasmids in Population Diversity, Environmental Microbiology (Feb. 2009) 11(2):349-359.
Database Accession No. CP000715 (Jun. 6, 2007) *Psychrobacter* sp. PRwf-1 plasmid pRWF 102, complete sequence retrieved from EBI accession No. EM_STD:CP000715.
QV0-CT0181-041199-048-908 CT0181 *Homo sapiens* cDNA, mRNA sequence. retrieved from EBI accession No. EM EST:CK327030 (Dec. 17, 2004).
Database Accession No. JX416184 (Jul. 31, 2013) Tomato leaf curl Laos virus-[EastTimor:Oecusse:2000] isolate Q1584 segment DNA-A C1 protein gene, partial cds; and C4 protein gene, complete cds.: XP002738154, retrieved from EBI accession No. EM_STD:JX416184.
TSE-associated circular DNA isolate Sphinx 1.76, complete sequence, retrieved from EBI accession No. EM_STD:HQ444404 (Dec. 10, 2010).

(Continued)

*Primary Examiner* — Anne M. Gussow
(74) *Attorney, Agent, or Firm* — Duane Morris LLP; Thomas J. Kowalski

(57) ABSTRACT

The application relates to MSBI (Multiple Sclerosis Brain Isolate) nucleotide sequences as well as probes and primers comprising part of said nucleotide sequences and antibodies against polypeptides encoded by said nucleotide sequences. These compounds are useful as early markers for the future development of cancer and diseases of the CNS (Multiple sclerosis MS, Prion-linked diseases, amyotrophic lateral sclerosis, transmissible spongiforme encephalitis, Parkinson's disease, Alzheimer disease) and should represent targets for treatment and prevention.

20 Claims, 16 Drawing Sheets

Specification includes a Sequence Listing.

(56)    References Cited

OTHER PUBLICATIONS

Uncultured bacterium plasmid clone S6GIO-17 genomic sequence, retrieved from EBI accession No. EM_STD:JN541288 (Sep. 28, 2011).

Victoria, et al., Metagenomic Analyses of Viruses in Stool Samples from Children with Acute Flaccid Paralysis, Journal of Virology (May 2009) 83(9):4642-4651.

XDU016D14.F XDU Aplanochytrium kerguelense genomic 5', genomic survey sequence, retrieved from EBI accession No. EM_GSS:JY165485 Database accession No. JY165485 (Nov. 21, 2012).

International Search Report and Written Opinion dated Jan. 18, 2016, issued in International Application No. PCT/EP2015/001399.

Laura Manuelidis, Nuclease Resistant Circular DNAs Copurity with Infectivity in Scrapie and CJD, J. Neurovirology (2011) vol. 17, p. 131-146.

Longkumer et al., Acinetobacter phage genome is similar to Sphinx 2.36, the circular DNA copurified with TSE infected particles (Jul. 19, 2013) Scientific Reports 13:2240 I DOI: 10. 1038/srep02240, 9 pages.

* cited by examiner

*MSBI1.176  (1766bp)*                    *(MSBI = Multiple Sclerosis Brain Isolate)*

*(ms36.NnXn.1800.6)*

```
AAGCTTGCTTAGTCAAAAAAGTTTGAGCAAAGCGAAAACATAGGGCAATTTTCATGAAGAAATTGGGCTTTTAAAGTTTTTAA
ATGCTTTTAAATGCTTTTAGACATGCTAAGAAGCCCACACAGCAAGGCATACAGAGGACATTCTCCTACGTTTACCGATCAAT
ACCCCTACGTTTACCGATCAATACCCCTACGTTTACCGATCAATACCCCTACGTTTACGTTGCGTATAACTACAAAGAATACT
AGTGTAGTAATAACTTCAAAAGAATAATTGTAGGTTATGAGCGATTTAATAGTAAAAGATAACGCCCTAATGAATGCTAGTTA
TAACTTAGCTTTGGTTGAACAGAGGTTAATTCTATTAGCAATCATAGAAGCGAGAGAAACAGGCAAAGGGATTAATGCCAATG
ATCCTTTAACAGTTCATGCAAGTAGCTATATCAATCAATTAACGTAGAAAGGCATACGGCATATCAAGCCCTCAAAGATGCT
TGTAAAGACTTGTTTGCCCGTCAATTCAGTTACCAAGAAAAGCGAGAACGAGGACGAATTAATATTACAAGTCGATGGGTTTC
GCAAATTGGCTATATGGACGATACAGCAACCGTTGAGATTATTTTTGCCCCTGCGGTTGTTCCTCTGATTACACGGCTAGAGG
AACAGTTCACCCAGTACGATATTGAGCAAATTAGCGGTTTATCGAGTGCATATGCTGTTCGTATGTACGAACTGCTGATTTGT
TGGCGTAGCACAGGCAAAACACCAATTATTGAGCTAGACGAGTTTAGAAAGCGAATAGGTGTTTAGATACTGAATACACTAG
AACAGATAATTTAAAGATGCGAGTTATTGAATTAGCCCTAAAACAAATCAACGAACATACAGACATCACAGCAAGCTATGAAC
AACACAAAAAAGGGCGAGTGATTACAGGATTCTCATTCAAGTTTAAGCACAAGAAACAAAACAGCGATAAAACGCCAAAAAAT
AGCGATTCTAGCCCACGTATCGTAAAACATAGTCAAATCCCTACCAACATTGTAAAACAGCCTGAAAACGCCAAAATGAGCGA
TTTAGAACATAGAGCGAGCCGTGTTACAGGGGAAATAATGCGAAATCGTCTGTCAGATCGGTTTAAACAAGGCGATGAATCAG
CAATCGACATGATGAAACGTATTCAAAGTGAAATAATAACCGATGCAATAGCCAGACCAGTCGGGAAAGCAAACTGGAGGAGTTT
GGCGTGGTTTTTTAGTCATGACGATTTCCCGAAGGGCGCACTTAGCCCATTGAGCAAAAATCTTCGATTTTTTCAATGGAAGTCC
GTGGGGGGTAAACCCCTCAACCCCAAAAGCAAAAACACTGTAATCAGGGAAAAAACATTTTTGATTTTGATCCTTGTTTGTCAC
TCGTAGACACTCGTTTTGTTTTGCTCTTTCTAGAATTCACAAAAAAGATATTAGCGAGTGTCTACGAGCGACTCAATGAAAGT
TCGATTATTCCCCCTCTGGAAAACCGCTTTTAAAAATATTGGCTGCTAGATGGTTTTTACTATAGTGAGGTTTTGCTTTTAAA
AAAACACGAGCAAAGCGAGTTCATAGTTGCTTTTGCTTGTTTTCGGGTCTTAGGGGAAATCCCCTAACAAGTCCTCGAATATC
AAAATGTGGCTACATTTTGTATATACGGGTAGGCTTGCTTATTTGATTTTTTTTCTTCTAAACCTTTGACTTCTTCCCCATTG
TTTGCAGAAATTGCCCCTCGACT
```

*Repeat ~ 3x 22nt + 17nt*

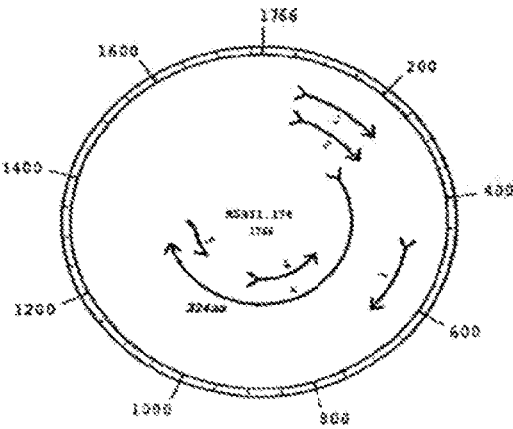

*98% nucleotide similarity to TSE-associated circular DNA isolate Sphinx 1.76*

*ORF:  324aa ~ 97% similarity to replication protein of Sphinx 1.76*

FIG. 1A

*Blastn – Geall:*

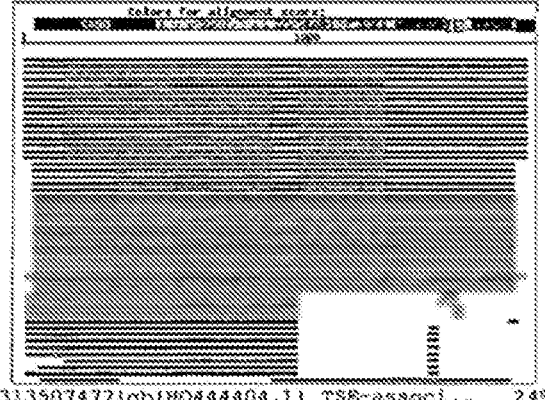

```
>>>nrnuc:GI_313507477   GI|313507477|gb|HQ444404.1| TSE-associ..   2491   0.0
>>>nrnuc:GI_347602273   GI|347602273|gb|JN941306.1| Uncultured...    986   0.0

>>>>nrnuc:GI_313507477 GI|313507477|gb|HQ444404.1| TSE-associated circular DNA isolate
Sphinx 1.76, complete sequence. 0/0
Length=1758

Score = 2491 bits (2762),  Expect = 0.0
  Identities = 1419/1439 (98%)  Gaps = 5/1439 (0%)
  Strand=Plus/Plus Query  1     AAGCTTGCTTAGTCAAAAAAGTTTGAGCAAAGCGAAAACATAGGGCAATTTTCATGAAGA  60
             ||||||||||||||||||||||||||||||||||||||||||||||||||||||||||||
Sbjct  325   AAGCTTGCTTAGTCAAAAAAGTTTGAGCAAAGCGAAAACATAGGGCAATTTTCATGAAGA  384

Query  61    AATTGGGCTTTTAAAGTTTTTAAATGCTTTTAAATGCTTTTAGACATGCTAAGAAGCCCA  120
             ||||||||||||||||||||||||| ||||||||||||||||||||||||||||||||||
Sbjct  385   AATTGGGCTTTTAAAGTTTTTAAATG-TTTTAAATGCTTTTAGACATGCTAAGAAGCCCA  443

Query  121   CACAGCAAGGCATACAGAGGACATTCTCCTACGTTTACCGATCAATACCCCTACGTTTAC  180
             ||||||||||||||||||||||||||||||||||||||||||||||||||||   |||||
Sbjct  444   CACAGCAAGGCATACAGAGGACATTCTCCTACGTTTACCGATCAATACCCC---CGTTTAC  501

Query  181   CGATCAATACCCCTACGTTTACCGATCAATACCCCTACGTTTACCTTGCGTATAACTACA  240
             ||||||||||||||||||||||||||||||||||||||||||||||||||||||||||||
Sbjct  502   CGATCAATACCCCTACGTTTACCGATCAATACCCCTACGTTTACCTTGCGTATAACTACA  561

Query  241   AAGAATACTAGTCTAGTAATAACTTCAAAAGAATAATTGTAGGTTATGAGCGATTAATA  300
             |||||||||||||||||| ||||||||||||||||||||||||||||||||||||||||
Sbjct  562   AAGAATACTAGTGTAGTA-TAACTTCAAAAGAATAATTGTAGGTTATGAGCGATTAATA  630

Query  301   GTAAAAGATAACGCCCTAATGAATGCTAGTTATAACTTAGCTTTGGTTGAACAGAGGTTA  360
             ||||||||||||||||||||||||||||||||||||||||||||||||||||||||||||
Sbjct  621   GTAAAAGATAACGCCCTAATGAATGCTAGTTATAACTTAGCTTTGGTTGAACAGAGGTTA  680

Query  361   ATTCTATTAGCAATCATAGAAGCGAGAGAAACAGGCAAAGGGATTAATGCCAATGATCCT  420
             ||||||||||||||||||||||||||||||||||||||||||||||||||||||||||||
Sbjct  681   ATTCTATTAGCAATCATAGAAGCGAGAGAAACAGGCAAAGGGATTAATGCCAATGATCCT  740

Query  421   TTAACAGTTCATGCAAGTAGCTATATCAATCAATTTAACGTAGAAAGGCATACGGCATAT  480
              | || |||||||||| ||||||||||||||||||||||||| ||||||||||||||||
Sbjct  741   CTTACGGTTCATGCAGGTAGCTATATCAATCAATTTAACGTACAAAGGCATACGGCATAT  800

Query  481   CAAGCCCTCAAAGATGCTTGTAAAGACTTGTTTGCCCGTCAATTCAGTTACCAAGAAAAG  540
             ||||||||||||||||||||||||||| ||||||||||||||||||||||||||||||||
Sbjct  801   CAAGCCCTCAAAGATGCTTGTAAAGACTTGTTTGCCCGTCAATTCAGTTACCAAGAAAAG  860

Query  541   CGAGAACGAGGACGAATTAATATTACAAGTCGATGGGTTTCGCAAATTGGCTATATGGAC  600
             ||||||||||||||||||||||||||||||||||||||||||||||||||||||||||||
Sbjct  861   CGAGAACGAGGACGAATTAATATTACAAGTCGATGGGTTTCGCAAATTGGCTATATGGAC  920

Query  601   GATACAGCAACCGTTGAGATTATTTTTGCCCCTGCGGTTGTTCCTCTGATTACACGGCTA  660
             ||||||||||||||||||||||||||||||||||||||||||||||||||||||||||||
Sbjct  921   GATACAGCAACCGTTGAGATTATTTTTGCCCCTGCGGTTGTTCCTCTGATTACACGGCTA  980
```

FIG. 1B

```
Query   661   GAGGAACAGTTCACCCAGTACGATATTGAGCAAATTAGCGGTTTATCGAGTGCATATGCT   720
              |||||||||||||||||||||||||||||||||||||||||||||||||||||||||||
Sbjct   981   GAGGAACAGTTCACCCAGTACGATATTGAGCAAATTAGCGGTTTATCGAGTGCATATGCT  1040

Query   721   GTTCGTATGTACGAACTGCTGATTTGTTGGCGTAGCACAGGCAAAACACCAATTATTGAG   780
              ||||||||||||||||||||||||||||||||||||||||||||||||||||||||||||
Sbjct  1041   GTTCGTATGTACGAACTGCTGATTTGTTGGCGTAGCACAGGCAAAACACCAATTATTGAG  1100

Query   781   CTAGACGAGTTTAGAAAGCGAATAGGTGTTTTAGATACTGAATACACTAGAACAGATAAT   840
              |||||||||||||||||||||||||||||||||||||||||||||||||||||||||||·
Sbjct  1101   CTAGACGAGTTTAGAAAGCGAATAGGTGTTTTAGATACTGAATACACTAGAACAGATAAT  1160

Query   841   TTAAAGATGCGAGTTATTGAATTAGCCCTAAAACAAATCAACGAACATACAGACATCACA   900
              ||||||||| ||||||||||||||||||||||||||||||||||||||| ||||||||||
Sbjct  1161   TTAAAGATGCAAGTTATTGAATTAGCCCTAAAACAAATCAACGAACATACTGACATCACA  1220

Query   901   GCAAGCTATGAACAACACAAAAAAGGGCGAGTGATTACAGGATTCTCATTCAAGTTTAAG   960
              |||||||||||||||||||||||||||||||||| ||||||||||||||||  |||||||
Sbjct  1221   GCAAGCTATGAACAACACAAAAAAGGGCGAGTGATTACCGGATTCTCATTCATGTTTAAG  1280

Query   961   CACAAGAAACAAAACAGCGATAAAACGCCAAAAAATAGCGATTCTAGCCCACGTATCGTA  1020
              ||||||||||||||||||||||||  | || || |||||||||||||||||||||||||
Sbjct  1281   CACAAGAAACAAAACAGCGATAAAACGCCTGATACTAACGCTTCTAGCCCACGTATCGTA  1340

Query  1021   AAACATAGTCAAATCCCTACCAACATTGTAAAACAGCCTGAAAACGCCAAAATGAGCGAT  1080
              ||||||||||||||||||||||||||||||||||||||||||||||||||||||||||||
Sbjct  1341   AAACATAGTCAAATCCCTACCAACATTGTAAAACAGCCTGAAAACGCCAAAATGAGCGAT  1400

Query  1081   TTAGAACATAGAGCGAGCCGTGTTACAGGGGAAATAATGCGAAATCGTCTGTCACATCGG  1140
              ||||||||||||||||||||||||||||||||||||||||||||||||||||||||||||
Sbjct  1401   TTAGAACATAGAGCGAGCCGTGTTACAGGGGAAATAATGCGAAATCGTCTGTCACATCGG  1460

Query  1141   TTTAAACAAGGCGATGAATCAGCAATCGACATGATGAAACGTATTCAAAGTGAAATAATA  1200
              ||||||||||||||||||||||||||||||||||||||||||||||||||||||||||||
Sbjct  1461   TTTAAACAAGGCGATGAATCAGCAATCGACATGATGAAACGTATTCAAAGTGAAATAATA  1520

Query  1201   ACCGATGCAATAGCAGACCAGTGGGAAAGCAAACTGGAGGAGTTTGGCGTGGTTTTTTAG  1260
              ||||||||||||||||||||||||||||||||||||||||||||||||||||||||||||
Sbjct  1521   ACCGATGCAATAGCAGACCAGTGGGAAAGCAAACTGGAGGAGTTTGGCGTGGTTTTTTAG  1580

Query  1261   TCATGACGATTTCCCGAAGGGCGCACTTAGCCATTGAGAAAAATCTTCGATTTTTTCAAT  1320
              ||||||||||||||||||||||||||||||||||||||||||||||||||||||||||||
Sbjct  1581   TCATGACGATTTCCCGAAGGGCGCACTTAGCCATTGAGAAAAATCTTCGATTTTTTCAAT  1640

Query  1321   GGAAGTCCGTGGGGGTAAACCCCTCAACCCCAAAAGCAAAAACACTGTAATCAGGGAAAA  1380
              ||||||||||||||||||||||||||||||||||||||||||||||||||||||||||||
Sbjct  1641   GGAAGTCCGTGGCGGTAAACCCCTCAACCCCAAAAGCAAAAACACTGTAATCAGGGAAAA  1700

Query  1381   AACATTTTTGATTTTGATCCTTGTTTGTCACTCGTAGACACTCGTTTTGTTTTGCTCTT   1439
              |||||||||||||||||||||||||||||| |||||||||||||||||||||||||||||
Sbjct  1701   AACATTTTTGATTTTGATCCTTGTTTG-CACTCGTAGACACTCGTTTTGTTTTGCTCTT   1758
```

```
Score = 587 bits (650),  Expect = 2e-163
Identities = 325/325 (100%),  Gaps = 0/325 (0%)
Strand=Plus/Plus
```

```
Query  1440   TCTAGAATTCACAAAAAAGATATTAGCGAGTGTCTACGAGCGACTCAATGAAAGTTCGAT  1499
              ||||||||||||||||||||||||||||||||||||||||||||||||||||||||||||
Sbjct     1   TCTAGAATTCACAAAAAAGATATTAGCGAGTGTCTACGAGCGACTCAATGAAAGTTCGAT    60

Query  1500   TATTCCCCCTCTGGAAAACCGCTTTTAAAAATATTGGCTGCTAGATGGTTTTTACTATAG  1559
              ||||||||||||||||||||||||||||||||||||||||||||||||||||||||||||
Sbjct    61   TATTCCCCCTCTGGAAAACCGCTTTTAAAAATATTGGCTGCTAGATGGTTTTTACTATAG   120

Query  1560   TGAGGTTTTGCTTTTaaaaaaaCACGAGCAAAGCGAGTTCATAGTTGCTTTTGCTTGTTT  1619
              |||||||||||||||| |||||||||||||||||||||||||||||||||||||||||||
Sbjct   121   TGAGGTTTTGCTTTTAAAAAAACACGAGCAAAGCGAGTTCATAGTTGCTTTTGCTTGTTT   180

Query  1620   TCGGGTCTTAGGGGAAATCCCCTAACAAGTCCTCGAATATCAAAATGTGGCTACATTTTG  1679
              ||||||||||||||||||||||||||||||||||||||||||||||||||||||||||||
Sbjct   181   TCGGGTCTTAGGGGAAATCCCCTAACAAGTCCTCGAATATCAAAATGTGGCTACATTTTG   240

Query  1680   TATATACGGGTAGGCTTGCTTATTTGAtttttttttCTTCTAAACCTTTGACTTCTTCCCC  1739
              ||||||||||||||||||||||||||| |||||||||||||||||||||||||||||||||
Sbjct   241   TATATACGGGTAGGCTTGCTTATTTGATTTTTTTTTCTTCTAAACCTTTGACTTCTTCCCC   300

Query  1740   ATTGTTTGCAGAAATTGCCCCTCGA   1764
```

```
                    ||||||||||||||||||||||||||||
Sbjct  301    ATTGTTTGCAGAAATTGCCCCTCGA  325
```

*BlastP -Uniprot:*

*ORF 324aa:*

```
>>>sptrembl:E5LG72_9XXXX  E5lg72 SubName: Full=Replicase 3-li...    658    0.0
>>>sptrembl:N9LWE7_9GAMM  N9lwe7 SubName: Full=Uncharacterize...    569    5e-160

>>>>sptrembl:E5LG72_9XXXX E5lg72 SubName: Full=Replicase 3-like protein;, 5/2013
Length=324
  Score = 658 bits (1698),  Expect = 0.0, Method: Compositional matrix adjust.
  Identities = 316/324 (97%), Positives = 319/324 (98%), Gaps = 0/324 (0%)

Query  1    MSDLIVKDNALMNASTNLALVEQRLILLAIIEARETGKGINANDPLTVRASSYINQFNVE  60
            MSDLIVKDNALMNASYNLALVEQRLILLAIIEARETGKGINANDPLTVRA SYINQFNV+
Sbjct  1    MSDLIVKDNALMNASYNLALVEQRLILLAIIEARETGKGINANDPLTVRAGSYINQFNVQ  60

Query  61   RHTAYQALKDACKDLFARQFSYQEKRERGRINITSRWVSQIGYMDDTATVEIIFAPAVVP  120
            RHTAYQALKDACKDLFARQFSYQEKRERGRINITSRWVSQIGYMDDTATVEIIFAPAVVP
Sbjct  61   RHTAYQALKDACKDLFARQFSYQEKRERGRINITSRWVSQIGYMDDTATVEIIFAPAVVP  120

Query  121  LITRLEEQFTQYDIEQISGLSSAYAVRMYELLICWRSTGKTPIIELDEFRKRIGVLDTEY  180
            LITRLEEQFTQYDIEQISGLSSAYAVRMYELLICWRSTGKTPIIELDEFRKRIGVLDTEY
Sbjct  121  LITRLEEQFTQYDIEQISGLSSAYAVRMYELLICWRSTGKTPIIELDEFRKRIGVLDTEY  180

Query  181  TRTDNLKMRVIELALKQINERTDITASYEQHKKGRVITGFSFKFKHKKQNSDKTPKNSDS  240
            TRTDNLKM+VIELALKQINERTDITASYEQHKKGRVITGFSF FKHKKQNSDKTP  + S
Sbjct  181  TRTDNLKMQVIELALKQINERTDITASYEQHKKGRVITGFSFNFKHKKQNSDKTPCTNAS  240

Query  241  SPRIVKHSQIPTNIVKQPENAKMSDLEHRASRVTGEIMNNRLSDRFRQGDESAIDNMKRI  300
            SPRIVKHSQIPTNIVKQPENAKMSDLEHRASRVTGEIMNNRLSDRFKQGDESAIDNMKRI
Sbjct  241  SPRIVKHSQIPTNIVKQPENAKMSDLEHRASRVTGEIMNNRLSDRFKQGDESAIDNMKRI  300

Query  301  QSEIITDAIADQWESKLEEFGVVF  324
            QSEIITDAIADQWESKLEEFGVVF
Sbjct  301  QSEIITDAIADQWESKLEEFGVVF  324

>>>>sptrembl:N9LWE7_9GAMM N9lwe7 SubName: Full=Uncharacterized protein; 12/2013
Length=324

Score = 569 bits (1467),  Expect = 5e-160, Method: Compositional matrix adjust.
  Identities = 272/324 (83%), Positives = 294/324 (90%), Gaps = 0/324 (0%)

Query  1    MSDLIVKDNALMNASYNLALVEQRLILLAIIEARETGKGINANDPLTVRASSYINQFNVE  60
            MS+LIVKDNALMNASYNL LVEQRLILLAI+EARE GKGINANDPLTVRA SYINQF V
Sbjct  1    MSELIVKDNALMNASYNLDLVEQRLILLAIVEARESGKGINANDPLTVRAESYINQFGVR  60

Query  61   RHTAYQALKDACKDLFARQFSYQEKRERGRINITSRWVSQIGYMDDTATVEIIFAPAVVP  120
            R TAYQALKDACKDLFARQFSYQEKRERGR NITSRWVSQI Y+D+TATVEIIFAPAVVP
Sbjct  61   RTTAYQALKDACKDLFARQFSYQEKRERGRANITSRWVSQIAYIDETATVEIIFAPAVVP  120

Query  121  LITRLEEQFTQYDIEQISGLSSAYAVRMYELLICWRSTGKTPIIELDEFRKRIGVLDTEY  180
            LITRLE+QFTQYDIEQISGLSSAYAVRMYELLICWRSTGKTP+IEL KFRKRIGVLDTEY
```

FIG. 1D

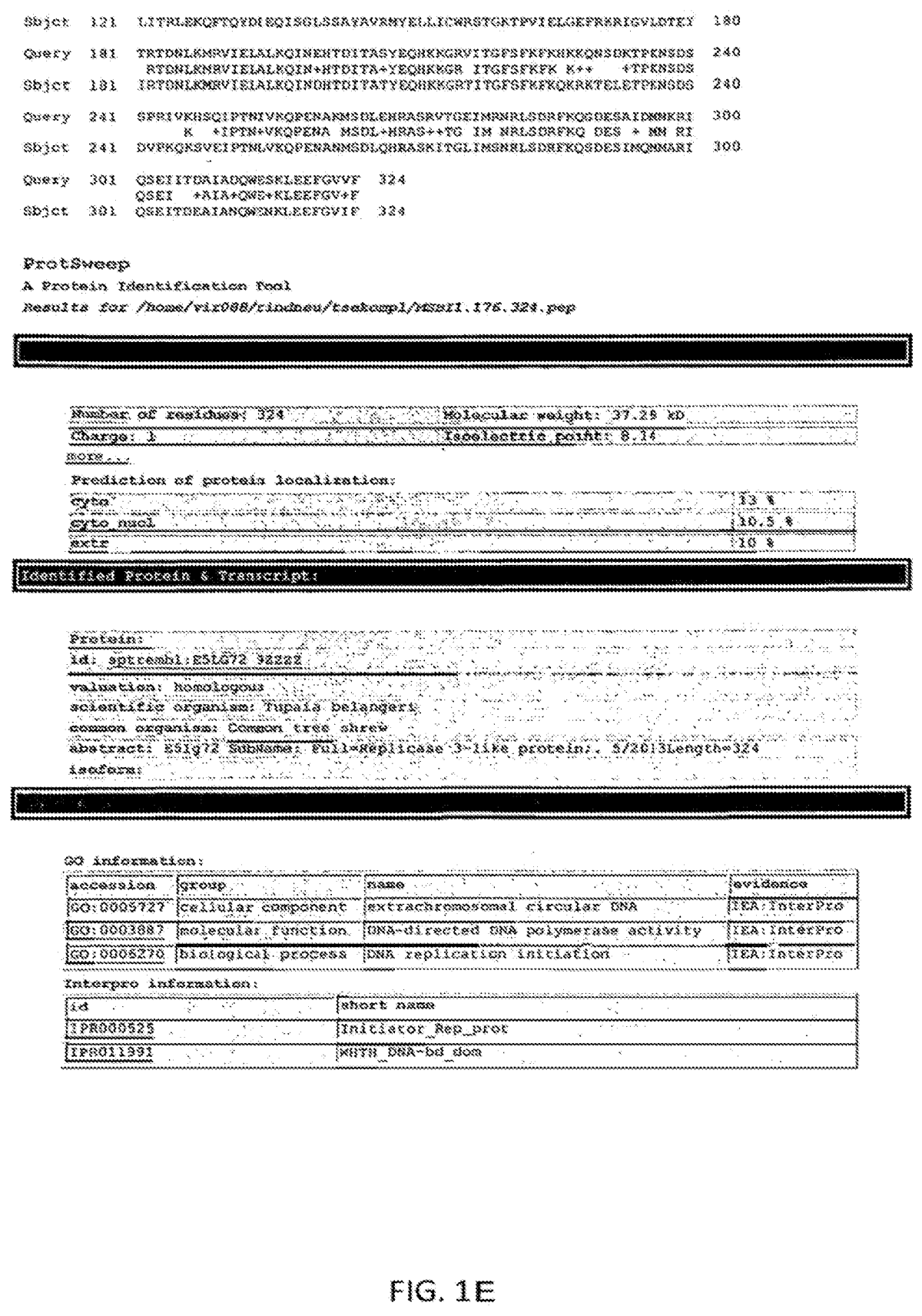

```
Sbjct  121   LITRLEKQFTQYDIEQISGLSSAYAVAMYELLICWRSTGATPVIELGEFRERIGVLDTEY  180

Query  181   TRTDNLKMRVIELALRQINEHTDITASYEQHKKGRVITGFSFKFKHKKQNSDKTPKNSDS  240
             RTDNLKMRVIELALRQIN+HTDITA+YEQHKKGR ITGFSFKFK K++   +TPKNSDS
Sbjct  181   IRTDNLKMRVIELALRQINDHTDITATYEQHKKGRTITGFSFKFKQKRKTELETPKNSDS  240

Query  241   SFRIVKRSQIPTNIVKQPENAKMSDLENRASRVTGEIMRNRLSDRFKQSDKESAIDMNKRI  300
             K   +IPTN+VKQPENA MSDL+HRAS++TG IM NRLSDRFKQ DES + MM RI
Sbjct  241   DVFKQKSVEIPTMLVKQPENANMSDLQHRASKITGLIMSNRLSDRFKQSDESIMQMNARI  300

Query  301   QSEIITDRIAOQWESKLEEFGVVF  324
             QSEI  +RIA+QWE+KLEEFGV+F
Sbjct  301   QSEITDRAIANQWENKLEEFGVIF  324
```

ProtSweep
A Protein Identification Tool
Results for /home/rir008/rindneu/testcmpl/MKBII.175.324.pep

| Number of residues: 324 | Molecular weight: 37.28 kD |
| Charge: 1 | Isoelectric point: 8.14 | more...

Prediction of protein localization:

| cyto | 13 % |
| cyto_nucl | 10.5 % |
| extr | 10 % |

Identified Protein & Transcript:

Protein:
id: sptrembl:E5LG72_9ZZZZ valuation: homologous
scientific organism: Tupaia belangeri
common organism: Common tree shrew
abstract: E5LG72 SubName: Full=Replicase 3-like protein;. S/20|3Length=324
isoform:

GO information:

| accession | group | name | evidence |
|---|---|---|---|
| GO:0005727 | cellular component | extrachromosomal circular DNA | IEA:InterPro |
| GO:0003887 | molecular function | DNA-directed DNA polymerase activity | IEA:InterPro |
| GO:0006270 | biological process | DNA replication initiation | IEA:InterPro |

Interpro information:

| id | short name |
|---|---|
| IPR000525 | Initiator_Rep_prot |
| IPR011391 | HTH_DNA-bd_dom |

FIG. 1E

*MSBI2.176  (1766bp)*

*(ms36.NnXn.1800.6)*

```
AAGCTTGCTTAGTCAAAAAAGTTTGAGCAAAGCGAAAACATAGGGCAATTTTCGTGATGAAAATGGGCTTTTAATGTTTTTAA
ATGCTTTTAAATGCTTTTAGACATGCTGAAACGCTTATATAGCAATGCATACAGAGGACATATGTCCACGTTTACCTATCAAT
ATCTCCACGTTTACCTATCAATATGTCCACGTTTACCTATCAATATGTCCACGTTTACCTGCGTATTTACACACATTTAAAT
AGTATGGATATATCCAATGAAATTATAATGTGTACTTATGAGCAAATTAGTAGTGAAAGACAATGCCCTAATGAACGCTAGTT
ACAACTTGGATCTCGTTGAACAGCGTTTAATTCTATTGGCAATCATCGAAGCAAGAGAATCAGGCAAAGGAATTAATGCAAAT
GACCCGCTACCGGTTCATGCAGAGAGTTATATCAATCAATTTGGTGTTCATCGAGTAACTGCATATCAAGCTCTCAAAGATGC
TTGTGATAACTTGTTTGCACGTCAATTCAGCTACCAATCCAAAAGTGAAAAAGGAACATACAAAATCATCGTTCACGTTGGG
TTAGTGAAATTATTTACATTGATACAGAAGCAACAGTAAAAATAATATTTGCACCTGCTATTGTCCCACTGATTACAAGGCTA
GAAGAACAGTTCACCAAGTATGATATTGAGCAAATTAGTGATTTATCGAGTGCTTATGCAATTCGCTTATACGAGTTATTGAT
TTGCTGGCGTAGCACAGGGAAAACACCAATTATTGGGCTAGGCGAAATTAGAAATCGGGTTGGTGTGTTAGATAGTGAATATC
ATCGAATTGCACACTTGAAAGAACGAGTTATTGAACATTCAATTAAACAGATTAACGAGCATACCGACATCACAGCCACCTAC
GAACAGCACAAAAAGGGCGGACAATCACAGGATTTTCATTCAAGTTTAAGCAGAAGAAGCCCAAACAAGCCGAAATTGCTAC
AGAAACGCCAAAAACAGCCACGAATGACCCAGACACGACAAAACCCCTACAGAGCCTCAGATCGCAAAATACAGCATGATTC
TGTGCAAACTAGGCAGTATTTCAGACTTGAGTAACTTCCCAGACTATCCAGCTTTTGCAAATTGGATTGGGAACATTTTGAGG
AACCCTGAAAAAGCAGATGAACAAATAGCAAAACGGATTTTCACAGCATTGAAAACAGAAACCGACTACAGCAAGAAAAACTA
ATTTTTAGTTGTGATGGGTTTTCCCGAAATAACATGAAGGGCGCACTTACGCAAAATTTTTGCTACGCCAAATTTTGCAAGTA
CGGTCAGGGAAACCCCGACACCCCAAAAGCAAAAACACTGTAATCAGGGAAAAAACATTTTTGATTTTGATCCTTGTTTGTCA
CTCGTAGACACTCGTTTTGTTTGCTCTTTCTAGAATTCACAAAAAAGATATTAGCGAGTGTCTACGAGCGACTCAATGAAAG
TTCGATTATTCCCCCTCTGGAAAACCGCTTTTAAAAATATTGGCTGCTAGATGGTTTTTACTATAGTGAGGTTTTGCTTTTAA
AAAAACACGAGCAAAGCGAGTTCATAGTTGCTTTTGCTTGTTTTCGGGTCTTAGGGGAAATCCCCTAACAAGTCCTCGAATAT
CAAAATGTGGCTACATTTTGTATATACGGGTAGGCTTGCTTATTTGATTTTTTTTCTTCTAAACCTTTGACTTCTTCCCCATT
GTTTGCAGAAATGCCCCCCGACC
```

*Repeat ~ 3x 22nt + 18nt*

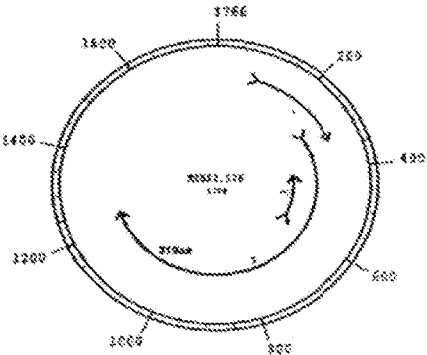

*78% nucleotide similarity in 984nt and 95-99% to 431nt of TSE-associated circular DNA isolate Sphinx 1.76*

*ORF:  319aa – initiation replication-B protein 65% amino acid similarity to Acinetobacter radioresistens*

FIG. 1F

*Blastn ~ Geall:*

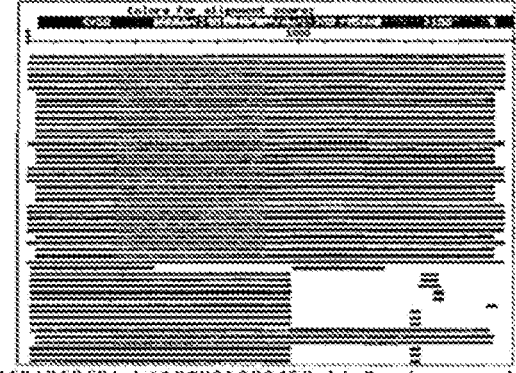

```
>>>nrnuc:GI_462476960   GI:462476960|gb|APGK01000458.1| Dendro...   1943      0.0
>>>nrnuc:GI_347602255   GI:347602255|gb|JN541288.1| Uncultured...   1445      0.0
>>>nrnuc:GI_462476960   GI:462476960|gb|APGK01000458.1| Dendroctonus ponderosae Seq01000458,
whole genome shotgun sequence. 0/0
Length=1455
 Score = 1943 bits (2154),  Expect = 0.0
 Identities = 1202/1284 (93%),  Gaps = 1/1284 (0%)
 Strand=Plus/Minus Query  11    AGTCAAAAAAGTTTCAGCAAAGCCGAAAACATACGGCCAATTTTCGTCATGAAAATGGGCTT  70
             ||||||||||||||||||  |||||||||||||||||||||||| | || ||| ||||||||
Sbjct  1318  AGTCAAAAAAGTTTGAGAGAAGCCGAAAACATAGGGCAATTT--CATGGTGAGAATGGGCTT  1260

Query  71    TTAATGTTTTTAAATGCTTTTAAATGCTTTTAGACATGCTGAAACGCTTATATAGCAATG  130
             ||||  ||||||||| |||||||||||||||||||||||||||||||||||    | | |||| |
Sbjct  1259  TTAAGGTTTTTAAAAGCTTTTAAATGCTTTTAGACATGCTGAAACGACCACACAGCAAGG  1200

Query  131   CATACAGAGGACATATGTCCACGTTTACCTATCAATATGTCCACGTTTACCTATCAATAT  190
             |||||||||| ||||||||||||||||||||||||||||||||||||||||||||||||||||
Sbjct  1199  CATACAGAGGGCATATGTCCACGTTTACCTATCAATATGTCCACGTTTACCTATCAATAT  1140

Query  191   GTCCACGTTTACCTATCAATATGTCCACGTTTACCTTGCGTATTTACACACATTTAAATA  250
             |||||||||||||||||||||||||||||||||||||||||||| || | ||||| |||||||||
Sbjct  1139  GTCCACGTTTACCTATCAATATGTCCACGTTTACCTTGCATAGTCACACATATTTAAATA  1080

Query  251   GTATGGATATATCCAATGAAATTATAATGTGTACTTATGAGCAAATTAGTAGTGAAAGAC  310
             |||||||||||||||||| ||||||||||||||||||||||||||||| | ||||||||||||||||
Sbjct  1079  ATATGGATATATCCAATAAAATTATAATGTGTACTTATGAGTAGGTTAGTAGTGAAAGAC  1020

Query  311   AATGCCCTAATGAACGCTAGTTACAACTTGGATCTCGTTGAACAGCGTTTAATTCTATTG  370
             |||||||||||||||||||||||||||| ||||||||||||||||||||||||||||||||| ||||||
Sbjct  1019  AATGCCCTAATGAACGCTAGTTATAACTTGGATCTCGTTGAACAGCGTTTAATCCTATTG  960

Query  371   GCAATCATCGAAGCAAGAGAATCAGGCAAAGGAATTAATGCAAATGACCCGCTTACGGTT  430
             ||||||||||||||| || || |||||||||||||||||| || ||||||||| || ||  |
Sbjct  959   GCAATCATCGAAGCGAGGGAGTCAGGCAAAGGAATTAACGCCAATGACCCTCTAACAATC  900

Query  431   CATGCAGAGAGTTATATCAATCAATTTGGTGTTCATCGAGTAACTGCATATCAAGCTCTC  490
             ||||||||||| || :||||||||||||||||||||||||||||||||||||||||||||||||||||
Sbjct  899   CATGCAGAGAGCTACATCAATCAATTTGGTGTTCATCGAGTAACTGCATATCAAGCTCTC  840

Query  491   AAAGATGCTTGTCATAACTTGTTTGCACGTCAATTCAGCTACCAATCCAAAAGTGAAAAA  550
             |||||||||||||||||||| |||||||||||||||||||||||| || ||||||||||||||||
Sbjct  839   AAAGATGCTTGTGATAACCTGTTTGCACGTCAATTCAGCTATCAGTCCAAAAGTGAAAAA  780

Query  551   GGGAACATACAAAATCATCGTTCACGTTGGGTTAGTGAAATTATTTACATTGATACAGAA  610
             || |||||||||||||||||||||||||||| |||||||||||||||||||||||| || |||||||
Sbjct  779   GGAAACATACAAAATCATCGTTCACGCTGGGTTAGTGAAATTATTTACATCGACACAGAA  720

Query  611   GCAACAGTAAAAATAATATTTGCACCTGCTATTGTCCCACTGATTACAAGGCTAGAAGAA  670
             ||||||||||||||||||| ||||||||||||||||||| |||||||||||||||| ||||||||
Sbjct  719   GCAACAGTAAAAATAATCTTTGCACCTGCTATCGTCCCACTGATTACAAGATTAGAAGAA  660
```

FIG. 1G

```
Query   671  CAGTTCACCAAGTATGATATTGAGCAAATTAGTGATTTATCGAGTGCTTATGCAATTCGC   730
             |||||||||||||||||||||| ||||||||||||||||||||||||||||||||| |||
Sbjct   659  CAGTTCACCAAGTATGATATTCAGCAAATTAGTGATTTATCGAGTGCTTATGCAATCCGC   600

Query   731  TTATACGAGTTATTGATTTGCTGGCGTAGCACAGGGAAAACACCAATTATTGGGCTAGGC   790
             |||||||| |||||||||||| |||||||||||||||||||||| ||||||||||  |||
Sbjct   599  TTATACGAATTATTGATTTGTTGGCGTAGCACAGGGAAAACGCCAATTATTGAATTAGCT   540

Query   791  GAATTTAGAAATCGGGTTGGTGTGTTAGATAGTGAATATCATCGAATTGCACACTTGAAA   850
             |||||||| ||||||||||||||||||||||||| ||||||||||||||||| |||||||
Sbjct   539  GAATTTAGGAATCGGGTTGGTGTGTTAGATACTGAATATCATCGAATTGCCCACTTGAAA   480

Query   851  GAACGAGTTATTGAACATTCAATTAAACAGATTAACGAGCATACCGACATCACAGCCACC   910
             || ||||||||||||||||||||||||||||| |||||||| |||||||||||| | |||
Sbjct   479  GAGCGAGTTATTGAACATTCAATTAAACAAATTAACGAACATACCGACATCACAGCGACC   420

Query   911  TACGAACAGCACAAAAAAGGGCCGACAATCACAGGATTTTCATTCAAGTTTAAGCAGAAG   970
             |||||||||||| |||||||||||||    || ||||| || ||||||||| ||||||||
Sbjct   419  TACGAACAGCATAAAAAAGGGCGAGTGATTACAGGGTTCTCATTCAAATTTAAGCAGAAG   360

Query   971  AAGCCCAAACAAGCCGAAATTGCTACAGAAACGCCAAAAACAGCCACGAATGACCCAGAC   1030
             ||||||||||||||||| ||||| ||||||||||| ||||||||||||||||||||||| 
Sbjct   359  AAGCCCAAACAAGCCGAGATTGCCACAGAAACGCCCAAAACAGCCACGAATGACCTAGAT   300

Query  1031  ACGACAAAACCCCTTACAGAGCCTCAGATCGCAAAATACAGCATGATTCTGTGCAAACTA   1090
             |||| |||||||||||||||||| ||||||||||||||||||||||||||||||||||||
Sbjct   299  ACGATAAAACCCCTTACAGAGCCACAGATCGCAAAATACAGCATGATTCTGTGCAAACTA   240

Query  1091  GGCAGTATTTCAGACTTGAGTAACTTCCCAGACTATCCAGCTTTTGCAAATTGGATTGGG   1150
             |||||||||||||||| |||||||||||||||||||||||||||||||||| ||||||||
Sbjct   239  GGCAGTATTTCAGACTTGAGTAACTTCCCAGACTATCCAGCTTTTGCAAATTGGATTGGG   180

Query  1151  AACATTTGAGGAACCCTGAAAAAGCAGATGAACAAATAGCAAAACGGATTTTCACAGCA   1210
             ||||||||||||||||||||||||||||||||||||||||||||||||||||||||||||
Sbjct   179  AACATTTGAGGAACCCTGAAAAAGCAGATGAACAAATAGCAAAACGGATTTTCACAGCA   120

Query  1211  TTGAAAACAGAAACCGACTACAGCAAGAAAAACTAATTTTTAGTTGTGATGGTTTTCCC   1270
             ||||||||||||||||||||||||||| |||||||||||||||||||||||||||||||
Sbjct   119  TTGAAAACAGAAACCGACTACAGCAAGAAAAACTAATTTTTAGTTGTGATGGTTTTCCC   60

Query  1271  GAAATAACATGAAGGGCGCACTTA   1294
             ||||||||||||||||||||||||
Sbjct    59  GAAATAACATGAAGGGCGCACTTA   36
```

Score =  134 bits (148),  Expect = 3e-27
Identities = 108/127 (85%),  Gaps = 4/127 (3%)
Strand=Plus/Minus

```
Query  1641  CCTAACAAGTCCTCGAATATCAAAATGTGGCTACATTTTGTATATACGGGTAGGCTTGCT   1700
             ||||||||||||| ||||||||||||||||||||||||||||||||||||||||||||||
Sbjct  1455  CCTAACAAGTCCCCGAATATCAAAATGTGGCTACATTTTGTATATACGGGTAGGCTTGCT   1396

Query  1701  TATTTGAttttttttC-TTCTAAACCTTT-GACTTCTTCCCCATTGTTTGCAGAAATGCC   1758
             ||||  || |  ||  | ||||||||||| |||| |||||  ||||| |  |||| |||| |
Sbjct  1395  TATTTGAATCTAATTCCTTTTTAAACCTTTCGACT--TTCCCTATCCTTTGCATAAATTGC   1338

Query  1759  CCCCGAC   1765
             ||| |||
Sbjct  1337  CCCTGAC   1331
```

>>>>nrnuc:GI_347602255 GI|347602255|gb|JN941288.1| Uncultured bacterium plasmid clone S6GIQ-17 genomic sequence, 0/0
Length=1215
 Score = 1449 bits (1606),  Expect = 0.0
 Identities = 858/893 (96%),  Gaps = 11/893 (1%)
 Strand=Plus/Plus

```
Query   881  ATTAACGAGCATACCGACATCACAGCCACCTACGAACAGCACAAAAAAGGGCGGACAATC   940
             || |||||||| ||||||||||||||||||||||||||||||||||||||||||||||||
Sbjct     1  ATCAACGAGCACACCGACATCACAGCCACCTACGAACAGCACAAAAAAGGGCGGACAATC   60

Query   941  ACAGGATTTTCATTCAAGTTTAAGCAGAAGAAGCCCAAACAAGCCGAAATTGCTACAGAA   1000
             ||||||||||||||||||||||||||||||||||||||||||||||||||||||||||||
Sbjct    61  ACAGGATTTTCATTCAAGTTTAAGCAGAAGAAGCCCAAACAAGCCGAAATTGCTACAGAA   120

Query  1001  ACGCCAAAAACAGCCACGAATGACCCAGACACGACAAAACCCCTTACAGAGCCTCAGATC   1060
```

FIG. 1H

```
                  ||||||||||||||||||||||||||||||||||||||||||||||||||||||||||||
Sbjct   121   ACGCCAAAAACACCCACGAATGACCCAGACACGACAAAACCCCTTACAGAGCCTCAGATC   180

Query  1061   GCAAAATACAGCATGATTCTGTGCAAACTAGGCAGTATTTCAGACTTGAGTAACTTCCCA   1120
              ||||||||||||||||||||||||||||||||||||||||||||||||||||||||:|||||
Sbjct   181   GCAAAATACAGCATGATTCTGTGCAAACTAGGCAGTATTTCAGACTTGAGTAACTTCCCA   240

Query  1121   GACTATCCAGCTTTTGCAAATTGGATTGGGAACATTTTGAGGAACCCTGAAAAAGCAGAT   1180
              |||||||||||||||||||||||||||||||||||||||||||||||||||||||:|||||
Sbjct   241   GACTATCCAGCTTTTGCAAATTGGATTGGGAACATTTTGAGGAACCCTGAAAAAGCAGAT   300

Query  1181   GAACAAATAGCAAAACGGATTTTCACAGCATTGAAAACAGAAACCGACTACAGCAAGAAA   1240
              ||||||||||||||||||||||||||||||||||||||||||||||||||||||||||||
Sbjct   301   GAACAAATAGCAAAACGGATTTTCACAGCATTGAAAACAGAAACCGACTACAGCAAGAAA   360

Query  1241   AACTAATTTTTAGTTGTGATGGGTTTTCCCGAAATAACATGAAGGGCGCACTTACGCA--   1298
              ||||||||||||||||||||||||||||||||||||||||||||||||||||||||  ||
Sbjct   361   AACTAATTTTTAGTTGTGATGGGTTTTCCCGAAATAACATGAAGGGCGCACTTAGCCATT   420

Query  1299   ------AAATTTTTGCTACGCCAAATTTTGCAAGTACGGTCAGGGAAACCCCGACACCCCA   1353
                    |||| || | |      ||| | |||| ||   || ||||||||   ||||||
Sbjct   421   GAGAAAAATCTTCGATTTTTTCAAT---GGAAGTCCGTGGGGGTAAACCCCTCAACCCCA   477

Query  1354   AAAGCAAAAACACTGTAATCAGGGAAAAAACATTTTTGATTTTGATCCTTGTTTGTCACT   1413
              |||||||||||||||||||||||||||||||||||||||||||||||||||||||||||||
Sbjct   478   AAAGCAAAAACACTGTAATCAGGGAAAAAACATTTTTGATTTTGATCCTTGTTTGTCACT   537

Query  1414   CGTAGACACTCGTTTTGTTTTGCTCTTCTAGAATTCACAAAAAAGATATTAGCGAGTGT   1473
              ||||||||||||:|||||||||||||||||||||||||||||||||||||||||||||||
Sbjct   538   CGTAGACACTCGTTTTGTTTTGCTCTTCTAGAATTCACAAAAAAGATATTAGCGAGTGT   597

Query  1474   CTACGAGCGACTCAATGAAAGTTCGATTATTCCCCCTCTGGAAAACCGCTTTTAAAAATA   1533
              |||||||||||||:||||||||||||||||||||||||||||||||||||||||||||||
Sbjct   598   CTACGAGCGACTCAATGAAAGTTCGATTATTCCCCCTCTGGAAAACCGCTTTTAAAAATA   657

Query  1534   TTGGCTGCTAGATGGTTTTTACTATAGTGAGGTTTTGCTTTTaaaaaaaCACGAGCAAAG   1593
              ||||||||||:||||||||||||||||||||||||||||||||||||||||||||||||||
Sbjct   658   TTGGCTGCTAGATGGTTTTTACTATAGTGAGGTTTTGCTTTTAAAAAAACACGAGCAAAG   717

Query  1594   CGAGTTCATAGTTGCTTTTGCTTGTTTTCGGGTCTTAGGGGAAATCCCCTAACAAGTCCT   1653
              ||||||||||||||||||||||||||||||||||||||||||||||||||||||||||||
Sbjct   718   CGAGTTCATAGTTGCTTTTGCTTGTTTTCGGGTCTTAGGGGAAATCCCCTAACAAGTCCT   777

Query  1654   CGAATATCAAAATGTGGCTACATTTTGTATATACGGGTAGGCTTGCTTATTTGAtttttt   1713
              |||||||||||:||||||||||||||||||||||||||||||||||||||||||||||||
Sbjct   778   CGAATATCAAAATGTGGCTACATTTTGTATATACGGGTAGGCTTGCTTATTTGATTTTTT   837

Query  1714   ttCTTCTAAACCTTTGACTTCTTCCCCATTGTTTGCAGAAA-TGCCCCCCGAC   1765
              |||||||||||||||||||||||||||||||||||||||||| |||||| ||||
Sbjct   838   TTCTTCTAAACCTTTGACTTCTTCCCCATTGTTTGCAGAAATTGCCCCTCGAC   890

Score = 576 bits (638),  Expect = 3e-160
Identities = 323/324 (99%),  Gaps = 0/324 (0%)
Strand=Plus/Plus
Query     1   AAGCTTGCTTAGTCAAAAAAGTTTGAGCAAAGCGAAAACATAGGGCAATTTTCGTGATGA   60
              ||||||||||||||||||||||||||||||||||||||||||||||||||||||||||||
Sbjct   892   AAGCTTGCTTAGTCAAAAAAGTTTGAGCAAAGCGAAAACATAGGGCAATTTTCGTGATGA   951

Query    61   AAATGGGCTTTTAATGTTTTTAAATGCTTTTAAATGCTTTTAGACATGCTGAAACGCTTA   120
              |||||||||||||||||||||||||||||||||||||||||||||||||||||||||||||
Sbjct   952   AAATGGGCTTTTAATGTTTTTAAATGCTTTTAAATGCTTTTAGACATGCTGAAACGCTTA   1011

Query   121   TATAGCAATGCATACAGAGGACATATGTCCACGTTTACCTATCAATATGTCCACGTTTAC   180
              ||||||||||||||||||||||||||||||||||||||||||||||||||||||||||||
Sbjct  1012   TATAGCAATGCATACAGAGGACATATGTCCACGTTTACCTATCAATATGTCCACGTTTAC   1071

Query   181   CTATCAATATGTCCACGTTTACCTATCAATATGTCCACGTTTACCTTGCGTATTTACACA   240
              ||||||||||||||||||||||||||||||||||||||||||||||||||||||||||||
Sbjct  1072   CTATCAATATGTCCACGTTTACCTATCAATATGTCCACGTTTACCTTGCGTATTTACACA   1131

Query   241   CATTTAAATAGTATGGATATATCCAATGAAAATTATAATGTGTACTTATGAGCAAATTAGT   300
              |||||||||||||||||||||||:|||||||| |||||||||||||||||||||||||||
Sbjct  1132   CATTTAAATAGTATGGATATATCCAATGAGATTATAATGTGTACTTATGAGCAAATTAGT   1191

Query   301   AGTGAAAGACAATGCCCTAATGAA   324
              ||||||||||||||||||||| ||
Sbjct  1192   AGTGAAAGACAATGCCCTAATCAA   1215
```

FIG. 1I

*BlastP – Uniprot:*
*ORF 319aa:*

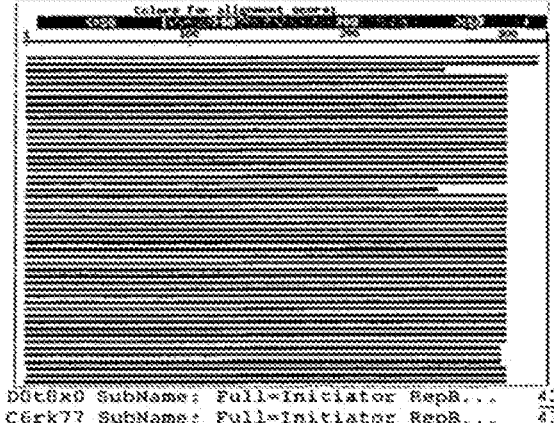

```
>>>sptrembl:D0T8X0_ACIRA   D0t8x0 SubName: Full=Initiator RepB...    435    1e-119
>>>sptrembl:C6RK77_ACIRA   C6rk77 SubName: Full=Initiator RepB...    435    1e-119

>>>>sptrembl:D0T8X0_ACIRA D0t8x0 SubName: Full=Initiator RepB protein;. 9/2013
Length=313
  Score =  435 bits (1118),  Expect = 1e-119, Method: Compositional matrix adjust.
  Identities = 208/319 (65%), Positives = 252/319 (78%), Gaps = 7/319 (2%)

Query   1    MSKLVVKDNALMNASYNLDLVEQRLILLAIIEARESGKGINANDPLTVHAESYINQFGVR    60
             M +LVVKDNAL+NASYNLDLVEQRLILLAI+EARESGKGINANDPL VHAESYINQF VR
Sbjct   1    MRELVVKDNALINASYNLDLVEQRLILLAIVEARESGKGINANDPLVVHAESYINQFNVR    60

Query   61   RVTAYQALKDACDNLFARQFSYQSKSEKGNIQNHRSRWVSEIIYIDTEATVKIIFAPAIV   120
             R TAYQALKDAC +LF RQFSYQ ++GN++++RSRWVSEI Y+D EA VK+IFAPAIV
Sbjct   61   RNTAYQALKDACHDLFVRQFSYQKVNDRGNVEHYRSRWVSEIGYVDNEAIVKLIFAPAIV   120

Query   121  PLITRLEEQFTKYDIEQISDLSSAYAISLYELLICWRSTGKTPIIGLGEFRNRVGVLDSE   180
             PLITRLEEQFTKY+++Q+S L+SAYA+RLYELLI WRSTGKTP+I L +FR R+G+L++E
Sbjct   121  PLITRLEEQFTKYELQQVSQLTSAYAVRLYELLIAWRSTGKTPVIELADFRKRIGILETE   180

Query   181  YHRIAHLKERVIEHSIKQINEHTDITATYEQHKKGRTITGFSFKFKQKKPKQAEIATETP   240
             Y R+   K  V+E +I QINEHTDI   YEQHKKGR+I GFSF F QK+ K+      E
Sbjct   181  YERMERFETSVLEAINQINEHTDINVAYEQHRKGRSIVGFSFNFSQKERKR----ILEKA   237

Query   241  KTATNDPDTTKPLTEPQIAKYSMILCKLGSISDLSNFPDYPAFANWIGNILRNPEKADEQ   300
             + +     + K LTE QI KYS +L KL +SDLS F DY +F+ WIGNILR PE     +
Sbjct   238  QVS------EGPKKLTEAQITKYSTVLSKLHELSQLSYPQDYQSFSIWIGNILREKPESVRPE   293

Query   301  IAKRIFTALKTETDYSKKN   319
             A+RIF++L   TD++  N
Sbjct   294  TAERIFSSLFKRYDFASPN   312

>>>>sptrembl:C6RK77_ACIRA C6rk77 SubName: Full=Initiator RepB protein;. 9/2013
Length=313
  Score =  435 bits (1118),  Expect = 1e-119, Method: Compositional matrix adjust.
  Identities = 208/319 (65%), Positives = 252/319 (78%), Gaps = 7/319 (2%)
Query   1    MSKLVVKDNALMNASYNLDLVEQRLILLAIIEARESGKGINANDPLTVHAESYINQFGVR    60
             M +LVVKDNAL+NASYNLDLVEQRLILLAI+EARESGKGINANDPL VHAESYINQF VR
Sbjct   1    MRELVVKDNALINASYNLDLVEQRLILLAIVEARESGKGINANDPLVVHAESYINQFNVR    60

Query   61   RVTAYQALKDACDNLFARQFSYQSKSEKGNIQNHRSRWVSEIIYIDTEATVKIIFAPAIV   120
             R TAYQALKDAC +LF RQFSYQ +++GN+++RSRWVSEI Y+D EA VK+IFAPAIV
Sbjct   61   RNTAYQALKDACHDLFVRQFSYQKVNDRGNVEHYRSRWVSEIGYVDNEAIVRLIFAPAIV   120

Query   121  PLITRLEEQFTKYDIEQISDLSSAYAIRLYELLICWRSTGKTPIIGLGEFRNRVGVLDSE   180
             PLITRLEEQFTKY+++Q+S L+SAYA+RLYELLI WRSTGKTP+I L +FR R+G+L++E
Sbjct   121  PLITRLEEQFKYELQQVSQLTSAYAVRLYELLIAWRSTGKTPVIELADFRKRIGILETE   180

Query   181  YHRIAHLKERVIEHSIKQINEHTDITATYEQHKKGRTITGFSFKFKQKKPKQAEIATETP   240
```

FIG. 1J

Figure 1K:
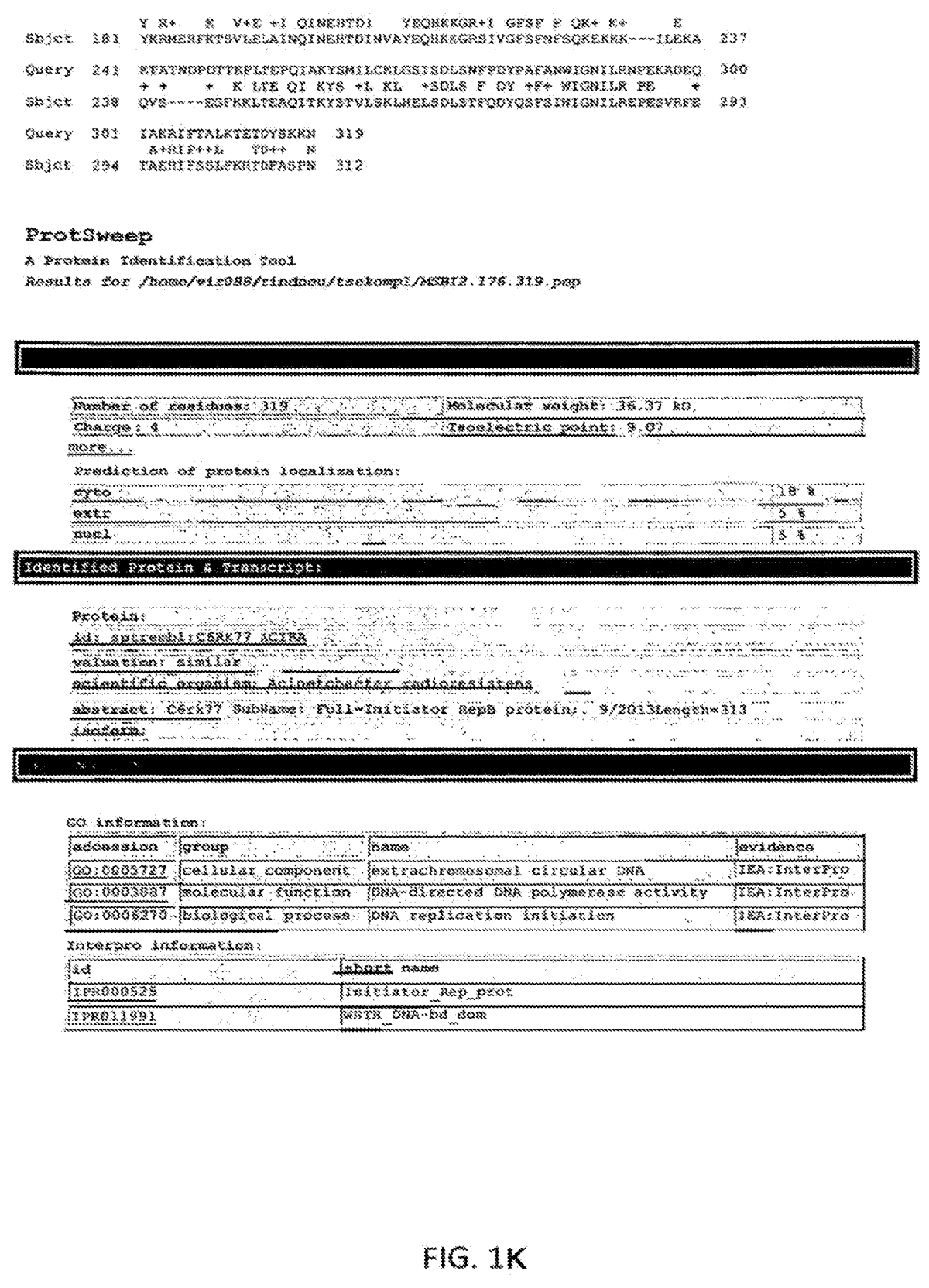

```
                 Y X+    X  V+X +I QINEXTDI    YEQXKKGR+I GFXF F QK+ K+     X
Sbjct  181   YRRMERFRTSVLELAINQINEXTDINVAYEQRKKGRSIVGFSFNFSQKEKEK---ILEKA  237

Query  241   NTATNOPOTTKPLTEPQIAKYSMILCKLGSISDLSNFPDYPAFANWIGNILRNPEKADEQ  300
                 + +    +  K LTE QI KYS +L KL  +SDLS F OY +F+ WIGNILR PE     +
Sbjct  238   QVS----EGFKKLTEAQITKYSTVLSKLHELSDLSTFQDYQSFSIWIGNILREPESVRFE  393

Query  301   IAKRIFTALKTETDYSKXN  319
                A+RIF++L   TD++  N
Sbjct  294   TAERIFSSLFKRTDFASFN  312
```

ProtSweep
A Protein Identification Tool
Results for /home/vir089/rindoeu/tsekompl/MSBI2.176.319.pep Number of residues: 319          Molecular weight: 36.37 kD
Charge: 4                        Isoelectric point: 9.07
more...
Prediction of protein localization:
cyto                                                            18 %
extr                                                            5 %
nucl                                                            5 %

Identified Protein & Transcript:

Protein:
id: spirembl:CSRK77_ACIRA
valuation: similar
scientific organism: Acinetobacter radioresistens
abstract: Csrk77 SubName: Full=Initiator RepB protein; 9/2013Length=313
isoform:

GO information:

| accession | group | name | evidence |
|---|---|---|---|
| GO:0005727 | cellular component | extrachromosomal circular DNA | IEA:InterPro |
| GO:0003887 | molecular function | DNA-directed DNA polymerase activity | IEA:InterPro |
| GO:0006270 | biological process | DNA replication initiation | IEA:InterPro |

Interpro information:

| id | short name |
|---|---|
| IPR000525 | Initiator_Rep_prot |
| IPR011991 | WHTH_DNA-bd_dom |

*Vitamin D deficiency results in TGFβ increase and higher rates of spontaneous EBV induction, seasonably pronounced in early spring (reduced UV-exposure)*

MSBI SEQUENCES AS AN EARLY MARKER FOR THE FUTURE DEVELOPMENT OF CANCER AND DISEASES OF THE CNS AND AS A TARGET FOR THE TREATMENT AND PREVENTION OF THESE DISEASES

RELATED APPLICATIONS AND INCORPORATION BY REFERENCE

This application is a divisional of U.S. application Ser. No. 16/362,941 filed Mar. 25, 2019 which is a continuation-in-part of U.S. application Ser. No. 15/402,579 filed Jan. 10, 2017 which is a continuation-in-part application of International Patent Application No. PCT/EP2015/001399 filed Jul. 9, 2015, which published as PCT Publication No. WO 2016/005054 on Jan. 14, 2016, which claims benefit of European Patent Application No. 14176624.6 filed Jul. 10, 2014.

SEQUENCE LISTING

The instant application contains a Sequence Listing which has been submitted electronically in ASCII format and is hereby incorporated by reference in its entirety. Said ASCII copy is named Y800501012SL.txt and is 41 kbytes in size.

FIELD OF THE INVENTION

The present invention relates to MSBI (Multiple Sclerosis Brain Isolate) nucleotide sequences as well as probes and primers which may comprise part of said nucleotide sequences and antibodies against polypeptides encoded by said nucleotide sequences. Finally, the present invention relates to the use of said compounds as an early marker for the future development of diseases such as cancer and diseases of the CNS and as a target for treatment and prevention of these diseases.

BACKGROUND OF THE INVENTION

Several epidemiological analyses conducted in recent decades indicate that the long-term consumption of "red" meat processed by different ways (including smoked or air-dried meat and meat as component of sausages consumed rare, undercooked or grilled) can be regarded as a risk factor for colon cancer (World Cancer Report 2007, zur Hausen 2012). "Red" meat is regarded as beef, pork, mutton, lamb and goat meat, in contrast to "white" meat (poultry meat/fish).

Thus far, chemical carcinogenic substances being produced during roasting, grilling, barbecuing, smoking and air-drying were blamed as risk factors for cancer. However, often the fact was disregarded that the same substances are also produced in comparable concentrations during analogous ways of preparation of poultry meat/fish. Accordingly, this does not support the assumption that these chemical substances play an exclusive role as regards the development of colon cancer. Since, in addition, the current epidemiological analyses suggest that beef is the main risk factor it has been postulated that an additional species-specific—presumably infectious—factor contributes to the triggering of this type of cancer (zur Hausen, 2012). The results of the correlation of analyses of the global spreading of domesticated bovine species with the global incidence of colon cancer seem to suggest that the consumption of meat of bovine species stemming from European/Asian cattle (*Bos*

*Taurus*) but not from breedings of zebu, water buffalo or yak might be of importance as a main risk factor (zur Hausen, 2015).

Citation or identification of any document in this application is not an admission that such document is available as prior art to the present invention.

SUMMARY OF THE INVENTION

Thus, the technical problem underlying the present invention is to identify specific nucleotide sequences that might be associated with diseases such as cancer or diseases of the CNS and, thus, to provide means for diagnosis and therapy.

The solution to said technical problem is achieved by providing the embodiments characterized in the claims.

During the experiments resulting in the present invention sera of cattle were screened for infectious agents—starting from the assumption that the presence in sera is also indicative for the presence of these agents in "red" meat. Sera from healthy cows were screened and new viral nucleic acid components could be isolated. The DNA sequences and open reading frames of several of these components showed a recognizable relationship to two sequences which were already described for transmissible spongiform encephalopathies (TSE) for TSE-diseases of sheep, cattle and humans.

The TSE isolates have also been suspected to play a role in cancer induction (Manuelidis, 2011), thus, it is reasonable to assume that the viral sequences described might be associated with the development of diseases like cancer, specifically colon and breast cancers but also Hodgkin's disease and others, and diseases of the CNS (Multiple sclerosis MS, amyotrophic lateral sclerosis, transmissible spongiforme encephalopathies/Prion-linked diseases, Parkinson's disease, Alzheimer disease).

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

Abbreviations for Figures Rep=replication protein; CP=capsid protein

CMI: cattle milk isolate

HCBI: healthy cattle blood isolate

MSCI: MS brain isolate

MSSI: MS serum isolate

Figure 3:
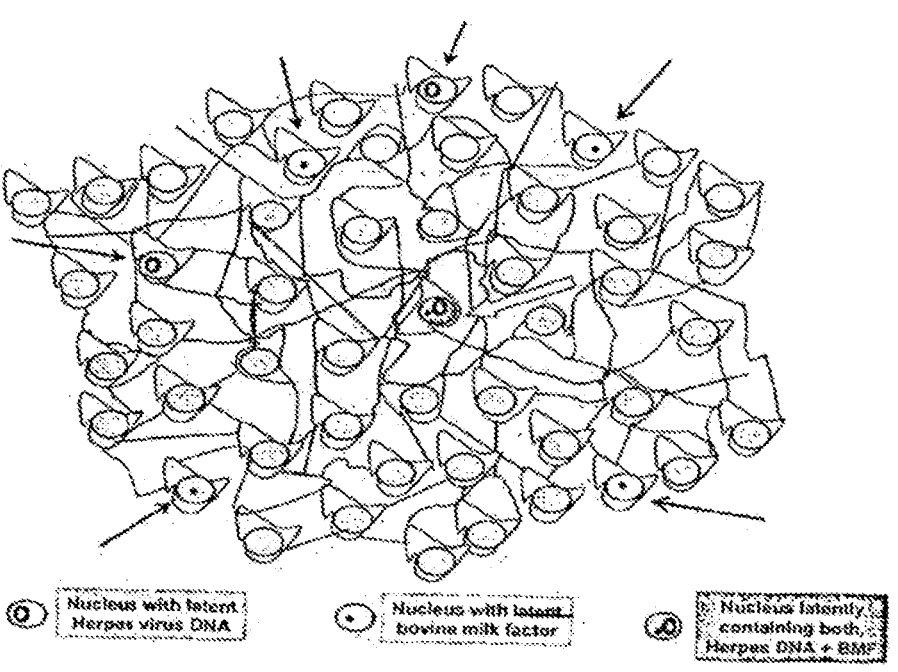
Figure 4:
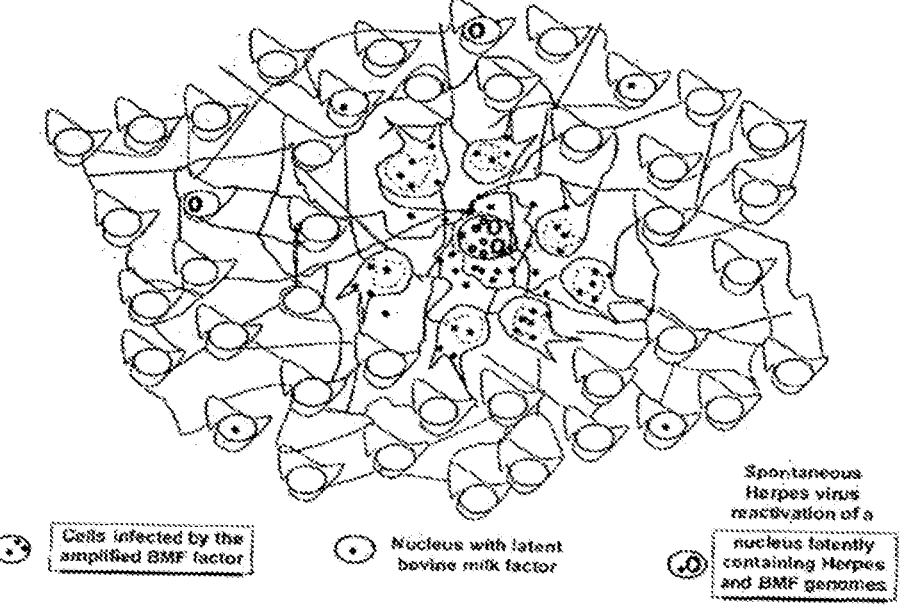
Figure 5:
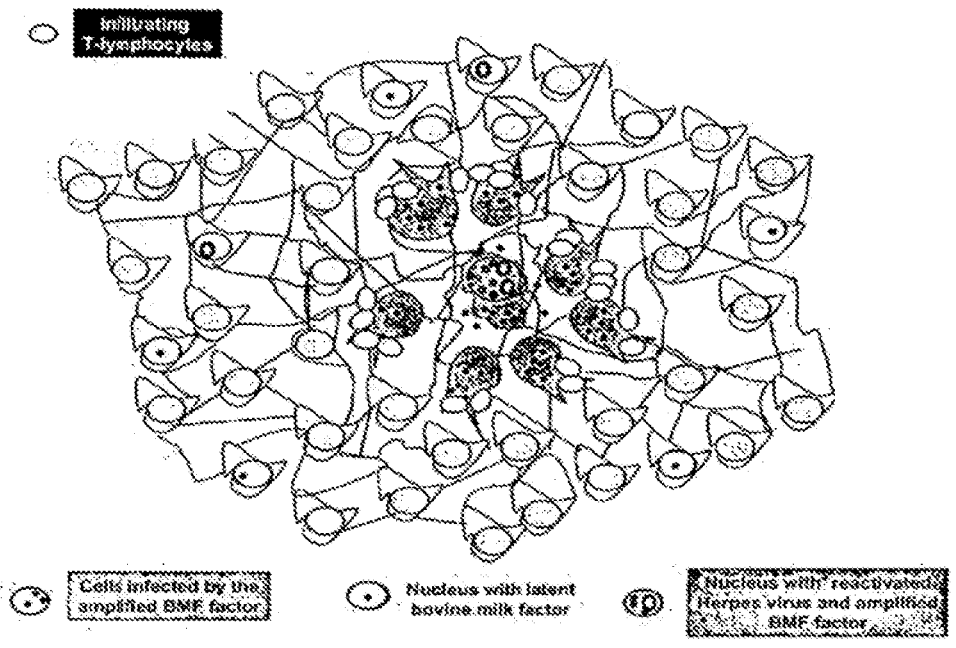

Sphinx: slow progressive hidden infection of variable (X) latency

FIGS. 1A-1 K:

Group 1—Isolates from bovine serum, bovine milk and multiple sclerosis (MS) brain samples (post mortem)— all related to Sphinx1.76

(A-E) MSBI1.176 (Multiple Sclerosis Brain Isolate) (1766 bp)—98% similar to Sphinx1.76

A: MSBI1.176 (SEQ ID NO:1)

B: query (SEQ ID NO:2), subject (SEQ ID NO:3)

C: query (SEQ ID NO:4), subject (SEQ ID NO:5)

D-E: E5LG72 query (SEQ ID NO:6), E5LG72 subject (SEQ ID NO:7);

N9LWE7 query (SEQ ID NO:8), N9LWE7 subject (SEQ ID NO:9)

(F-K) MSBI2.176 (1766 bp)—isolated from the same MS-brain sample as MSB1.176

F: MSBI2.176 (SEQ ID NO:10)

G: query (SEQ ID NO:11), subject (SEQ ID NO:12)

H: query (SEQ ID NO:13), subject (SEQ ID NO:14), uncultured bacterium plasmid clone query (SEQ ID NO:15), subject (SEQ ID NO:16)

I: query (SEQ ID NO:17), subject (SEQ ID NO:18)

J: DOT8X0 query (SEQ ID NO:19) DOT8X0 subject (SEQ ID NO:20),

K: C6RK77 query (SEQ ID NO:21), C6RK77 subject (SEQ ID NO:22)

The isolates were all generated by using back-to-back primers designed on the replication gene of Sphinx1.76.

Primers (several isolates were isolated twice by applying both primer pairs independently).

Nn (forward GGATTAATGCCAATGATCC (SEQ ID NO:23)), Xn (reverse CTTTGCCTGTTTCTCTCG (SEQ ID NO:24)), and/or No (forward GAGGACGAATTAATAT-TACAAGTC (SEQ ID NO:26), Xo (reverse GTTCTCGTTTTCTTGGTAA (SEQ ID NO:25))

FIG. 2:

Alignment of a replication gene/iteron-like repeat region between 8 isolates and Sphinx1.76

FIG. 3:

Schematic outline of latent infection of different types of brain cells with Herpes type genomes and BMF factor

FIG. 4:

Spontaneous reactivation of Herpes DNA in a cell concomitantly infected by Herpes and BMF DNA Amplification of BMF and inhibition of Herpes DNA replication.

FIG. 5:

Schematic outline of the recognition of foreign antigens by the immune system, T cell response

FIG. 6:

Mononuclear inflammatory cells surrounding a small vein in an early lesion

Lymphocytes, monocytes, plasma cells and occasional macrophages.

FIG. 7:

Advancing age of the lesion (plaque) on the left with normal white matter on the right Macrophages are present in the lesion (arrows) and at the interphase.

FIG. 8:

Schematic outline of the pathogenesis concept for multiple sclerosis

EBV is used as an example for the role of Herpes-type viruses.

FIG. 9:

Tentative Scheme of MS pathogenesis

DETAILED DESCRIPTION OF THE PRESENT INVENTION

In the present application a new concept for the pathogenesis of multiple sclerosis and cancer is presented: Interaction of an Amplifying Virus and the amplified DNA of a Bovine Milk (or serum) Factor (BMF)

The incidence of multiple sclerosis (MS) increased in several parts of the world (reviewed in Kurtzke, 2000, Alcalde-Cabero et al., 2013). This increase has been mainly attributed to environmental factors. Migrants from high to lower risk areas retain the MS risk of their birth place only if they are at least age 15 at migration, frequently interpreted to be due to an infection acquired during early childhood (reviewed in Kurtzke, 2000). Clustering of cases and the geographic epidemiology has also been widely discussed: A rising incidence of MS was noted in females linked to urbanization (Kotzamani et al., 2012).

Demyelinization is a characteristic feature of MS lesions. Four fundamentally different patterns of demyelination were found, defined on the basis of myelin protein loss, the location and extension of plaques, the patterns of oligodendrocyte destruction, and the immunopathological evidence of complement activation (Lucchinetti et al., 2000, Metz et al., 2014). At a given time point of the disease the patterns of demyelination were heterogeneous between patients; but they were homogenous within multiple active lesions from the same patient, potentially pointing to different contributing factors.

Two of the risk factors seem to deserve special attention: the relatively consistent results pointing to a possible role of different, predominantly herpes-group viruses, and the consumption of fresh cow milk, potentially including other dairy products (see below). In addition, Vitamin D deficiency plays a role as a risk factor.

Apparently all Herpes virus types share two properties which seem to be relevant for the subsequent discussion:

During their persistence in a latent stage, spontaneous reactivation may occur, in part regulated by specific gene functions, partly also by epigenetic mechanisms (reviewed in Nicoll et al., 2012, *Grinde*, 2013). Reactivation may also be triggered by interaction with extracellular cytokines, such as transforming growth factor β.

Spontaneous induction of a lytic cycle has been observed for virtually every human pathogenic Herpes virus type. The high antibody titers against Epstein-Barr virus structural proteins in EBV-positive Burkitt's lymphomas and nasopharyngeal cancers (reviewed in Henle, W. and Henle, G., 1977) may serve here as one example. Reactivations of human Herpes virus type 6, Varicella-Zoster virus, Herpes simplex virus and others are not rare events and may affect a number of different cell types (Hu Knox et al., 2000).

A second remarkable property of herpes virus infection represents the amplification of various double- or single-stranded small DNA virus genomes upon infection of cells containing such DNAs in a latent state. This has been noted for human and monkey Polyoma viruses, JC and SV40, for human and bovine Papilloma viruses, as well as for single-stranded Adeno-associated (AAV) and Anello-/TT-viruses (Schlehofer and zur Hausen, 1990, Heilbronn et al., 1993, Borkosky et al., 2012). The Herpes-group viruses used in these studies were Herpes simplex virus, human cytomegalovirus and Epstein-Barr virus. The potential to induce amplification of latent small viral DNA genomes is also shared by Adeno- and Vaccinia viruses (Schlehofer and zur Hausen, 1990). The helper effect of Herpes- and adenovirus-induced amplification of parvoviruses has been intensively studied for adeno-associated viruses. The replication of the latter seems to depend on this helper effect but in turn leads to a reduction of Herpes- or adenovirus replication due to the preferential amplification of small viral DNA (Schlehofer et al., 1983, Matz et al., 1984, Bantel Schaal and zur Hausen, 1988, Schmitt et al., 1989, Schlehofer and zur Hausen, 1990, Heilbronn et al., 1990a, Heilbronn et al., 1990b).

Spontaneous induction of Herpes-group viruses and the amplification of latent small viral DNA form the basis for the subsequent postulation of the mechanism underlying MS development.

Several reports noted a correlation between consumption of non-pasteurized cow milk and MS development (Murray T J. 1976, Sepcie et al., 1993, Malosse and Perron, 1993), whereas others stressed long-time consumption of cow milk as a risk factor, in particular when consumed in the early phase of life (Agranoff and Goldberg, 1974, Christensen, 1975, Warren, 1984, Butcher, 1976, 1986, Winer et al., 2001, Munger et al., 2011a).

If a specific factor in cow milk exists which increases the risk for MS development, one can anticipate a protective role of long-term breast-feeding. Long-term breast-feeding (for six months and more) has indeed repeatedly been reported as having a protective effect for MS development (Christensen, 1975, Warren, 1984, Tarrats et al., 2002, Conradi et al., 2013). The existence of a cow milk factor would also not exclude a specific genetic predisposition for the development of MS. A monogenic predisposition for MS has been reported in a chromosomal localization close to BRCA1 (Holzmann et al., 2013).

A role of vitamin-D deficiency has repeatedly been implicated for the initiation of MS (reviewed in Ascherio et al. 2012, 2013).

A convincing relationship between vitamin D deficiency and Epstein Barr Virus reactivation originates from early studies on EBV reactivation by transforming growth factor beta (TGF-β). A serum factor, purified and labeled as Epstein-Barr virus-inducing factor (EIF) (Bauer et al., 1982) proved to be identical to the subsequently described TGF-β molecule (Frolik et al., 1983, Bauer et al., 1991). TGF-β in turn is negatively regulated by activated vitamin D receptors (Isik et al., 2012, Ito et al., 2013, Zerr et al., 2014). This could very well explain the season-related preferential onset of MS and of exacerbations.

The relationship between low vitamin D and EBV reactivation is further supported by studies describing a correlation between low vitamin D and elevated immunoreactivity against Epstein-Barr virus prior to the clinical manifestation of multiple sclerosis (Munger et al., 2011b, Decard et al., 2012) and a higher rate of EBV excretion of EBV-positive MS patients in comparison to EBV-positive healthy controls (Yea et al., 2013).

Figure 8:
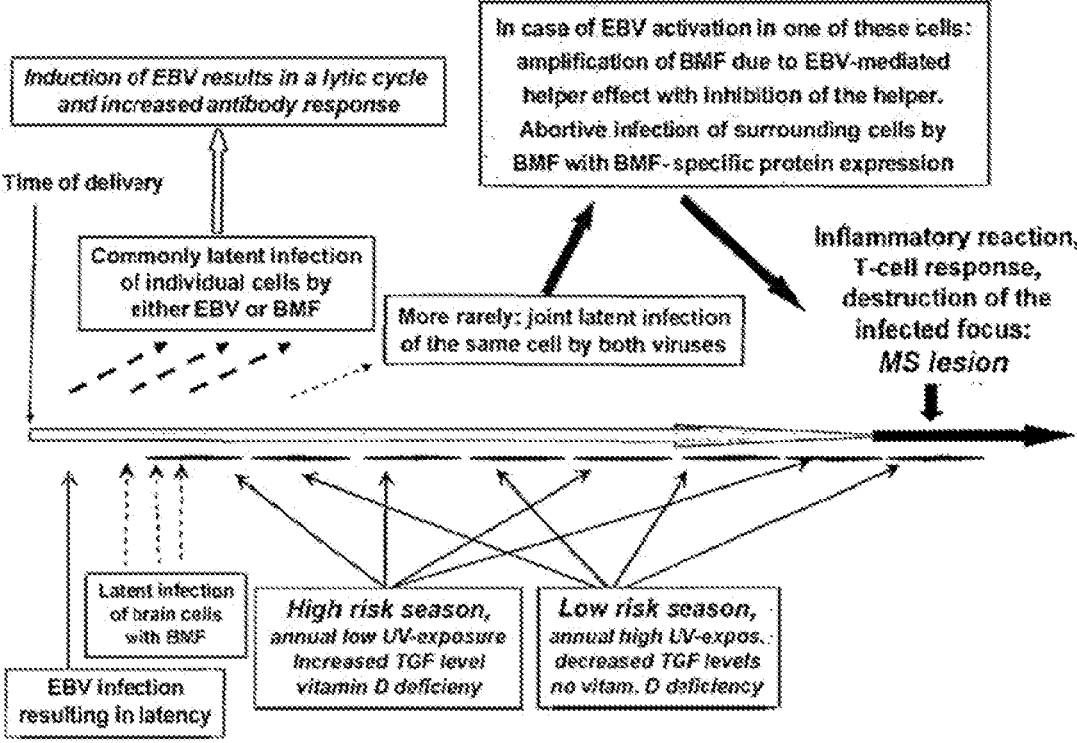
Figure 9:
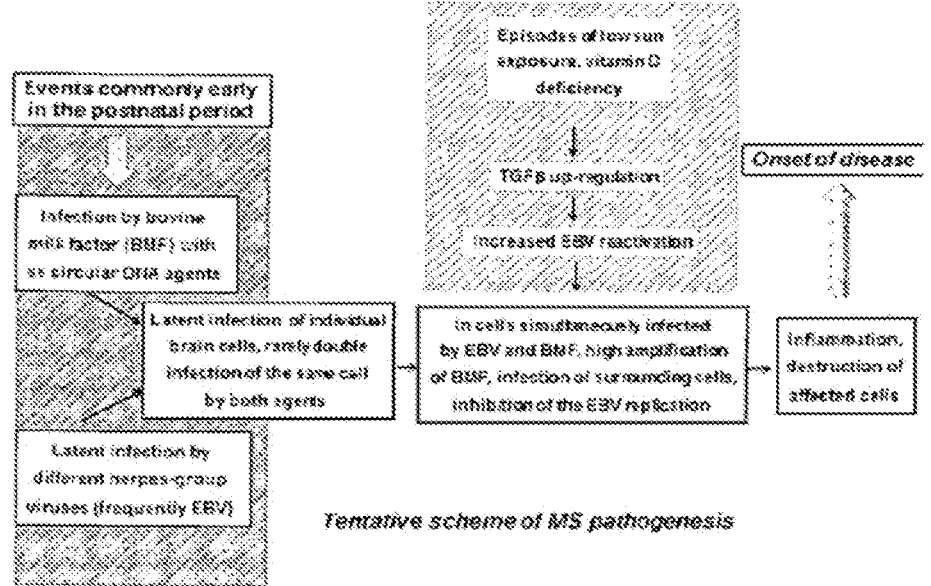

Thus, at least two factors have been implicated as potential etiological contributors for both diseases of the CNS (e.g. MS) and cancer (e.g. colon and breast cancer): vitamin D deficiency and the reactivation of various herpes group viruses, mainly Epstein-Barr virus (EBV), human herpes virus type 6, and varicella-zoster virus. According to the present invention the identification of several novel types of small circular single stranded DNAs, presumably of viral origin, from cattle sera of the present invention and commercially available dairy products, show a unifying concept. The inventors have demonstrated in the present invention that co-infection of cells with herpes-group viruses and small single-stranded or double-stranded DNA viruses results in an substantial amplification of small viral DNA with partial inhibition of the herpes virus. Some of the molecules identified in dairy cattle sera and milk are distantly related to DNA reported in prion-linked brain lesions and have been found in two autopsy lesions of patients with multiple sclerosis. The amplification of these single-stranded DNA molecules by reactivation of a co-latently persisting herpes virus genome could result in their amplification and evoking a local immune response resulting in destruction of the affected brain cells. This model could in part explain the North-South incidence gradient of multiple sclerosis, which is thought to be linked to vitamin-D deficiency and herpes virus reactivation (c.f. FIGS. 8 and 9)

In addition, the full-length genomes of the isolates from MS brains and sera were isolated and re-circularized before transfection into the human cell line 293TT. Transfected cells were harvested on day 3 and total RNA extracted using the miRNA Easy Kit (Qiagen). Samples were further purified (Dnase digestion, ribosome removal) and subjected to high throughput RNA sequencing. The RNA transcripts clearly show that the isolates replicate in human cells.

The inventors consider Vitamin D deficiency and herpes virus reactivations as risk factors also for breast and colon cancers. Reactivation of dual latent infections within the same cell, outlined above for multiple sclerosis pathogenesis, could therefore also play a particular important role in the aetiology of these cancers.

Thus, it is considered by the inventors that multiple sclerosis (MS) and also the other below mentioned diseases result from Latent infections of the same cell with two different infectious agents, one of them most likely a herpes-type virus (in particular EBV, HHV-6, VZV, but also HSV, HHV-7), the other one acquired by bovine milk consumption (bovine milk factor—BMF) as the first event. Each of them latently infects individual cells, but occasionally genomes of both agents occur within the same cell.

Reactivation of the herpes-type virus most frequently, but not only, Epstein Barr virus (EBV) to a lytic cycle as a second precondition. For EBV this is probably linked to increased levels of transforming growth factor β (TGF (β) which is negatively regulated by activated vitamin D receptors;

As third event, amplification of BMF, resulting in partial suppression of Herpes-type DNA synthesis and formation of BMF particles or spreading of its nucleic acid to neighbouring cells via neuronal interconnections;

This is followed by an infection of neighbouring cells with expression of BMF protein;

Finally, T-cell response against BMF leads to the destruction of affected cells and in case of MS to plaque formation. This supports the clinical observation of the focal appearance of lesions, commonly starting from a central vein and the intensive localized immune response in early lesions.

Transmissions of agents present in milk or dairy products may lead to latent infections in human brain cells followed by amplification of these agents in case of co-latency and spontaneous induction of a Herpes virus DNA or Herpes virus—like DNA. Potential BMF candidate agents are described in Examples 2-5 and the accompanying figures.

The presence of presumably circular single stranded DNA related to Sphinx-sequences, Anello-, Circo-, and Gemycircularvirus families, as well as *Psychrobacter* species in cattle sera, in commercially available milk samples, as well as in florid MS lesions and MS serum permits the development of a concept for MS pathogenesis. It integrates observations of involvement of Herpes-type viruses, most prominently of EBV, of their property to amplify small double- and single-stranded DNA viruses, of viral cow milk factors, of vitamin-D deficiency, the EBV inducing property of TGFβ, and the partial season dependence of MS onset and of exacerbation in the course of disease. This concept is schematically outlined in FIGS. 7-13.

An initial dual latent infection of the same or closely flanking cells by a herpes virus genome and the postulated BMF, followed by a trigger for Herpes virus reactivation and the subsequent preferential amplification of single-stranded DNA are defined as the primary event. In the case of latent EBV infection, vitamin D deficiency with the subsequent up-regulation of TNF-β, as an EBV-inducing factor could be the important trigger for up-regulation. Probably abortive infection of neighbouring cells with viral antigen expression results in an active T-cell response and the destruction of the affected cells. The frequently described seasonality of MS onset and of new rounds of MS exacerbations, the repeatedly reported North-South gradient of MS incidence should reflect the degree of sun-light exposure, negatively correlating vitamin D levels with TGFβ concentration and EBV reactivation.

Thus, the inventors anticipate the presence of different BMF sequences also in susceptible normal human brain cells in a latent form. The remarkable heterogeneity of the BMF isolates may also find its reflection in variations for pathologic characteristics of MS in humans (Lucchinetti et al., 2000, Metz et al., 2014). It would not be too surprising it eventually "high" and "low" risk types will be identified, in a certain analogy to human papillomavirus pathogenicity (zur Hausen, 1985). The majority of those carriers will not develop MS, since the latter should require latent co-infection of a BMF-positive cell with a Herpes-type virus and spontaneous induction of the latter. This should be a rare event, increasing, however, under conditions resulting in frequent Herpes virus reactivations.

As a final point, it should be of interest to also apply this concept to other presumably autoimmune diseases and certain cancers occurring at increased frequency under conditions of vitamin D deficiency. As far as cancers are concerned, this specifically accounts for colon- and breast cancer, and possibly for ovarian, prostate, pancreatic cancer and lung cancers.

The risk for insulin-dependent diabetes mellitus has been repeatedly linked to cow milk consumption and vitamin D deficiency (reviewed in Scott, 1990, in Grant, 2006, in Hyppönen et al, 2010). The latter system seems to come particularly close to the MS situation.

Accordingly, the present invention relates to a MSBI polynucleic acid which may comprise:

(a) a nucleotide sequence depicted in any one of FIGS. 1A to 1K;
(b) a nucleotide sequence having at least 90% identity to a nucleotide sequence of (a);
(c) a fragment of a nucleotide sequence of (a) or (b);
(d) a nucleotide sequence being complementary to a nucleotide sequence of (a), (b) or (c); or
(e) a nucleotide sequence which is redundant as a result of the degeneracy of the genetic code compared to any of the above-given nucleotide sequences.

The term "polynucleic acid" refers to a single-stranded or double-stranded nucleic acid sequence. A polynucleic acid may consist of deoxyribonucleotides or ribonucleotides, nucleotide analogues or modified nucleotides or may have been adapted for diagnostic or therapeutic purposes. A polynucleic acid may also comprise a double stranded cDNA clone which can be used, for example, for cloning purposes.

The MSBI polynucleic acids of the invention can be prepared according to well-known routine methods, for example, by (a) isolating the entire DNA or RNA from a sample, (b) detecting the HCBI, MSBI, MSSI or CMI sequence by hybridization or PCR and (c) cloning of the MSBI sequence into a vector.

Also included within the present invention are sequence variants of the polynucleic acid of the invention containing either deletions and/or insertions of one or more nucleotides, especially insertions or deletions of one or more codons, mainly at the extremities of oligonucleotides (either 3' or 5') and which show at least 90%, 91%, 92%, 93%, 94%, 95%, 96%, 97%, 98% or 99% identity to said polynucleic acid sequences of the invention. Polynucleic acid sequences according to the present invention which are similar to the sequences as shown in FIGS. 1A to 1K can be characterized and isolated according to any of the techniques known in the art, such as amplification by means of sequence-specific primers, hybridization with sequence-specific probes under more or less stringent conditions, sequence determination of the genetic information of MSBI etc.

The present invention also provides fragments of the nucleotide sequences of the present invention described above that signal a replication gene which codes for a replication protein. An autonomous replicating nucleotide sequence may comprise a nucleotide sequence of the replication gene or a fragment thereof which is capable of inducing autonomous replication.

Replication protein represents an endonuclease which binds single-stranded DNA inducing a single-stranded cut at or near the origin of replication (Wolds, 1997). The skilled person can derive at such fragments capable of inducing autonomous replication without undue experimentation. Such fragments may have a length of at least 45, at least 55, or at least 65 nt.

The person skilled in the art can easily determine which nucleic acid sequences are related to a nucleotide sequence of FIGS. 1A to 1K or which fragments are still capable of replicating autonomously by using standard assays.

The present invention also provides polynucleic acid sequences which are redundant as a result of the degeneracy of the genetic code compared to any of the above-given nucleotide sequences. These variant polynucleic acid sequences will thus encode the same amino acid sequence as the polynucleic acids they are derived from.

The MSBI polynucleic acids of the invention might be present as an extrachromosomal episome, might be integrated into the host's genome and/or might be linked to a host cell DNA.

The present invention also relates to an oligonucleotide primer which may comprise or consisting of part of a polynucleic acid as defined above, with said primer being able to act as primer for specifically sequencing or specifically amplifying MSBI polynucleic acid of the invention.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow priming the synthesis of the extension products. Preferably the primer is about 5-50 nucleotides. Specific length and sequence will depend on the complexity of the required DNA or RNA targets, as well as on the conditions of primer use such as temperature and ionic strength.

The fact that amplification primers do not have to match exactly with a corresponding template sequence to warrant proper amplification is amply documented in the Literature. The amplification method used can be, for example, polymerase chain reaction (PCR), ligase chain reaction (LCR), nucleic acid sequence-based amplification (NASBA), transcription-based amplification system (TAS), strand displacement amplification (SDA) or amplification by means of Qb replicase or any other suitable method to amplify nucleic acid molecules using primer extension. During amplification, the amplified products can be labelled either using labelled primers or by incorporating labelled nucleotides.

Labels may be isotopic (32P, 35S, etc.) or non-isotopic (biotin, digoxigenin, etc.). The amplification reaction is repeated between 20 and 70 times, advantageously between 25 and 45 times.

Any of a variety of sequencing reactions known in the art can be used to directly sequence the viral genetic information and determine the ORF by translating the sequence of the sample into the corresponding amino acid sequence. Exemplary sequencing reactions include those based on techniques developed by Sanger or Maxam and Gilbert. It is also contemplated that a variety of automated sequencing procedures may be utilized when performing the subject assays including sequencing by mass spectrometry (see, for example: PCT publication WO 94/16101). It will be evident to one skilled in the art that, for example the occurrence of only two or three nucleic bases needs to be determined in the sequencing reaction.

Preferably, these primers are about 5 to 50 nucleotides long, more preferably from about 10 to 25 nucleotides. Most preferred are primers having a length of at least 13 bases.

The present invention also relates to an oligonucleotide probe which may comprise or consisting of part of a MSBI polynucleic acid as defined above, with said probe being able to act as a hybridization probe for specific detection of a, MSBI polynucleic acid according to the invention.

The probe can be labelled or attached to a solid support.

The term "probe" refers to single stranded sequence-specific oligonucleotides which have a sequence which is complementary to the target sequence of a MSBI polynucleic acid to be detected.

Preferably, these probes are about 5 to 50 nucleotides long, more preferably from about 10 to 25 nucleotides. Most preferred 30 are probes having a length of at least 13 bases.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, NH2 groups, SH groups, carboxylic groups, or coupling with biotin or haptens.

The oligonucleotides according to the present invention, used as primers or probes may also contain or consist of nucleotide analogues such as phosphorothioates, alkylphosphoriates or peptide nucleic acids or may contain intercalating agents. These modifications will necessitate adaptions with respect to the conditions under which the oligonucleotide should be used to obtain the required specificity and sensitivity. However, the eventual results will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The polynucleic acids of the invention may be comprised in a composition of any kind. Said composition may be for diagnostic, therapeutic or prophylactic use.

The present invention also relates to a recombinant expression vector which may comprise a MSBI polynucleic acid of the invention as defined above operably linked to prokaryotic, eukaryotic or viral transcription and translation control elements as well as host cells containing such vector.

The term "vector" may comprise a plasmid, a cosmid, an artificial chromosome, a phage, or a virus or a transgenic non-human animal. Particularly useful for vaccine development may be MSBI recombinant molecules, BCG or adeno-viral vectors, as well as avipox recombinant viruses.

The term "recombinant expression" used within the context of the present invention refers to the fact that the polypeptides of the present invention are produced by recombinant expression methods be it in prokaryotes, or lower or higher eukaryotes as discussed in detail below.

The term "host cell" refers to cells which can be or have been, used as recipients for a recombinant vector or other transfer polynucleotide, and include the progeny of the original cell which has been transfected.

It is understood that the progeny of a single parental cell may not necessarily be completely identical in morphology or in genomic or total DNA complement as the original parent, due to natural, accidental, or deliberate mutation or recombination.

The term "lower eukaryote" refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluiveromyces, Pichia* (e. g. *Pichia pastoris*), *Hansenula* (e. g. *Hansenula* polymorph), *Schwaniomyces, Schizosaccharomyces, Yarowia, Zygosaccharomyces* and the like. *Saccharomyces cerevisiae, S. carlsbergensis* and *K. lactis* are the most commonly used yeast hosts, and are convenient fungal hosts.

The term "higher eukaryote" refers to host cells derived from higher animals, such as mammals, reptiles, insects, and the like. Presently preferred higher eukaryote host cells are derived from Chinese hamster (e. g. CHO), monkey (e. g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, the 293TT cell line (Buck et al., 2004) and insectcell lines (e.g. *Spodoptera frugiperda*). The host cells may be provided in suspension or flask cultures, tissue cultures, organ cultures and the like. Alternatively the host cells may also be transgenic non-human animals.

The term "prokaryotes" refers to hosts such as *E. coli, Lactobacillus, Lactococcus, Salmonella, Streptococcus, Bacillus subtilis* or *Streptomyces*. Also these hosts are contemplated within the present invention.

The segment of the MSBI DNA encoding the desired sequence inserted into the vector sequence may be attached to a signal sequence. Said signal sequence may be that from a non-MSBI source, but particularly preferred constructs according to the present invention contain signal sequences appearing in the MSBI genome before the respective start points of the proteins.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. For vaccination of humans the avipox and Ankara Modified Virus (AMV) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral signaling gene promoter to drive the expression of heterologous genes. Different vectors as well as methods for the introduction of heterologous DNA into the desired site of baculovirus are available to the person skilled in the art for baculovirus expression. Also different signals for posttranslational modification recognized by insect cells are known in the art.

The present invention also relates to a polypeptide having an amino acid sequence encoded by an HCBI, MSBI, MSSI or CMI polynucleic acid as defined above, or a part or an analogue thereof being substantially similar and biologically equivalent.

The term "polypeptide" refers to a polymer of amino acids and does not refer to a specific length of the product. Thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring.

The polypeptides according to the present invention contain preferably at least 3, preferably 4 or 5 contiguous MSBI amino acids, 6 or 7 preferably however at least 8 contiguous MSBI amino acids, at least 10 or at least 15.

The polypeptides of the invention, and particularly the fragments, can be prepared by classical chemical synthesis. The synthesis can be carried out in homogeneous solution or in solid phase. The polypeptides according to this invention can also be prepared by means of recombinant DNA techniques. The present invention also relates to a method for production of a recombinant polypeptide as defined above, which may comprise: (a) transformation of an appropriate cellular host with a recombinant vector, in which a polynucleic acid or a part thereof as defined above has been inserted under the control of the appropriate regulatory elements, (b) culturing said transformed cellular host under conditions enabling the expression of said insert, and (c) harvesting said polypeptide.

The present invention also relates to an antibody raised upon immunization with at least one polypeptide as defined above, with said antibody being specifically reactive with any of said polypeptides, and with said antibody being preferably a monoclonal antibody. The term "antibody", preferably, relates to antibodies which consist essentially of pooled monoclonal antibodies with different epitopic specificities, as well as distinct monoclonal antibody preparations. Monoclonal antibodies are made from an antigen containing, e.g., a polypeptide encoded by a MSBI polynucleic acid of the invention or a fragment thereof by methods well known to those skilled in the art. As used herein, the term "antibody" (Ab) or "monoclonal antibody" (Mab) is meant to include intact molecules as well as antibody fragments (such as, for example, Fab and F(ab') 2 fragments) which are capable of specifically binding to protein. Fab and F(ab')2 fragments lack the Fc fragment of intact antibody, clear more rapidly from the circulation, and may have less non-specific tissue binding than an intact antibody. Thus, these fragments are preferred, as well as the products of a FAB or other immunoglobulin expression library. Moreover, antibodies useful for the purposes of the present invention include chimerical, single chain, and humanized antibodies.

The present invention also relates to diagnostic and therapeutic approaches using cell-mediated immune responses.

Preferably, the antibody or antigen binding fragment thereof carries a detectable label. The antibody/fragment can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The present invention also relates to a diagnostic kit for use in determining the presence of an HCBI, MSBI or CMI polynucleic acid or polypeptide of the invention, said kit which may comprise a primer, a probe, and/or an antibody of the invention. Said kit may have any format well known to the person skilled in the art, e.g. can be an ELISA-based kit.

The present invention also relates to a method for the detection of an, MSBI polynucleic acid according to the invention present in a biological sample, which may comprise: (a) optionally extracting sample polynucleic acid, (b) amplifying the polynucleic acid as described above with at least one primer as defined above, optionally a labelled primer, and (c) detecting the amplified polynucleic acids.

The term "polynucleic acid" can also be referred to as analyte strand and corresponds to a single- or double-stranded polynucleic acid molecule.

The term "labelled" refers to the use of labelled nucleic acids. This may include the use of labelled nucleotides incorporated during the polymerase step of the amplification or labelled primers, or by any other method known to the person skilled in the art.

The present invention also relates to a method for the detection of a MSBI polynucleic acid according to the invention present in a biological sample, which may comprise: (a) optionally extracting sample polynucleic acid, (b) hybridizing the polynucleic acid as described above with at least one probe as defined above, and (c) detecting the hybridized polynucleic acids.

The hybridization and washing conditions are to be understood as stringent and are generally known in the art. However, according to the hybridization solution (SSC, SSPE, etc.), these probes should be hybridized at their appropriate temperature in order to attain sufficient specificity.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions.

Suitable assay methods for purposes of the present invention to detect hybrids formed between the oligonucleotide probes and the MSBI polynucleic acid sequences in a sample may comprise any of the assay formats known in the art, such as the conventional dot-blot format, sandwich hybridization or reverse hybridization. For example, the detection can be accomplished using a dot blot format, the signaling amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the signaling oligonucleotide probes are bound to a solid support and exposed to the labelled sample under appropriate stringent hybridization and subsequent washing conditions. It is to be understood that also any other assay method which relies on the formation of a hybrid between the polynucleic acids of the sample and the oligonucleotide probes according to the present invention may be used.

The present invention also relates to a method for detecting a polypeptide encoded by a MSBI polynucleic acid of the present invention or an antibody against said polypeptide present in a biological sample, which may comprise: (a) contacting the biological sample for the presence of such polypeptide or antibody as defined above, and (b) detecting the immunological complex formed between said antibody and said polypeptide.

The immunoassay methods according to the present invention may utilize antigens from different domains of the new and unique polypeptide sequences of the present invention. It is within the scope of the invention to use for instance single or specific oligomeric antigens, dimeric antigens, as well as combinations of single or specific oligomeric antigens. The MSBI antigens of the present invention may be employed in virtually any assay format that employs a known antigen to detect antibodies or cell-mediated immune responses. Thus, the present invention also encompasses the detection of cell mediated immune responses against MSBI antigens and the application of therapeutic interferences based on cell-mediated immune responses against MSBI antigens.

Of course, an assay format that denatures the MSBI conformational epitope should be avoided or adapted. A common feature of all of these assays is that the antigen is contacted with the body component suspected of containing MSBI antibodies under conditions that permit the antigen to bind to any such antibody present in the component. Such conditions will typically be physiologic temperature, pH and ionic strength using an excess of antigen. The incubation of the antigen with the specimen is followed by detection of immune complexes which may comprise the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e. g., in membrane or microtiter well form), polyvinyl chloride (e. g., in sheets or microtiter wells), polystyrene latex (e. g., in beads or microtiter plates, polyvinylidine fluoride (known as Immunolon), diazotized paper, nylon membranes, activated beads, and Protein A beads. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of anti-MSBI antibodies in the antibody-antigen complexes is directly monitored. This may be accomplished by determining whether (labelled) anti-xenogeneic (e. g. anti-human) antibodies which recognize an epitope on anti-MSBI antibodies will bind due to complex formation. In a competitive format, the amount of MSBI antibodies in the sample is deduced by monitoring the competitive effect on the binding of a known amount of labelled antibody (or other competing ligand) in the complex.

Complexes formed which may comprise anti-MSBI antibody (or in the case of competitive assays, the amount of competing antibody) are detected by any of a number of known techniques, depending on the format. For example, unlabeled MSBI antibodies in the complex may be detected using a conjugate of anti-xenogeneic Ig complexed with a label (e. g. an enzyme label).

In an immunoprecipitation or agglutination assay format the reaction between the MSBI antigens and the antibody forms a network that precipitates from the solution or suspension and forms a visible layer or film of precipitate. If no anti-MSBI, antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen/antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin.

The above methods are useful for evaluating the risk of developing diseases like cancer or an autoimmune disease due to the deleterious effects of the presence of a subgenomic MSBI polynucleotide sequence by itself or linked to a particular host gene or gene fragment within the patient's cells and allow taking appropriate counter measures.

Thus, the present invention also relates to an antisense oligonucleotide or iRNA specific for the MSBI virus polynucleic acid of the invention.

The generation of suitable antisense oligonucleotides or iRNAs includes determination of a site or sites within the MSBI polynucleic acid for the antisense interaction to occur such that the desired effect, e.g., inhibition of expression of the polypeptide, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect. In the context of this invention, "hybridization" means hydrogen bonding, which may be Watson-Crick, Hoogsteen or reversed Hoogsteen hydrogen bonding, between complementary nucleoside or nucleotide bases. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

"Oligonucleotide" (in particular in the context of antisense compounds) refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention may comprise from about 8 to about 50 nucleobases (i.e. from about 8 to about 50 linked nucleosides). Particularly preferred antisense compounds are antisense oligonucleotides, even more preferably those which may comprise from about 15 to about 25 nucleobases. Antisense compounds include ribozymes, external guide sequences (EGS), oligonucleotides (oligozymes), and other short catalytic RNAs or catalytic oligonucleotides which hybridize to the target nucleic acid and inhibit its expression. The antisense compounds also include an iRNA which may comprise a sense sequence and an antisense sequence, wherein the sense and antisense sequences form an RNA duplex and wherein the antisense sequence may comprise a nucleotide sequence sufficiently complementary to the nucleotide sequence of a MSBI polynucleic acid of the present invention.

Alternatively, the invention provides a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, adeno-associated virus, herpes simplex virus, vaccinia, or, an RNA virus such as a retrovirus. Preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific.

This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957. The MSBI polynucleotide sequences of the invention may also serve as a suitable vector itself, either composed solely of rearranged MSBI sequences or of chimeric MSBI host cell DNA sequences. In addition, the nucleotide sequences of the invention may be used for the construction of artificial chromosomes.

In order to achieve expression only in the target organ, the DNA sequences for transcription of the antisense oligonucleotides can be linked to a tissue specific promoter and used for gene therapy. Such promoters are well known to those skilled in the art.

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage.

A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Modified oligonucleotides may also contain one or more substituted or modified sugar moieties. Preferred oligonucleotides may comprise one of the following at the 2' position: OH; F; 0-, S-, or N-alkyl; 0-, S-, or N-alkenyl; 0-, S- or N-alkynyl; or 0-alkyl-0-alkyl, wherein the alkyl, alkenyl and alkynyl may be substituted or unsubstituted $C_1$ to $C_{10}$ alkyl or $C_2$ to $C_{10}$ alkenyl and alkynyl. A particularly preferred modified sugar moiety is a 2'-O-methoxyethyl sugar moiety.

Antisense-oligonucleotides of the invention may also include nucleobase modifications or substitutions. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine etc., with 5-methylcytosine substitutions being preferred since these modifications have been shown to increase nucleic acid duplex stability.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, a thiocholesterol, an aliphatic chain, e.g., dodecandiol or undecyl residues, a phospholipid, a polyamine or a polyethylene glycol chain, or signaling acetic acid, a palmityl moiety, or an octadecylamine or hexylamino-carbonyl-oxycholesterol moiety.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, Rnase H is a cellular endonuclease which cleaves the RNA strand of an RNA:DNA duplex. Activation of Rnase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The present invention also relates to a pharmaceutical composition which may comprise an antibody or antisense oligonucleotide of the invention and a suitable excipient, diluent or carrier.

Preferably, in a pharmaceutical composition, such compound as described above is combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose.

An "effective dose" refers to an amount of the active ingredient that is sufficient to prevent the disease or to affect the course and the severity of the disease, leading to the reduction or remission of such pathology. An "effective dose" useful for treating and/or preventing these diseases or disorders may be determined using methods known to one skilled in the art.

Administration of the suitable compositions may be effected by different ways, e.g. by intravenous, intraperitoneal, oral, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

In a preferred embodiment of the present invention, the disease that can be prevented/treated is cancer, preferably breast cancer, ovarian cancer, lung cancer, prostate cancer, pancreatic cancer, Hodgkin's disease, colorectal cancer or colon cancer or a disease of the CNS, preferably Alzheimer's disease or multiple sclerosis (MS), amyotrophic lateral sclerosis, Parkinson's disease, or transmissible spongiforme encephalopathies/Prion-linked diseases. In addition, due to a similarity of risk factors between MS and diabetes mellitus, the latter condition is also included. The terms "cancer" and "disease of the CNS" may also comprise early stages of said diseases.

The present invention also relates to a vaccine for immunizing a mammal against a MSBI infection, which may comprise at least one polypeptide or MSBI polynucleic acid as defined above or corresponding VLP (virus-like particle) or peptide/protein/DNA complexes, in a pharmaceutically acceptable carrier. It also involves molecular and immunological tests in animals (in particular cattle) and within their products (e.g. milk and dairy products).

It may also include small chemicals for targeted therapy derived from the analysis of structural components of these agents.

A "vaccine" is an immunogenic composition capable of eliciting protection against MSBI, whether partial or complete. A vaccine may also be useful for treatment of an already infected individual, in which case it is called a therapeutic vaccine.

The term "therapeutic" refers to a composition capable of treating MSBI, infection or diseases linked to this infection. The term "effective amount" refers to an amount of epitopebearing polypeptide sufficient to induce an immunogenic response in the individual to which it is administered, or to otherwise detectably immunoreact in its intended system (e. g., immunoassay). Preferably, the effective amount is sufficient to effect treatment, as defined above, The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. Effective amounts will be found within a relatively large, non-critical range. An appropriate effective amount can be readily determined using routine experimentation. Preferred ranges of proteins for prophylaxis of MSBI caused diseases are 0.01 to 100 µg/dose, preferably 0.1 to 50 µg/dose. Several doses may be needed per individual in order to achieve a sufficient immune response and subsequent protection against an MSBI infection and a MSBI linked disease, respectively.

Pharmaceutically acceptable carriers include any carrier that does not itself induce the production of antibodies harmful to the individual receiving the vaccine. Suitable carriers are typically large, slowly metabolized macromolecules such as proteins, polysaccharides, polylactic acids, polyglycolic acids, polymeric amino acids, and amino acid copolymers. Such carriers are well known to those of ordinary skill in the art.

Preferred adjuvants to enhance effectiveness of the composition include, but are not limited to: aluminium hydroxide (alum), N-acetyl-muramyl-L-threonyl-D-isoglutamine (thr-MDP) as found in U.S. Pat. No. 4,606,918, N-acetylnormuramyl-L-alanyl-D-isoglutamine (nor-MDP), N-acetylmuramyl-L-alanyl-D-isoglutaminyl-L-alanine-2-(1'-2'-dipalmitoyl sn-signalin-3 hydroxy-phosphoryloxy)-ethylamine (MTP-PE) and RIBI, which contains three components extracted from bacteria, monophosphoryl lipid A, trehalose dimycolate, and cell wall Skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, M A) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions. Solid forms suitable for solution in, or suspension in, liquid vehicles prior to injection may also be prepared. The preparation also may be emulsified or encapsulated in liposomes for enhanced adjuvant effect. The proteins may also be incorporated into Immune Stimulating Complexes together with saponins, for example Quil A (ISCOMS).

Immunogenic compositions used as vaccines may comprise a "sufficient amount" or "an immunologically effective amount" of the proteins of the present invention, as well as any other of the above mentioned components, as needed. "Immunologically effective amount" means that the administration of that amount to an individual, either in a single dose or as part of a series, is effective for treatment, as defined above. This amount varies depending upon the health and physical condition of the individual to be treated, the capacity of the individual's immune system to synthesize antibodies, the degree of protection desired, the formulation of the vaccine, the treating doctor's assessment of the medical situation, and other relevant factors.

It is expected that the amount will fall in a relatively broad range that can be determined through routine trials. Usually the amount will vary from 0.01 to 1000 µg/dose, more particularly from 0.1-100 µg/dose.

The following examples are intended to illustrate, but not to limit the invention. While such examples are typical of those that might be used, other methods known to those skilled in the art may alternatively be utilized.

Example 1

Material and Methods (A) Fractionation of Bovine Sera on Density-Sedimentation Gradients with Subsequent Cloning Initially, pools of 5 sera from a total of 120 bovine sera were subjected to Optiprep-(iodixanol)-density gradient ultracentrifugation after prior benzonase treatment to remove all free DNA and RNA (Buck et al., 2005). Protein-associated DNA was extracted from fractions (Qiagen PCR Purification Kit) and 1 µl DNA/fraction subjected to RCA (rolling circle amplification) in a solution of 50 µM Exo-resistant random primers (Thermo Scientific), 3.2 µmol each dNTPs (Takara) and 10 U phi29 polymerase (Biolabs). Restriction digested products (EcoR1 or BamH1) were separated by agarose gel electrophoresis, eluted and cloned into vector pUC19 prior to sequencing.

(B) Rolling Circle Amplification of DNA Extracted from Sera, Cow Milk or Brain Tissue:

DNA was extracted by phenol-chloroform from milk and post mortem brain tissue and sera from MS patients. DNA from all serum samples was extracted using the High Pure Viral Nucleic Acid amplification) with random Kit (Roche). RCA (rolling circle primers on DNA from protein associated sequencing primers fractions, restriction of resulting fragments designed either digestion, cloning and (refer above). Abutting on the individual isolated DNA sequences, as well as on the replication genes of Sphinx1.76 or Sphinx2.36 and used in inverted PCR on RCA amplified DNA from single bovine sera and cow milk, as well as sera from multiple sclerosis patients and post mortem multiple sclerosis brain samples.

Example 2

Concept for the Pathogenesis of Multiple Sclerosis: Isolation of Circular DNA Molecules (Bovine Agents) from Bovine Serum, Cow Milk and Multiple Sclerosis Brain The epidemiology of colon cancer suggested the involvement of an infectious factor present in red meat derived from cattle of European/Asian descent (zur Hausen, 2012; zur Hausen, 2015) and cow milk consumption has been suspected to play a role in multiple sclerosis. In attempts to isolate these putative factors, sera from 120 healthy 5-year old cows were obtained from the Veterinary Faculty of the University of Leipzig and analyzed for the presence of circular episomal DNA Since the first isolates HCBI6.252 (Healthy Cattle Blood Isolate) (2522 bp) and HCBI6.159 (1591 bp) revealed a distant relationship to DNA related to sequences found in brain lesions of animals linked to prion-associated conditions (Manuelidis, 2011). The inventors concomitantly analysed 8 sera (from patients in relapse), 2 CSF and 1 PBMC from MS patients, as well as 12 biopsies from post mortem brain tissue for Sphinx-related sequences. Two circular DNA molecules related to Sphinx1.76 (1758 bp acc no. HQ444404) were isolated from one MS brain sample—MSBI1.176 Multiple Sclerosis Brain Isolate) (1766 bp) and MS2.176 (1766 bp). Since there is an elevated MS risk after cow milk consumption, the inventors investigated commercially available pasteurized milk for the presence of related DNA. Indeed, they isolated episomal single-stranded DNA molecules from all 4 milk samples (CMI1.252 (Cow Milk Isolate), CMI2.214, CMI3.168 and CMI4.158) (HCBI6.252 and CMI1.252 are near identical). This was taken as an indication that milk excretion of these agents is indeed occurring.

The inventors used 2 primer pairs designed on Sphinx1.76 for inverted PCR on all human and bovine samples. These primers pairs were: forward 5'-GGATTAATGCCAAT-GATCC-3' (nt 721-739) (SEQ ID NO:23), reverse 5'-CGAGAGAAACAGGCAAAG-3' (nt703-720) SEQ ID NO:28) and forward 5'-GAGGACGAATTAATATTA-CAAGTC-3' (nt868-891) (SEQ ID NO:26), reverse TTAC-CAAGAAAAGCGAGAAC-3' (nt848-867) (SEQ ID NO:27). The resulting sequences are all distantly similar (ranging from 79%-98%) to the Sphinx1.76 isolate. MSBI1.176 is 98% identical to Sphinx1.76, but the nature (patterns) of the single sequence differences are such that these can be regarded as two separate agents. As the Sphinx1.76 construct was not available in the inventor's laboratory, it could not have resulted from laboratory contamination. The inventors isolated a second very distantly Sphinx1.76-related (but identical in size) circular DNA molecule MSBI2.176 from the same brain biopsy.

Figure 6:
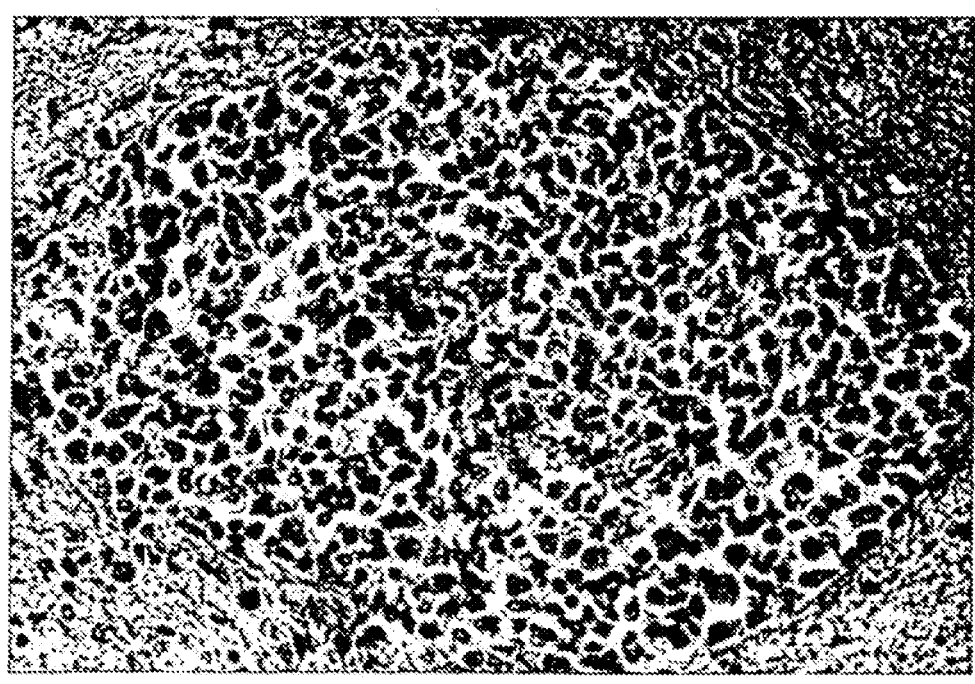
Figure 7:
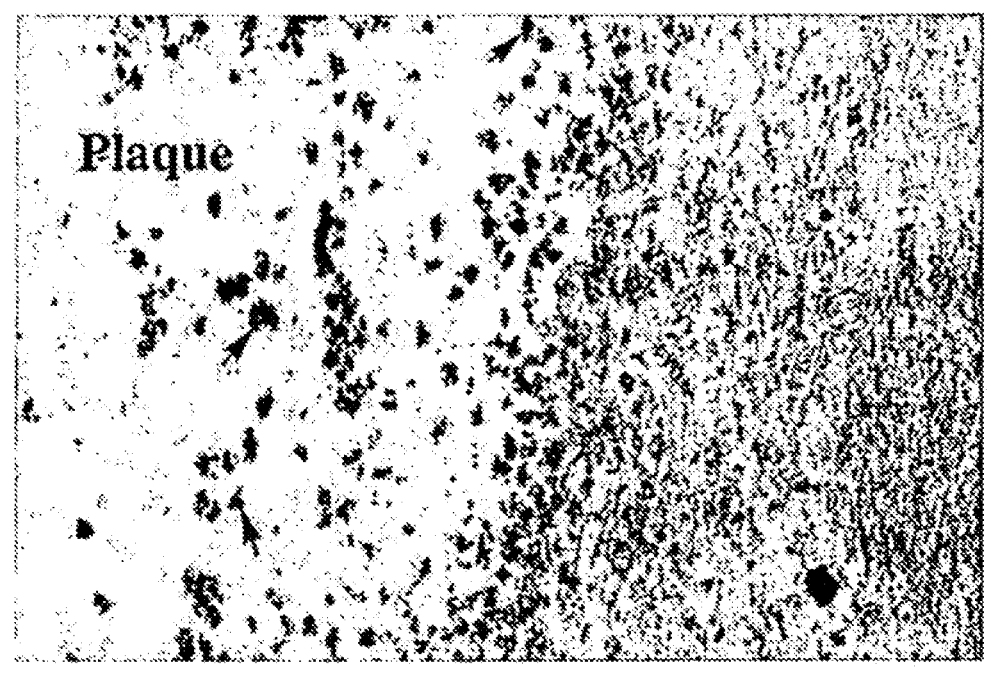

The large ORFs of the isolate of group 1 encode for replication protein (ProtSweep, del Val et al., 2007) sharing high similarity between them. Another common feature is the presence of iteron-like tandem repeats (3×22 nt plus 17/18 nt of the repeat in each isolate). Alignment of this repeat region indicates only single nucleotide variation in the core (FIG. 6). These iteron-like repeats may constitute binding sites for Rep proteins (Chattoraj, 2000, Dziewit et al., 2013).

Nucleotide sequence accession number: The complete sequences of 8 isolates have been deposited in the EMBL Databank under the acc. No.:

| | |
|---|---|
| MSBI1.176 | Acc no. LK931491 |
| MSBI2.176 | Acc no. LK931492 |

In this context, diseases of the CNS (e.g. Multiple sclerosis MS, amyotrophic lateral sclerosis, transmissible spongiforme encephalopathies/Prion-linked diseases, Parkinson's disease, Alzheimer disease) are also highly interesting since the similar sequences described by Manuelidis are primarily found in the CNS.

The presence of presumably infectious agents and their nucleic acids in the serum of healthy cows should imply that the same particles are also present in red meat.

The inventors isolated 13 novel single-stranded DNA molecules from cattle serum and milk and MS brain tissue and sera. These isolates are grouped in 4 groups according to their sequence similarity to the Sphinx1.76 genome (group 1), Sphinx2.36 genome (group 2), are similarity to (group 2), myco-like Gemycircularviruses (group 3) and *Psychrobacter* spp. Plasmid (group 4). The main feature of all the sequences is the presence of a replication-associated protein encoding ORF.

All the isolates are presumably single-stranded DNA because of the bias of RCA towards amplification of single-stranded DNA (del Solar et al., 1998). A taxonomic classification of the isolates is, at this stage, not possible.

Infection of human cells by such agents should evoke a strong immune reaction, quite distinct from human TT viruses, where reasonable evidence for vertical transmission has been obtained (reviewed in zur Hausen and de Villiers, 2014). This could explain the high susceptibility to environmental factors for MS development during the first 15 years of life: primary infection may initially lead to rounds of replication and spreading of BMF probably via blood cells, eventually resulting in latent brain cell infection. This initial infection should induce an immune response, probably neutralizing the agent in subsequent rounds of infection prior to entry of the brain. The isolates reported here seem to represent excellent candidates for the postulated bovine milk factor (BMF).

Figure 2:
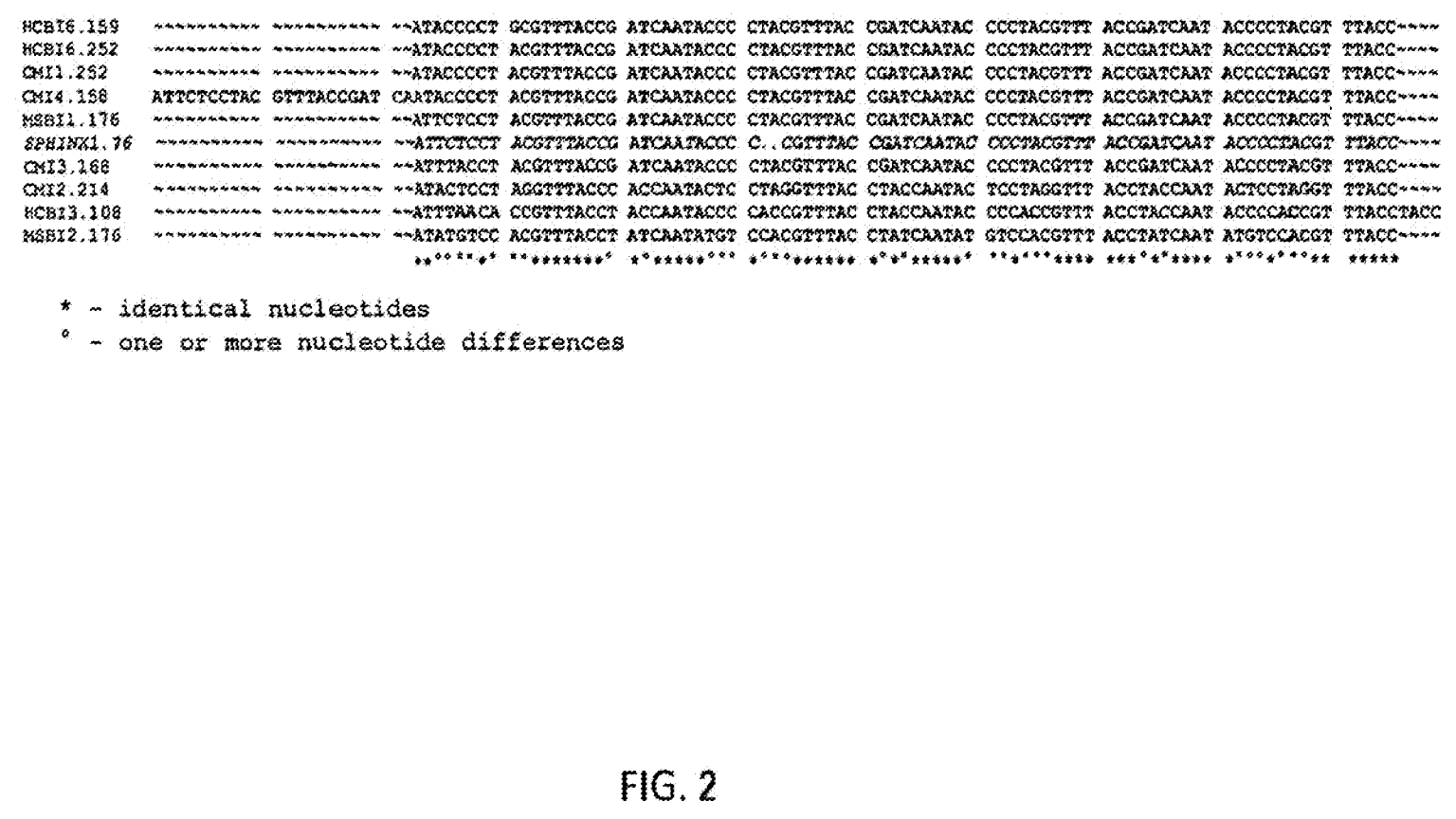

A high variability in size was noted in group 1. The circular isolate HCBI6.159 seem to have evolved from HCBI6.252 through deletion of 931 nucleotides from the latter. The isolates all possess a replication gene and have an iteron-like repeat region in common (Dziewit et al., 2013). Alignment of this region between 8 isolates and Sphinx1.76 reveals a central identical core (FIG. 2). Group 2 and 4 isolates do not have repeat regions.

The "Sphinx" sequences (Manuehdis, 2011) show high homologies to plasmid sequences of the bacterium *Acinetobacter* (Vallenet et al., 2008; Longkumer et al., 2013). The sequences obtained in the present invention also exhibit striking homologies to the corresponding plasmid sequences. Although a large number of plasmids have been isolated and sequenced from *Acinetobacter*, thus far none of them corresponded exactly to the bovine and human sequences reported in this invention. Interestingly, a group of scientists in the UK published serological data over a period of years pointing to an increased selective formation of antibodies against *Acinetobacter* proteins but not against other bacterial signalin obtained from patients suffering from multiple sclerosis (see review article: Ebringer et al., 2012). These results could not be confirmed by the group of Chapman (Chapman et al., 2005). However, it has to be stressed that the group of Chapman used a different strain of *Acinetobacter* (*Acinetobacter calcoaceticus*). Unequivocal results were obtained by the group of Ebringer for three strains of *Acinetobacter* (*Acinetobacter lwoffii*, A. radioesistens and a specific isolate, A. 11171). However, the results obtained for *A. junii* 17908 were less impressive and significant reactivity was hardly detectable (Hughes et al., 2001). These results suggest that we are dealing with strain-specific reactivities wherein this sero-reactivity is due to strain-specific plasmids exhibiting homologies to the DNA sequences obtained in the present invention.

The isolate MSSI1.162 (group 4) has similarity to a plasmid of the *Psychrobacter* spp. *Pyschrobacter* species have been considered as an opportunistic human pathogen (Caspar et al., 2013) and has been isolated from a case of meningitis (Lloyd-Puryear et al., 1991). These bacteria have repeatedly been reported as contaminants during and after cold-storage of meat (de Filippis et al., 2013) and were frequently isolated from milk and a variety of cheeses (Coton et al., 2012).

It is of interest to note that Manuelidis reported two "Sphinx-structures", labeled as "large" (2.36) and "small" (1.76) Sphinx. Although most of the present sequences substantially differed from her isolates, the inventors also obtained large and small Sphinx-like sequences from the same probes. Circular HCBI6.159 seems to have evolved from HCBI6.252 through a deletion of 931 nucleotides from the latter. It cannot be excluded that the other larger isolates may have smaller counterparts which were not isolated. It remains, however, to be determined whether the two structures found here persist within the same protein coat or complement each other.

The isolation of DNA of similar, in part even identical single-stranded circular nucleic acids from cattle sera, commercially available cow milk and florid MS tissues argues in favour of the concept outlined above.

REFERENCES

Buck C B, Pastrana D V, Lowy D R, Schiller J T. Efficient intracellular assembly of papillomaviral vectors. J. Virol. 2004; 78:751-757.

Chapman M D, Hughes L E, Wilson C D, Namnyak S, Thompson E J, Giovannoni G. No evidence for production of intrathecal immunoglobulin G against *Acineto-bacter* or *Pseudomonas* in multiple sclerosis. Eur Neurol. 2005; 53(1):27-31.

De Villiers E M, Borkosky S S, Kimmel R, Gunst K, and Fei J W. (2011) The diversity of Torque teno viruses: In vitro replication leads to the formation of additional replication-competent subviral Molecules. J Virol 2011; 85(14): 7284-7295

Ebringer A, Hughes L, Rashid T, Wilson C. *Acinetobacter* Immune Responses in Multiple Sclerosis: Etiopathogenetic Role and Its Possible Use as a Diagnostic Marker. Arch Neurol. 2005; 62:33-36.

Ebringer A, Rashid T, Wilson C. The role of *Acinetobacter* in the pathogenesis of multiple sclerosis examined by using Popper sequences. Med Hypotheses. 2012; 78(6): 763-769.

Hughes, L. E., Bonell, S., Natt, R. S., Wilson, C., Tiwana, H., Ebringer, A., Cunningham, P., Chamoun, V., Thomp-son, E. J., Croker, J., and Vowles, J. Antibody responses to *Acinetobacter* spp. And *Pseudomonas* signaling in multiple sclerosis: prospects for diagnosis using the myelin-*Acinetobacter*-neurofilament antibody index. Clin. Diagn. Laboratory Immunol. 2001; 8:1181-1188.

Longkumer T, Kamireddy S, Muthyala V R, Akbarpasha S, Pitchika G K, Kodetham G, Ayaluru M, Siddavattam D. Scientific Reports 2013; 3:2240.

Manuelidis L. Nuclease resistant circular DNAs copurify with infectivity in scrapie and CJD. J. Neurovirol. 2011; 17:131-145.

Wold, M S. Replication protein A: heterotrimeric, single-stranded DNA-binding protein required for eukaryotic DNA metabolism. Ann. Review Biochem. 1997; 66:61-92

Vallenet D, Nordmann P, Barbe V, Poirel L, Mangenot S, Bataille E, Dossat C, Gas S, Kreimeyer A, Lenoble P, Oztas S, Poulain J, Segurens B, Robert C, Abergel C, Claverie J-M, Raoult D, Medigue C, Weissenbach J, Cruveiller S. Comparative analysis of Acinetobacters: three genomes for three lifestyles. PloS One 2008; 3(3): e1805-e1805.

Xu B, Zhi N, Hu G, Wan Z, Zheng X, Liu X, Wong S, Kajigaya S, Zhao K, Mao Q, Young N S. Hybrid DNA virus in Chinese patients with seronegative hepatitis discovered by deep sequencing. Proc Natl Acad Sci USA. 2013; 110: 10264-9.

Zur Hausen H. Red meat consumption and cancer: Reasons to suspect involvement of bovine infectious factors in colorectal cancer. Int J Cancer 2012; 130:2475-2483.

Zur Hausen H., de Villiers, E.-M., Prenatal Infections with Subsequent Immune Tolerance could explain the Epidemiology of Common Childhood Cancers, World Cancer Report, IARC, Lyon, 2014, pp. 261-265.

Abdel-Hag N M, Asmar B I. Human herpes virus 6 (1-11-1V6) infection. Indian J Pediatr. 2004; 71: 89-96.

Agranoff B W, Goldberg D. Diet and the geographical distribution of multiple sclerosis. Lancet II 1974; 1061.

Alcalde-Cabero E, Almazan-Isla J, Garcia-Merino A, de Sa. J, de Pedro-Cuesta J. *Incidence of multiple sclerosis among European Economic Area populations, 1985-2009: the framework for monitoring.* BMC Neurol. 2013; 13: 58-80.

Alenda R, Alvarez-Lafuente R, Costa-Frossard L, Arroyo R, Mirete S, Alvarez-Cermeño J C, Villar L M. Identification of the major HHV-6 antigen recognized by cerebrospinal fluid IgG in multiple sclerosis. *Eur J Neurol.* 2014 Apr. 12. Doi: 10.1111/ene.12435.

Almohmeed Y H, Avenell A, Aucott L, Vickers M A. *Systematic review and meta-analysis of the sero-epidemiological association between Epstein Barr virus and multiple sclerosis.* PloS One. 2013; 8: e61110.

Angelini D F, Serafini B, Piras E, Severa M, Coccia E M, Rosicarelli B, Ruggieri S, Gasperini C, Buttari F, Centonze D, Mechelli R, Salvetti M, Borsellino G, Aloisi F, Battistini L. *Increased CD8+ T cell response to Epstein-Barr virus lytic antigens in the active phase of multiple sclerosis.* PloS Pathog. 2013; 9: e1003220.

Ascherio A, Munger K L, Liinemann J D. *The initiation and prevention of multiple sclerosis.* Nat Rev Neurol. 2012; 8: 602-12.

Ascherio A. Environmental factors in multiple sclerosis. Expert Rev. Neurother. 2013; 13 (12s) 3-9.

Ashtari F, Jamshidi F, Shoormasti R S, Pourpak Z, Akbari M. *Cow's milk allergy in multiple sclerosis patients.* J Res Med Sci. 2013; 18 (Suppl 1): S62-5.

Bager P, Nielsen N M, Bihrmann K, Frisch M, Wohlfart J, Koch-Henriksen N, Melbye M, Westergaard T *Sibship*

*characteristics and risk of multiple sclerosis: a nation-wide cohort study in Denmark.* Am J Epidemiol. 2006; 163: 1112-7.

Bantel-Schaal U, zur Hausen H. Adeno-associated viruses inhibit SV40 DNA amplification and replication of herpes simplex virus in SV40-transformed hamster cells. Virology 1988; 164: 64-74.

Banwell B, Bar-Or A, Cheung R, Kennedy J, Krupp L B, Becker D J, Dosch H M; Wadsworth Pediatric Multiple Sclerosis Study Group. Abnormal T-cell reactivities in childhood inflammatory demyelinating disease and type 1 diabetes. *Ann Neurol.* 2008; 63: 98-111.

Baranzini S E, Mudge J, van Velkinburgh J C, Khankhanian P, Khrebtukova I, Miller N A, Zhang L, Farmer A D, Bell C J, Kim R W, May G D, Woodward J E, Caillier S J, McElroy J P, Gomez R, Pando M J, Clendenen L E, Ganusova E E, Schilkey F D, Ramaraj T, Khan O A, Huntley J J, Luo S, Kwok P Y, Wu T D, Schroth G P, Oksenberg J R, Hauser S L, Kingsmore S F. Genome, epigenome and RNA sequences of monozygotic twins discordant for multiple sclerosis. *Nature.* 2010; 464: 1351-6.

Bauer G, Höfler P, zur Hausen H. *Epstein-Barr virus induction by a serum factor. I. Induction and cooperation with additional inducers.* Virology. 1982; 121: 184-94.

Bauer G, Götschl M, Höfler P. Tumor-promoting activity of Epstein-Barr-virus-inducing factor transforming growth factor type beta (EIF/TGF-beta) is due to the induction of irreversible transformation. *Int J Cancer.* 1991; 47: 881-8.

Ben Fredj N, Rotola A, Nefzi F, Chebel S, Rizzo R, Caselli E, Frih-Ayed M, Di Luca D, Aouni M. *Identification of human herpes viruses 1 to 8 in Tunisian multiple sclerosis patients and healthy blood donors.* J Neurovirol. 2012; 18:12-19.

Beretich B D, Beretich $T_M$. Explaining multiple sclerosis by ultraviolet exposure: a geospatial analysis. Mult Scler 2009; 15: 891-8.

Birkeland S A, Storm H H, Lamm L U, Barlow L, Blohmé I, Forsberg B, Eklund B, Fjeldborg O, Friedberg M, Frödin L, et al. *Cancer risk after renal transplantation in the Nordic countries,* 1964-1986. Int J Cancer. 1995 Jan. 17; 60(2):183-9.

Borkosky S S, Whitley C, Kopp-Schneider A, zur Hausen H, de Villiers E M. *Epstein-Barr virus stimulates torque teno virus replication: a possible relationship to multiple sclerosis.* PloS One. 2012; 7: e32160.

Brecht I, Weissbrich B, Braun J, Toyka K V, Weishaupt A, Buttmann M. *Intrathecal, polyspecific antiviral immune response in oligoclonal band negative multiple sclerosis.* PloS One. 2012; 7: e40431.

Buchanan R, Bonthius D J. Measles virus and associated central nervous system sequelae. *Semin Pediatr Neurol.* 2012; 19: 107-14.

Butcher P J, The distribution of multiple sclerosis in relation to the dairy industry and milk consumption. *N Z Med J.* 1976; 83: 427-30.

Butcher P J. Milk consumption and multiple sclerosis—an etiological hypothesis. *Med Hypotheses.* 1986; 19: 169-78.

Caserta M T, Mock D J, Dewhurst S. *Human herpes virus 6.* Clin Infect Dis. 2001; 33: 829-33. Review.

Christensen J C. *Multiple sclerosis: some epidemiological clues to etiology.* Acta Neurol Latinoam. 1975; 21: 66-85. Review.

Christensen T. *Human herpes viruses in MS.* Int MS J. 2007; 14: 41-7. Review.

Conradi S, Malzahn U, Paul F, Quill S, Harms L, Then Bergh F, Ditzenbach A, Georgi T, Heuschmann P, Rosche B. *Breastfeeding is associated with lower risk for multiple sclerosis.* Mult Scler. 2013; 19: 553-8.

Cusick M F, Libbey J E, Fujinami R S. Multiple sclerosis: autoimmunity and viruses: Curr. Opin. Rheumatol. 2013; 25: 496-501.

Décard BF, von Ahsen N, Grunwald T, Streit F, Stroet A, Niggemeier P, Schottstedt V, Riggert J, Gold R, Chan A. Low vitamin D and elevated immunoreactivity against Epstein-Barr virus before first clinical manifestation of multiple sclerosis. J Neurool Neurosurg Psychiatry. 2012; 83: 1170-3.

Dewhurst S. *Human herpes virus type 6 and human herpes virus type 7 infections of the central nervous system.* Herpes. 2004; 11 Suppl 2: 105A-111A. Review.

Disanto G, Morahan J M, Barnett M H, Giovannoni G, Ramagopalan S V. The evidence for a role of B cells in multiple sclerosis. Neurology 2012; 78: 823-32.

Engels E A, Biggar R J, Hall H I, Cross H, Crutchfield A, Finch J L, Grigg R, Hylton T, Pawlish K S, McNeel T S, Goedert J J. *Cancer risk in people infected with human immunodeficiency virus in the United States.* Int J Cancer. 2008; 123: 187-94.

Ferrò MT, Franciotta D, Prelle A, Bestetti A, Cinque P. *Active intrathecal herpes simplex virus type 1 (HSV-1) and human herpes virus-6 (HHV-6) infection at onset of multiple sclerosis.* J Neurovirol. 2012; 18: 437-4

Fotheringham J, Jacobson S. Human herpes virus 6 and multiple sclerosis: potential mechanisms for virus-induced disease. *Herpes* 2005; 12: 4-9.

Fraussen J, Vrolix K, Martinez-Martinez P, Losen M, De Baets M H, Stinissen P, Somers V. B cell characterization and reactivity analysis in multiple sclerosis. *Autoimmun Rev.* 2009; 8: 654-8.

Frolik C A, Dart L L, Meyers C A, Smith D M, Sporn M B. *Purification and initial characterization of a type beta transforming growth factor from human placenta.* Proc Natl Acad Sci USA. 1983; 80: 3676-80.

Gaitàn MI, Sati P, Inati S J, Reich D S. Initial investigation of the blood-barrier in MS lesions at 7 tesla. Mult Scler. 2013; 19: 1068-73.

Geeraedts F, Wilczak N, van Binnendijk R, De Keyser J. *Search for morbillivirus proteins in multiple sclerosis brain tissue.* Neuroreport. 2004; 19: 15: 27-32.

Grant W B. *Epidemiology of disease risks in relation to vitamin D insufficiency.* Prog Biophys Mol Biol. 2006; 92: 65-79.

Grinde B. Herpes viruses: latency and reactivation—viral strategies and host response. J Oral Microbiol. 2013; doi: 10.3402/jom.v510.22766.

Guggenmos J, Schubart A S, Ogg S, Andersson M, Olsson T, Mather I H, Linington C. Antibody cross-reactivity between myelin oligodendrocyte glycoprotein and the milk protein butyrophilin in multiple sclerosis. J. Immunol. 2004; 172: 661-8.

Hawkes C H, Giovannoni G, Keir G, Cunnington M, Thompson E J. *Seroprevalence of herpes simplex virus type 2 in multiple sclerosis.* Acta Neurol Scand. 2006; 114: 363-7.

Heilbronn R, BUrkle A, Stephan S, zur Hausen H. *The adeno-associated virus rep gene suppresses herpes simplex virus-induced DNA amplification.* J Virol. 1990a; 64: 3012-8.

Heilbronn R, Weller S K, zur Hausen H. *Herpes simplex virus type 1 mutants for the origin-binding protein induce*

*DNA amplification in the absence of viral replication.* Virology. 1990b; 179: 478-81.

Heilbronn R, Albrecht I, Stephan S, Burkle A, zur Hausen H. *Human cytomegalovirus induces JC virus DNA replication in human fibroblasts.* Proc Natl Acad Sci USA. 1993; 90: 11406-10.

Henle W, Henle G. Evidence for an etiologic relation of the Epstein-Barr virus to human malignancies. Laryngoscope. 1977; 87: 467-73.

Hollis B W, Roos B A, Draper H H, Lambert P W. *Vitamin D and its metabolites in human and bovine milk.* J Nutr. 1981; 111: 1240-8.

Holzmann C, Bauer I, Meyer P. Co-occurrence of multiple sclerosis and cancer in a BRCA1 positive family. *Eur J Med Genet.* 2013; 56: 577-9.

Hsiao F C, Tai A K, Deglon A, Sutkowski N, Longnecker R, Huber B T. *EBV LMP-2A employs a novel mechanism to transactivate the HERV K18 superantigen through its ITAM.* Virology. 2009; 385: 261-6.

Hu Knox K K, Brewer J H, Henry J M, Harrington D J, Carrigan D R. *Human herpes virus 6 and multiple sclerosis: systemic active infections in patients with early disease.* Clin Infect Dis. 2000; 31: 894-903.

Hyppönen E. *Vitamin D and increasing incidence of type 1 diabetes-evidence for an association?* Diabetes Obes Metab. 2010; 12: 737-43.

Isik S, Ozuguz U, Tutuncu Y A, Erden G, Berker D, Acar K, Aydin Y, Akbaba G, Helvaci N, Guler S. Serum transforming growth factor-beta levels in patients with vitamin D deficiency. *Eur J Intern Med.* 2012; 23: 93-7.

Ito I, Waku T, Aoki M, Abe R, Nagai Y, Watanabe T, Nakajima Y, Ohkido I, Yokoyama K, Miyachi H, Shimizu T, Murayama A, Kishimoto H, Nagasawa K, Yanagisawa J. A nonclassical vitamin D receptor pathway suppresses renal fibrosis. *Clin Invest.* 2013; 123: 4579-94.

James E, Dobson R, Kuhle J, Baker D, Giovannoni G, Ramagopalan S V. *The effect of vitamin D-related interventions on multiple sclerosis relapses: a meta-analysis.* Mult Scler. 2013; 19: 1571-9.

Kakalacheva K, Münz C, Lünemann JD. *Viral triggers of multiple sclerosis.* Biochim Biophys Acta. 2011; 1812: 132-40.

Karner W, Bauer G. Activation of a varicella-zoster virus-specific IgA response during acute Epstein-Barr virus infection. *J Med Virol.* 1994; 44: 258-62.

Koch-Henriksen N, Sorensen P S. *Why does the north-south gradient of incidence of multiple sclerosis seem to have disappeared on the northern hemisphere?* J Neurol Sci. 2011; 311: 58-63.

Koch-Henriksen N, Stenager E, Laursen B. *The use of epidemiological multiple sclerosis registers in research: the Danish MS Registry.* Acta Neurol Scand Suppl. 2012; 195: 7-12.

Kotzamani D, Panou T, Mastorodemos V, Tzagournissakis M, Nikolakaki H, Spanaki C, Plaitakis A. Rising incidence of multiple sclerosis in females associated with urbanization. *Neurology.* 2012; 78: 1728-35.

Kurtzke J F. Multiple sclerosis in time and space—geographic clues to cause. *J Neurovirol.* 2000; 6 Suppl 2: S134-40.

Kurtzke J F. *Epidemiology in multiple sclerosis: a pilgrim's progress.* Brain. 2013; 136: 2904-17.

Kuusisto H, Hyöty H, Kares S, Kinnunen E, Elovaara I. *Human herpes virus 6 and multiple sclerosis: a Finnish twin study.* Mult Scler. 2008; 14: 54-8.

Latif N, Rana F, Guthrie T. *Breast cancer and HIV in the era of highly active antiretroviral therapy: two case reports and review of the literature.* Breast J. 2011; 17: 87-92.

Lebrun C, Debouverie M, Vermersch P, Clavelou P, Rumbach L, de Seze J, Wiertlevski S, Defer G, Gout O, Berthier F, Danzon A. *Cancer risk and impact of disease-modifying treatments in patients with multiple sclerosis.* Mult Scler. 2008; 14: 399-405.

Lemire J M, Adams J S, Sakai R, Jordan S C. 1 alpha,25-dihydroxyvitamin D3 suppresses proliferation and immunoglobulin production by normal human peripheral blood mononuclear cells. J Clin Invest 1984; 74: 657-61.

Libbey J E, Cusick M F, Fujinami R S. Role of pathogens in multiple sclerosis. Intern Rev Immunol. Early Online 1-18, 2013; DOI: 10.3/08830185.2013.823422

Liu H, Fu Y, Li B, Yu X, Xie J, Cheng J, Ghabrial S A, Li G, Yi X, Jiang D. *Widespread horizontal gene transfer from circular single-stranded DNA viruses to eukaryotic genomes.* BMC Evol Biol. 2011 Sep. 26; 11:276. Doi: 10.1186/1471-2148-11-276.

Longkumer T, Kamireddy S, MuthyalaVR, Akbarpasha S, Pitchika G K, Kodetham G, Ayaluru M, Siddavattam D. *Acinetobacter* phage genome is similar to Sphinx 2.36, the circular DNA copurified with TSE infected particles. Sci Rep 2013; 3: 2240.doi: 10. 1038/srep02240.

Lucchinetti C, Brück W, Parisi J, Scheithauer B, Rodriguez M, Lassmann H. Heterogeneity of multiple sclerosis lesions: implications for the pathogenesis of demyelination. *Ann Neurol.* 2000; 47: 707-17.

Magliozzi R, Serafini B, Rosicarelli B, Chiapetta G, Veroni C., Reynolds R, Aloisi F. B-cell enrichment and Epstein-Barr virus infection in inflammatory cortical lesions in secondary progressive multiple sclerosis. J Neuropathol Exp Neurol 2013; 72: 29-41.

Malosse D, Perron H. Correlation analysis between bovine populations, other farm animals, house pets, and multiple sclerosis prevalence. *Neuroepidemiology.* 1993; 12: 15-27.

Marrie R A, Wolfson C. Multiple sclerosis and varicella zoster virus infection: a review. Epidemiol Infect. 2001; 127: 315-25. Review.

Matz B, Schlehofer J R, zur Hausen H. *Identification of a gene function of herpes simplex virus type 1 essential for amplification of simian virus 40 DNA sequences in transformed hamster cells.* Virology. 1984; 134: 328-37.

Mesliniene S, Ramrattan L, Goldings S, Sheikh-Ali M. Role of vitamin D in the onset, progression and severity of multiple sclerosis. Endocr Pract. 2013; 19: 129-36.

Metz I, Weigand S D, Popescu B F, Frischer J M, Parisi J E, Guo Y, Lassmann H, Bruck W, Lucchinetti C F. *Pathologic heterogeneity persists in early active multiple sclerosis lesions.* Ann Neurol. 2014 Apr. 26. Doi: 10.1002/ana.24163.

Midgard R, Glattre E, Gronning M, Riise T, Edland A, Nyland H. *Multiple sclerosis and cancer in Norway. A retrospective cohort study.* Acta Neurol Scand. 1996; 93: 411-5.

Mirandola P, Stefan A, Brambilla E, Campadelli-Fiume G, Grimaldi L M. *Absence of human herpes virus 6 and 7 from spinal fluid and serum of multiple sclerosis patients.* Neurology. 1999; 53: 1367-8.

Müller K, Heilmann C, Poulsen L K, Barington T, Bendtzen K. The role of monocytes and T cells in 1,25-dihydroxyvitamin D3 mediated inhibition of B cell function in vitro. Immunopharmacology 1991; 21: 121-8.

Munger K L, Chitnis, T, Frazier A L, Giovannucci E, Spiegelman D, Ascherio A. Dietary intake of vitamin D during adolescence and risk of multiple sclerosis. *J Neurol.* 2011a; 258: 479-85.

Munger K L, Levin L I, O'Reilly E J, Falk K I, Aschewrio A. Anti-Epstein-Barr virus antibodies as serological markers of multiple sclerosis: a prospective study among United States military personnel. Mult Scler 2011b; 17: 1185-93.

Murray T J. *An unusual occurrence of multiple sclerosis in a small rural community.* Can J Neurol Sci. 1976; 3: 163-6.

Nicoll M P, ProencaJT, Efstathiou S. The molecular basis of herpes simplex virus latency. FEMS Microbiol Rev. 2012; 36: 684-705.

Nielsen N M, Rostgaard K, Rasmussen S, Koch-Henriksen N, Storm H H, Melbye M, Hjalgrim H. *Cancer risk among patients with multiple sclerosis: a population-based register study.* Int J Cancer. 2006; 118: 979-84.

Nora-Krukle Z, Chapenko S, Logina I, Millers A, Platkajis A, Murovska M. *Human herpes virus 6 and 7 reactivation and disease activity in multiple sclerosis.* Medicina (Kaunas). 2011; 47: 527-31.

Nordal H J, Vandvik B, Norrby E. *Multiple sclerosis: local synthesis of electrophoretically restricted measles, rubella, mumps and herpes simplex virus antibodies in the central nervous system.* Scand J Immunol. 1978; 7: 473-9.

O'Gorman C, Lin R, Stankovich J, Broadley S A, Modelling genetic susceptibility to multiple sclerosis with family data. *Neuroepidemiology.* 2013; 40: 1-12.

Ohara Y. *Multiple sclerosis and measles virusz.* Jpn J Infect Dis. 1999; 52: 198-200. Review.

Olival G S, Lima B M, Sumita L M, Serafim V, Fink M C, Nali L H, Romano C M, Thomaz R B, Cavenaghi V B, Tilbery C P, Penalva-de-Oliveira A C. *Multiple sclerosis and herpes virus interaction.* Arq Neuropsiquiatr. 2013; 71: 727-30.

Ongrádi J, Rajda C, Maródi CL, Csiszár A, Vecsei L. *A pilot study on the antibodies to HHV-6 variants and HHV-7 in CSF of MS patients.* J Neurovirol. 1999; 5: 529-32.

Opsahl M L, Kennedy P G *Investigating the presence of human herpes virus 7 and 8 in multiple sclerosis and normal control brain tissue.* J Neurol Sci. 2006; 240: 37-44.

Ordoñez G, Pineda B, Garcia-Navarrete R, Sotelo J. *Brief presence of varicella-zoster vral DNA in mononuclear cells during relapses of multiple sclerosis.* Arch Neurol. 2004; 61: 529-32.

Owens G P, Gilden D, Burgoon M P, Yu X, Bennett J L. *Viruses and multiple sclerosis.* Neuroscientist. 2011; 17: 659-76. Review.

Pakpoor J, Pakpoor J, Disanto G, Giovannoni G, Ramagopalan S V. *Cytomegalovirus and multiple sclerosis risk.* J Neurol. 2013; 260: 1658-60.

Petersen T, Møller-Larsen A, Ellermann-Eriksen S, Thiel S, Christensen T. *Effects of interferon-beta therapy on elements in the antiviral immune response towards the human herpes viruses EBV, HSV, and VZV, and to the human endogenous retroviruses HERV-H and HERV-W in multiple sclerosis.* J Neuroimmunol. 2012; 249: 105-8.

Pierrot-Deseilligny C, Souberbielle J C. Contribution of vitamin D insufficiency to the pathogenesis of multiple sclerosis. Ther Adv Neurol Disord. 2013; 6: 81-116.

Pisacane A, Impagliazzo N, Russo M, Valiani R, Mandarini A, Florio C, Vivo P. Breast feeding and multiple sclerosis. BMJ. 1994; 308: 1411-2.

Pohl D, Rostasy K, Jacobi C, Lange P, Nau R, Krone B, Hanefeld F. *Intrathecal antibody production against Epstein-Barr and other neurotropic viruses in pediatric and adult onset multiple sclerosis.* J Neurol. 2010; 257: 212-6.

Provvedini D M, Tsoukas C D, Deftos L J, Manolagas S C. 1 alpha,25-dihydroxyvitamin D3-binding macromolecules in human B lymphocytes: effects on immunoglobulin production. J Immunol 1986; 136: 2734-40.

Rall G F. *Measles virus 1998-2002: progress and controversy.* Annu Rev Microbiol. 2003; 57: 343-67. Review.

Rima B K, Duprex W P. *Molecular mechanisms of measles virus persistence.* Virus Res. 2005; 111: 132-47. Review.

Rosecrans R, Dohnal J C. Seasonal vitamin D changes and the impact on health risk assessment. Clin Biochem, 2014; pii: S0009-9120. Doi: 10.1016/j.clinbiochem.2014.02.004.

Ross R T. *The varicella-zoster virus and multiple sclerosis.* J Clin Epidemiol. 1998; 51: 533-5. Review.

Ruprecht K, Obojes K, Wengel V, Gronen F, Kim K S, Perron H, Schneider-Schaulies J, Rieckmann P. *Regulation of human endogenous retrovirus W protein expression by herpes simplex virus type implications for multiple sclerosis.* J Neurovirol. 2006; 12: 65-71.

Salzer J, Nyström M, Hallmans G, Steenlund H, Wadell G, Sundström P. Epstein-Barr virus antibodies biobank samples. Mult Scler. 2013; 19: 1587-91.

Sanders V, Felisan S, Waddell A, Tourtellotte W. Detection of herpesviridae in postmortem multiple sclerosis brain tissue and controls by polymerase chain reaction. J Neurovirol. 1996; 2: 249-58.

Schlehofer J R, Gissmann L, Matz B, zur Hausen H. *Herpes simplex virus-induced amplification of SV40 sequences in transformed Chinese hamster embryo cells.* Int J Cancer. 1983; 32: 99-103.

Schlehofer J R, zur Hausen H. *Adenovirus infection induces amplification of persistent viral DNA sequences (simian virus 40, hepatitis B virus, bovine papillomavirus) in human and rodent cells.* Virus Res. 1990; 17: 53-60.

Schmitt J, Schlehofer J R, Mergener K, Gissmann L, zur Hausen H. Amplification of bovine papillomavirus DNA by N-methyl-N'-nitro-N-nitrosoguanidine, ultraviolet irradiation, or infection with herpes simplex virus. Virology 1989; 172:73-81.

Scott F W. Cow milk and insulin-dependent diabetes mellitus: is there a relationship? Am J Clin Nutr. 1990; 51:489-491.

Sepcic J, Mesaros E, Materljan E, Sepic-Grahovac D. Nutritional factors and multiple sclerosis in Gorski Kotar, Croatia. *Neuroepidemiology.* 1993; 12: 234-40.

Simpson S Jr, Taylor B, Dwyer D E, Taylor J, Blizzard L, Ponsonby A L, Pittas F, Dwyer T, van der Mei I. *Anti-HHV-6 IgG titer significantly predicts subsequent relapse risk in multiple sclerosis.* Mult Scler. 2012; 18: 799-806.

Sotelo J, Corona T. *Varicella zoster virus and relapsing remitting multiple sclerosis.* Mult Scler Int. 2011; 2011: 214763.

Sun L M, Lin C L, Chung C J, Liang J A, Sung F C, Kao C H. Increased breast cancer risk for patients with multiple sclerosis: a nationwide population-based cohort study. *Eur J Neurol.* 2013; Sep. 19. Doi: 10.1111/ene.12267.

Sundqvist E, Bergström T, Daialhosein H, Nystrom M, Sundstrom P, Hillert J, Alfredsson L, Kockum I, Olsson T. *Cytomegalovirus seropositivity is negatively associated with multiple sclerosis.* Mult Scler. 2013 Sep. 2. [Epub ahead of print].

Sundström P, Juto P, Wadell G, Hallmans G, Svenningsson A, Nyström L, Dillner J, Forsgren L. *An altered immune response to Epstein-Barr virus in multiple sclerosis: a prospective study*. Neurology. 2004; 62: 2277-82.

Sutkowski N, Chen G, Calderon G, Huber B T. *Epstein-Barr virus latent membrane protein LMP-2A is sufficient for transactivation of the human endogenous retrovirus HERV-K18 superantigen*. J Virol. 2004; 78: 7852-60.

Svejgaard A. *The immunogenetics of multiple sclerosis*. Immunogenetics. 2008; 60: 275-86.

Tai A K, Luka J, Ablashi D, Huber B T. *HHV-6A infection induces expression of HERV-K18-encoded superantigen*. J Clin Virol. 2009; 46: 47-8.

Tan I L, van Schijndel R A, Pouwell P J, van Walderveen M A, Reichenbach J R, Manoliu R A, Barkhof F. MR venography of multiple sclerosis. AJNR Am Neuroradiol. 2000; 21: 1029-42.

Tarrats R, Ordoñez G, Rios C, Sotelo J. Varicella, ephemeral breastfeeding and eczema as risk factors for multiple sclerosis in Mexicans. *Acta Neurol Scand*. 2002; 105: 88-94.

Taus C, Pucci E, Cartechini E, Fie A, Giuliani G, Clementi M, Menzo S. *Absence of HHV-6 and HHV-7 in cerebro-spinal fluid in relapsing-remitting multiple sclerosis*. Acta Neurol Scand. 2000; 101: 224-8.

Turcanova V L, Bundgaard B, Hollsberg P. *Human herpes virus-6B induces expression of the human endogenous retrovirus K18-encoded superantigen*. J Clin Virol. 2009; 46: 15-9.

Virtanen J O, Jacobson S. *Viruses and multiple sclerosis*. CNS Neurol Disord Drug Targets. 2012; 11: 528-44. Review.

Warren T R. The increased prevalence of multiple sclerosis among people who were born and bred in areas where goitre is endemic. *Med Hypotheses*. 1984; 14: 111-4.

Waubant E, Mowry E M, Krupp L, Chitnis T, Yeh E A, Kuntz N, Ness J, Belman A, Milazzo M, Gorman M, Weinstock-Guttman B, Rodriguez M, James J A. *Antibody response to common viruses and human leukocyte antigen-DRB1 in pediatric multiple sclerosis*. Mult Scler. 2013; 19: 891-5.

Wikström J. *Studies on the clustering of multiple sclerosis in Finland*. Riv Patol Nery Ment. 1976; 97: 199-204.

Winer S, Astsaturov I, Cheung R K, Schrade K, Gunaratnam L, Wood D D, Moscarello M A, O'Connor P, McKerlie C, Becker D J, Dosch H M. T cells of multiple sclerosis patients target a common environmental peptide that causes encephalitis in mice. J Immunol. 2001; 166: 4751-6.

Wu H, Li T, Zeng M, Peng T. Herpes simplex virus type 1 infection activates the Epstein-Barr virus replicative cycle via a CREB-dependent mechanism. *Cell Microbiol*. 2012; 14: 546-59.

Yea C, Tellier R, Chong P, Westmacott G, Marrie R A, Bar-Or A, Banwell B; *Canadian Pediatric Demyelinating Disease Network*. Epstein-Barr virus in oral shedding of children with multiple sclerosis. Neurology. 2013; 81: 1392-9.

Zerr P, Vollath S, Palumbo-Zerr K, Tomcik M, Huang J, Distler A, Beyer C, Dees C, Gela K, Distler O, Schett G, Distler J H. Vitamin D receptor regulates TGF-β signaling in systemic sclerosis. *Ann Rheum Dis*. 2014 Jan. 21. Doi: 10.1136/annrheumdis-2013-204378.

Zur Hausen H. *Genital papillomavirus infections*. Prog Med Virol. 1985; 32: 15-21.

Zur Hausen, H. and de Villiers, E. M., Diary cattle serum and milk factors contributing to the risk of colon and breast cancers, Int. J. Cancer, 2015, Feb. 3 doi: 10.1002/ijc.29466

Zwart S R, Mehta S K, Ploutz-Snyder R, Bourbeau Y, Locke J P, Pierson D L, Smith S M. Response to vitamin D supplementation during Antarctic winter is related to BMI, and supplementation can mitigate Epstein-Barr virus reactivation. J Nutr. 2011; 141:692-7.

References (Examples 2-5)

Buck C B, Pastrana D V, Lowy D R, Schillier J T. 2005. Generation of HPV pseudovirions using transfection and their use in neutralization assays. Methods Mol Med 119: 445-462.

Caspar. Y, Recule C, Pouzol P, Lafeuillade B, Mallaret M, Mairin M, Croize J. *Psychrobacter arenosus* bacteremia after blood transfusion, France. Emerging Infectious Diseases 2013; 19: 1118-1120.

Coton M, Delbes-Paus C, Irlinger F, Desmasures N, Le Fleche A, Stahl V, Montel M C, Coton E. Diversity and assessment of potential risk factors of Gram-negative isolates associated with French cheeses. Food Microbiol. 2012; 29:88-98.

De Filippis F, La Storia A, Villiani F, Ercolini D. Exploring the sources of bacterial spoilers in beefsteaks by culture-independent high-throughput sequencing. PloS One 2013; 8:e70222.

Del Solar G, Giraldo R, Ruiz-Echevarria M J, Espinosa M, Diaz-Orejas R. Replication and control of circular bacterial plasmids. Microbiol Mol. Biol. Rev. 1998; 62:434-464.

De Villiers E M, Borkosky S S, Kimmel R, Gunst K, Fei J W. The diversity of torque teno viruses: in vitro replication leads to the formation of additional replication-competent subviral molecules. J Virol. 2011; 85: 7284-95.

De Villiers, E M, zur Hausen, H. Concept for the pathogenesis of multiple sclerosis (I): interaction of an amplifying virus and a helper-dependent bovine milk factor. (submitted)

Funk M, Gunst K, Lucansky V, Müller H, zur Hausen H, de Villiers E-M., Isolation of protein-associated circular DNA from healthy cattle serum, Genome Announcements, 2(4): e00846-14, 2014

Dziewit L, Cegielski A, Romaniuk K, Uhrynowski W, Szych A, Niesiobedzki P, Zmuda-Baranowska M J, Zdanowski M K, Bartosik D. *Plasmid diversity in arctic strains of Psychrobacter* spp. Extremophiles. 2013; 17: 433-44

Ebringer A, Rashid T, Wilson C. Bovine spongiform encephalopathy, multiple sclerosis, and creutzfeldt-jakob disease are probably autoimmune diseases evoked by *Acinetobacter* bacteria. Ann N Y Acad Sci. 2005; 1050: 417-28.

Lloyd-Puryear M, Wallace D, Baldwin T, Hollis D G. Meningitis caused by *Psychrobacter immobilis* in an infant. J Clin. Microbiol. 1991; 29: 2041-2042.

Liu H, Fu Y, Li B, Yu X, Xie J, Cheng J, Ghabrial S A, Li G, Yi X, Jiang D. Widespread horizontal gene transfer from circular single-stranded DNA viruses to eukaryotic genomes. BMC Evol Biol. 2011; 11: 276. Doi: 10.1186/1471-2148-11-276.

Longkumer T, Kamireddy S, MuthyalaVR, Akbarpasha S, Pitchika G K, Kodetham G, Ayaluru M, Siddavattam D. *Acinetobacter* phage genome is similar to Sphinx 2.36, the circular DNA copurified with TSE infected particles. Sci Rep 2013; 3: 2240.doi: 10.1038/srep02240.

Martin D P, Biagini P, Lefeuvre P, Golden M, Roumagnac P, Varsani A. Recombination in eukaryotic single stranded DNA viruses. Viruses. 2011; 3: 1699-738.

Rosario K, Duffy S, Breitbart M. 2012a. A field guide to eukaryotic circular single-stranded DNA viruses: insights gained from metagenomics. Arch. Virol. 157: 1851-1871.

Rosario K, Dayaram A, Marinov M, Ware J, Kraberger S, Stainton D, Breitbart M, Varsani A. 2012b. Diverse circular ssDNA viruses discovered in dragonflies (Odonata: Epiprocta). J Gen. Viral. 93:2668-2681.

Sikorski A, Massaro M, Kraberger S, Young L M, Smalley D, Martin D P, Varsani A. 2013. Novel myco-like DNA viruses discovered in the faecal matter of various animals. Virus Res. 177:209-216.

Zur Hausen H, de Villiers E M. Prenatal Infections with Subsequent Immune Tolerance Could Explain the Epidemiology of Common Childhood Cancers. *World Cancer Report* 2014, IARC Lyon, pp 261-265.

De Villiers E-M, zur Hausen H. Concept for the pathogenesis of multiple sclerosis (I): Interaction of an amplifying virus and a helper-dependent bovine milk factor. (submitted).

Del Val C, Ernst P, Falkenhahn M, Fladerer C, Glatting K H, Suhai S, Hotz-Wagenblatt A. 2007. ProtSweep, 2Dsweep and DomainSweep: protein analysis suite at DKFZ. Nucleic Acids Res. 35 (Web Server issue):W444-450.

Chattoraj D K. 2000. Control of plasmid DNA replication by iterons: no longer paradoxical. Mol. Microbiol. 37: 467-476.

Zur Hausen H. 2001. Proliferation-inducing viruses in non-permissive systems as possible causes of human cancers. Lancet 357: 381-384.

Whitley C, Gunst K, Müller H, Funk M, zur Hausen H, de Villiers E-M., Novel replication-competent circular DNA molecules from healthy cattle serum, milk and multiple sclerosis-affected human brain tissue, Genome Announcements 2(4): e00849-14, 2014.

Lamberto I, Gunst K, Müller H, zur Hausen H, de Villiers E-M. Mycovirus-like DNA virus sequences from cattle serum, human brain and serum from multiple sclerosis patients, Genome Announcements 2(4): e00848-14, 2014

Gunst K, zur Hausen H, de Villiers E-M., Isolation of bacterial plasmid-related replication-associated circular DNA from serum sample of a multiple sclerosis patient, Genome announcement 2(4), e00847-14, 2014

The invention is further described by the following numbered paragraphs:

1. An HCBI, MSBI, MSSI or CMI polynucleic acid comprising:
   (a) a nucleotide sequence depicted in any one of FIGS. 1A to 4D;
   (b) a nucleotide sequence having at least 90% identity to a nucleotide sequence of (a);
   (c) a fragment of a nucleotide sequence of (a) or (b);
   (d) a nucleotide sequence being complementary to a nucleotide sequence of (a), (b) or (c); or
   (e) a nucleotide sequence which is redundant as a result of the degeneracy of the genetic code compared to any of the above-given nucleotide sequences.

2. An oligonucleotide primer comprising part of an HCBI, MSBI, MSSI or CMI polynucleic acid of paragraph 1, said primer being capable of acting as primer for specifically sequencing or specifically amplifying the nucleic acid of a certain HCBI, MSBI, MSSI or CMI isolate containing a nucleotide sequence in paragraph 1.

3. An oligonucleotide probe comprising part of an HCBI, MSBI, MSSI or CMI polynucleic acid of paragraph 1, said probe being capable of acting as a hybridization probe for specific detection of the nucleic acid of a certain HCBI, MSBI, MSSI or CMI isolate containing a nucleotide sequence of paragaph 1.

4. An expression vector comprising an HCBI, MSBI, MSSI or CMI polynucleic acid of any one of paragraphs 1 to 3 operably linked to prokaryotic, eukaryotic or viral transcription and translation control elements.

5. A host cell transformed or modified with an expression vector according to paragraph 4.

6. A polypeptide being encoded by an HCBI, MSBI, MSSI or CMI polynucleic acid of paragraph 1.

7. An antibody or antigen binding fragment thereof specifically binding to a polypeptide of paragraph 6.

8. Use of a primer according to paragraph 2, a probe according to paragraph 3, a polypeptide of paragraph 6, or an antibody or fragment thereof according to paragraph 7 for the preparation of a diagnostic composition for the diagnosis of a predisposition or an early stage of cancer, a disease of the CNS or diabetes.

9. Use according to paragraph 8, wherein the cancer is breast cancer, ovarian cancer, lung cancer, prostate cancer, colorectal cancer or colon cancer, and the disease of the CNS is Multiple sclerosis MS, amyotrophic lateral sclerosis, transmissible spongiforme encephalopathies/Prion-linked diseases, Parkinson's disease or Alzheimer disease.

10. A method for the detection of an HCBI, MSBI, MSSI or CMI polynucleic acid according to paragraph 1 in a biological sample, comprising: (a) optionally extracting sample polynucleic acid, (b) amplifying the polynucleic acid as described above with at least one primer according to paragraph 2, optionally a labelled primer, and (c) detecting the amplified polynucleic acid.

11. A method for the detection of an HCBI, MSBI, MSSI or CMI polynucleic acid according to paragraph 1 in a biological sample, comprising: (a) optionally extracting sample polynucleic acid, (b) hybridizing the polynucleic acid as described above with at least one probe according to paragraph 3, optionally a labelled probe, and (c) detecting the hybridized polynucleic acid.

12. A method for detecting a polypeptide of paragraph 6 or an antibody of paragraph 7 present in a biological sample, comprising: (a) contacting the biological sample for the presence and/or concentration of such polypeptide or antibody as defined above, and (b) detecting the immunological complex formed between said antibody and/or said polypeptide.

13. An antisense oligonucleotide reducing or inhibiting the expression of an HCBI, MSBI, MSSI or CMI polynucleic acid of 10 paragraph 1 or a vector containing said antisense oligonucleotide.

14. A pharmaceutical composition comprising the antibody or antigen binding fragment thereof of paragraph 7 or the antisense oligonucleotide of paragraph 16 and a suitable pharmaceutical carrier.

15. A vaccine comprising an HCBI, MSBI, MSSI or CMI polynucleic acid of paragraph 1 or a polypeptide according to paragraph 6.

16. The vaccine of paragraph 15, which comprises a VLP or protein/DNA or polypeptide/DNA complex or specific proteins or attenuated infectious agents.

17. Use of an HCBI, MSBI, MSSI or CMI polynucleic acid of paragraph 1 as a lead component for the development of a medicament for prevention or treatment of cancer, a disease of the CNS or diabetes.

18. Use according to paragraph 17, wherein the cancer is breast cancer, ovarian cancer, lung cancer, prostate cancer, colorectal cancer or colon cancer and the disease of the CNS is Multiple sclerosis MS, amyotrophic lateral sclerosis, transmissible spongiforme encephalopathies/Prion-linked diseases, Parkinson's disease or Alzheimer disease.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An expression vector comprising a Multiple Sclerosis Brain isolate (MSBI) polynucleic acid comprising:
    a nucleotide sequence comprising SEQ ID NO: 1, or a nucleotide sequence comprising SEQ ID NO: 10, or a nucleotide sequence having at least 99% sequence identity to SEQ ID NO: 1.

2. The expression vector of claim 1 wherein: the MSBI polynucleic acid comprises SEQ ID NO: 1 or SEQ ID NO: 10.

3. A host cell transformed with an expression vector according to claim 1.

4. A host cell transformed with an expression vector according to claim 2.

5. The host cell of claim 3, wherein the cell is a Chinese hamster cell, a monkey cell, a baby hamster kidney cell, a pig kidney cell, a rabbit kidney cell, a human osteosarcoma cell, a HeLa cell, a human hepatoma cell, or an insect cell.

6. The host cell of claim 4, wherein the cell is a Chinese hamster cell, a monkey cell, a baby hamster kidney cell, a pig kidney cell, a rabbit kidney cell, a human osteosarcoma cell, a HeLa cell a human hepatoma cell, or an insect cell.

7. The host cell of claim 5, wherein the monkey cell is a COS or Vero cell, the pig kidney cell is a PK15 cell, the rabbit kidney cell is a RK13 cell, the human osteosarcoma cell is a 143B cell line cell, the human hepatoma cell is a Hep G2 cell, or the insect cell is a Spodoptera frugiperda cell.

8. The host cell of claim 3, wherein the cell is a monkey, pig, rabbit, or human osteosarcoma cell, and the monkey cell is a COS or Vero cell, the pig kidney cell is a PK15 cell, the rabbit kidney cell is a RK13 cell, or the human osteosarcoma cell is a 143B cell.

9. The host cell of claim 6, wherein the monkey cell is a COS or Vero cell, the pig kidney cell is a PK15 cell, the rabbit kidney cell is a RK13 cell, the human osteosarcoma cell is a 143B cell line cell, the human hepatoma cell is a Hep G2 cell, or the insect cell is a Spodoptera frugiperda cell.

10. The host cell of claim 4, wherein the cell is a monkey, pig, rabbit, or human osteosarcoma cell, and the monkey cell is a COS or Vero cell, the pig kidney cell is a PK15 cell, the rabbit kidney cell is a RK13 cell, or the human osteosarcoma cell is a 143B cell.

11. The expression vector of claim 1 wherein: the vector is an adenovirus, vaccinia virus, avipox virus, herpes virus, or a retrovirus vector.

12. The expression vector of claim 11 wherein: the vaccinia virus is an Ankara Modified Virus, or the retrovirus vector is Moloney murine leukemia virus (MoMuLV), Harvey murine sarcoma virus (HaMuSV), murine mammary tumor virus (MuMTV), Rous sarcoma virus (RSV), or gibbon ape leukemia virus (GaLV).

13. A host cell transformed with an expression vector according to claim 11.

14. A host cell transformed with an expression vector according to claim 12.

15. The host cell of claim 13, wherein the cell is a Chinese hamster cell, a monkey cell, a baby hamster kidney cell, a pig kidney cell, a rabbit kidney cell, a human osteosarcoma cell, a HeLa cell a human hepatoma cell, or an insect cell.

16. The host cell of claim 14, wherein the cell is a Chinese hamster cell, a monkey cell, a baby hamster kidney cell, a pig kidney cell, a rabbit kidney cell, a human osteosarcoma cell, a Hela cell a human hepatoma cell, or an insect cell.

17. The host cell of claim 15, wherein the monkey cell is a COS or Vero cell, the pig kidney cell is a PK15 cell, the rabbit kidney cell is a RK13 cell, the human osteosarcoma cell is a 143B cell, the human hepatoma cell is a Hep G2 cell, or the insect cell is a Spodoptera frugiperda cell.

18. The host cell of claim 16, wherein the monkey cell is a COS or Vero cell, the pig kidney cell is a PK15 cell, the rabbit kidney cell is a RK13 cell, the human osteosarcoma cell is a 143B cell, the human hepatoma cell is a Hep G2 cell, or the insect cell is a Spodoptera frugiperda cell.

19. The host cell of claim 13, wherein the cell is a monkey, pig, rabbit, or human osteosarcoma cell, and the monkey cell is a COS or Vero cell, the pig kidney cell is a PK15 cell, the rabbit kidney cell is a RK13 cell, or the human osteosarcoma cell is a 143B cell.

20. The host cell of claim 14, wherein the cell is a monkey, pig, rabbit, or human osteosarcoma cell, and the monkey cell is a COS or Vero cell, the pig kidney cell is a PK15 cell, the rabbit kidney cell is a RK13 cell, or the human osteosarcoma cell is a 143B cell.

* * * * *

SEQUENCE LISTING

```
<160> NUMBER OF SEQ ID NOS: 28

<210> SEQ ID NO 1
<211> LENGTH: 1766
<212> TYPE: DNA
<213> ORGANISM: Artificial Sequence
<220> FEATURE:
<223> OTHER INFORMATION: MSBI1.176

<400> SEQUENCE: 1
aagcttgctt agtcaaaaaa gtttgagcaa agcgaaaaca tagggcaatt ttcatgaaga        60
aattgggctt ttaaagtttt taaatgcttt taaatgcttt tagacatgct aagaagccca       120
cacagcaagg catacagagg acattctcct acgtttaccg atcaataccc ctacgtttac       180
cgatcaatac ccctacgttt accgatcaat acccctacgt ttaccttgcg tataactaca       240
aagaatacta gtgtagtaat aacttcaaaa gaataattgt aggttatgag cgatttaata       300
gtaaaagata acgccctaat gaatgctagt tataacttag ctttggttga acagaggtta       360
attctattag caatcataga agcgagagaa acaggcaaag ggattaatgc caatgatcct       420
ttaacagttc atgcaagtag ctatatcaat caatttaacg tagaaaggca tacggcatat       480
caagccctca aagatgcttg taaagacttg tttgcccgtc aattcagtta ccaagaaaag       540
cgagaacgag gacgaattaa tattacaagt cgatgggttt cgcaaattgg ctatatggac       600
gatacagcaa ccgttgagat tattttttgcc cctgcggttg ttcctctgat tacacggcta       660
gaggaacagt tcacccagta cgatattgag caaattagcg gtttatcgag tgcatatgct       720
gttcgtatgt acgaactgct gatttgttgg cgtagcacag gcaaaacacc aattattgag       780
ctagacgagt ttagaaagcg aataggtgtt ttagatactg aatacactag aacagataat       840
ttaaagatgc gagttattga attagcccta aaacaaatca acgaacatac agacatcaca       900
gcaagctatg aacaacacaa aaaagggcga gtgattacag gattctcatt caagtttaag       960
cacaagaaac aaaacagcga taaaacgcca aaaaatagcg attctagccc acgtatcgta      1020
aaacatagtc aaatccctac caacattgta aaacagcctg aaaacgccaa aatgagcgat      1080
ttagaacata gagcgagccg tgttacaggg gaaataatgc gaaatcgtct gtcagatcgg      1140
tttaaacaag gcgatgaatc agcaatcgac atgatgaaac gtattcaaag tgaaataata      1200
accgatgcaa tagcagacca gtgggaaagc aaactggagg agtttggcgt ggttttttag      1260
tcatgacgat ttcccgaagg gcgcacttag ccattgagaa aaatcttcga tttttttcaat      1320 ggaagtccgt gggggtaaac ccctcaaccc caaaagcaaa aacactgtaa tcagggaaaa      1380 aacattttttg attttgatcc ttgtttgtca ctcgtagaca ctcgttttgt tttgctcttt      1440
ctagaattca caaaaaagat attagcgagt gtctacgagc gactcaatga aagttcgatt      1500 attcccccctc tggaaaaccg ctttttaaaaa tattggctgc tagatggttt ttactatagt      1560
gaggttttgc ttttaaaaaa acacgagcaa agcgagttca tagttgcttt tgcttgtttt      1620
cgggtcttag gggaaatccc ctaacaagtc ctcgaatatc aaaatgtggc tacattttgt      1680
atatacgggt aggcttgctt atttgatttt ttttcttcta aacctttgac ttcttcccca      1740
ttgtttgcag aaattgcccc tcgact                                          1766
```

-continued

```
<210> SEQ ID NO 2
<211> LENGTH: 1439
<212> TYPE: DNA
<213> ORGANISM: Artificial Sequence
<220> FEATURE:
<223> OTHER INFORMATION: query

<400> SEQUENCE: 2
aagcttgctt agtcaaaaaa gtttgagcaa agcgaaaaca tagggcaatt ttcatgaaga        60
aattgggctt ttaaagtttt taaatgcttt taaatgcttt tagacatgct aagaagccca       120
cacagcaagg catacagagg acattctcct acgtttaccg atcaataccc ctacgtttac       180
cgatcaatac ccctacgttt accgatcaat acccctacgt ttaccttgcg tataactaca       240
aagaatacta gtgtagtaat aacttcaaaa gaataattgt aggttatgag cgatttaata       300
gtaaaagata acgccctaat gaatgctagt tataacttag ctttggttga acagaggtta       360
attctattag caatcataga agcgagagaa acaggcaaag ggattaatgc caatgatcct       420
ttaacagttc atgcaagtag ctatatcaat caatttaacg tagaaaggca tacggcatat       480
caagccctca aagatgcttg taaagacttg tttgcccgtc aattcagtta ccaagaaaag       540
cgagaacgag gacgaattaa tattacaagt cgatgggttt cgcaaattgg ctatatggac       600
gatacagcaa ccgttgagat tatttttgcc cctgcggttg ttcctctgat tacacggcta       660
gaggaacagt tcacccagta cgatattgag caaattagcg gtttatcgag tgcatatgct       720
gttcgtatgt acgaactgct gatttgttgg cgtagcacag gcaaaacacc aattattgag       780
ctagacgagt ttagaaagcg aataggtgtt ttagatactg aatacactag aacagataat       840
ttaaagatgc gagttattga attagcccta aaacaaatca acgaacatac agacatcaca       900
gcaagctatg aacaacacaa aaaagggcga gtgattacag gattctcatt caagtttaag       960
cacaagaaac aaaacagcga taaaacgcca aaaaatagcg attctagccc acgtatcgta      1020
aaacatagtc aaatccctac caacattgta aaacagcctg aaaacgccaa aatgagcgat      1080
ttagaacata gagcgagccg tgttacaggg gaaataatgc gaaatcgtct gtcagatcgg      1140
tttaaacaag gcgatgaatc agcaatcgac atgatgaaac gtattcaaag tgaaataata      1200
accgatgcaa tagcagacca gtgggaaagc aaactggagg agtttggcgt ggttttttag      1260
tcatgacgat ttcccgaagg gcgcacttag ccattgagaa aaatcttcga tttttttcaat      1320 ggaagtccgt gggggtaaac ccctcaaccc caaaagcaaa aacactgtaa tcagggaaaa      1380 aacattttg attttgatcc ttgtttgtca ctcgtagaca ctcgttttgt tttgctctt       1439

<210> SEQ ID NO 3
<211> LENGTH: 1434
<212> TYPE: DNA
<213> ORGANISM: Artificial Sequence
<220> FEATURE:
<223> OTHER INFORMATION: subject

<400> SEQUENCE: 3
aagcttgctt agtcaaaaaa gtttgagcaa agcgaaaaca tagggcaatt ttcatgaaga        60
aattgggctt ttaaagtttt taaatgtttt aaatgctttt agacatgcta agaagcccac       120
acagcaaggc atacagagga cattctccta cgtttaccga tcaataccccc cgtttaccga       180 tcaataccccc tacgtttacc gatcaatacc cctacgttta ccttgcgtat aactacaaag       240
aatactagtg tagtataact tcaaaagaat aattgtaggt tatgagcgat ttaatagtaa       300
```

-continued

```
aagataacgc cctaatgaat gctagttata acttagcttt ggttgaacag aggttaattc      360
tattagcaat catagaagcg agagaaacag gcaaagggat taatgccaat gatcctctta      420
cggttcatgc aggtagctat atcaatcaat ttaacgtaca aaggcatacg gcatatcaag      480
ccctcaaaga tgcttgtaaa gacttgtttg cccgtcaatt cagttaccaa gaaaagcgag      540
aacgaggacg aattaatatt acaagtcgat gggtttcgca aattggctat atggacgata      600
cagcaaccgt tgagattatt tttgcccctg cggttgttcc tctgattaca cggctagagg      660
aacagttcac ccagtacgat attgagcaaa ttagcggttt atcgagtgca tatgctgttc      720
gtatgtacga actgctgatt tgttggcgta gcacaggcaa aacaccaatt attgagctag      780
acgagtttag aaagcgaata ggtgtttttag atactgaata cactagaaca gataatttaa      840
agatgcaagt tattgaatta gccctaaaac aaatcaacga acatactgac atcacagcaa      900
gctatgaaca acacaaaaaa gggcgagtga ttaccggatt ctcattcatg tttaagcaca      960
agaaacaaaa cagcgataaa acgcctgata ctaacgcttc tagcccacgt atcgtaaaac     1020
atagtcaaat ccctaccaac attgtaaaac agcctgaaaa cgccaaaatg agcgatttag     1080
aacatagagc gagccgtgtt acaggggaaa taatgcgaaa tcgtctgtca gatcggttta     1140
aacaaggcga tgaatcagca atcgacatga tgaaacgtat tcaaagtgaa ataataaccg     1200
atgcaatagc agaccagtgg gaaagcaaac tggaggagtt tggcgtggtt ttttagtcat     1260
gacgatttcc cgaagggcgc acttagccat tgagaaaaat cttcgatttt ttcaatggaa     1320
gtccgtgggg gtaaacccct caaccccaaa agcaaaaaca ctgtaatcag ggaaaaaaca     1380
tttttgattt tgatccttgt ttgcactcgt agacactcgt tttgtttttgc tctt          1434
```

```
<210> SEQ ID NO 4
<211> LENGTH: 325
<212> TYPE: DNA
<213> ORGANISM: Artificial Sequence
<220> FEATURE:
<223> OTHER INFORMATION: query

<400> SEQUENCE: 4
tctagaattc acaaaaaaga tattagcgag tgtctacgag cgactcaatg aaagttcgat       60 tattcccccct ctggaaaacc gctttttaaaa atattggctg ctagatggtt tttactatag     120
tgaggttttg cttttaaaaa aacacgagca aagcgagttc atagttgctt ttgcttgttt      180
tcgggtctta ggggaaatcc cctaacaagt cctcgaatat caaaatgtgg ctacattttg      240
tatatacggg taggcttgct tatttgattt tttttcttct aaacctttga cttcttcccc      300
attgtttgca gaaattgccc ctcga                                           325
```

```
<210> SEQ ID NO 5
<211> LENGTH: 325
<212> TYPE: DNA
<213> ORGANISM: Artificial Sequence
<220> FEATURE:
<223> OTHER INFORMATION: subject

<400> SEQUENCE: 5
tctagaattc acaaaaaaga tattagcgag tgtctacgag cgactcaatg aaagttcgat       60 tattcccccct ctggaaaacc gctttttaaaa atattggctg ctagatggtt tttactatag     120
tgaggttttg cttttaaaaa aacacgagca aagcgagttc atagttgctt ttgcttgttt      180
tcgggtctta ggggaaatcc cctaacaagt cctcgaatat caaaatgtgg ctacattttg      240
tatatacggg taggcttgct tatttgattt tttttcttct aaacctttga cttcttcccc      300
```
attgtttgca gaaattgccc ctcga                                          325

<210> SEQ ID NO 6
<211> LENGTH: 324
<212> TYPE: PRT
<213> ORGANISM: Artificial Sequence
<220> FEATURE:
<223> OTHER INFORMATION: query

<400> SEQUENCE: 6

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
            115                 120                 125

Phe Thr Gln Tyr Asp Ile Glu Gln Ile Ser Gly Leu Ser Ser Ala Tyr
        130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
            195                 200                 205

Glu Gln His Lys Lys Gly Arg Val Ile Thr Gly Phe Ser Phe Lys Phe
        210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
            275                 280                 285

Gly Asp Glu Ser Ala Ile Asp Met Met Lys Arg Ile Gln Ser Glu Ile
        290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 7
<211> LENGTH: 324
<212> TYPE: PRT

```
<213> ORGANISM: Artificial Sequence
<220> FEATURE:
<223> OTHER INFORMATION: subject

<400> SEQUENCE: 7

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
        35                  40                  45

His Ala Gly Ser Tyr Ile Asn Gln Phe Asn Val Gln Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
            115                 120                 125

Phe Thr Gln Tyr Asp Ile Glu Gln Ile Ser Gly Leu Ser Ser Ala Tyr
        130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Gln Val Ile Glu
            180                 185                 190

Leu Ala Leu Lys Gln Ile Asn Glu His Thr Asp Ile Thr Ala Ser Tyr
            195                 200                 205

Glu Gln His Lys Lys Gly Arg Val Ile Thr Gly Phe Ser Phe Met Phe
    210                 215                 220

Lys His Lys Lys Gln Asn Ser Asp Lys Thr Pro Asp Thr Asn Ala Ser
225                 230                 235                 240

Ser Pro Arg Ile Val Lys His Ser Gln Ile Pro Thr Asn Ile Val Lys
            245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
        275                 280                 285

Gly Asp Glu Ser Ala Ile Asp Met Met Lys Arg Ile Gln Ser Glu Ile
    290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 8
<211> LENGTH: 324
<212> TYPE: PRT
<213> ORGANISM: Artificial Sequence
<220> FEATURE:
<223> OTHER INFORMATION: query

<400> SEQUENCE: 8

Met Ser Asp Leu Ile Val Lys Asp Asn Ala Leu Met Asn Ala Ser Tyr
```

-continued

```
1               5                    10                   15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
            35                  40                  45

His Ala Ser Ser Tyr Ile Asn Gln Phe Asn Val Glu Arg His Thr Ala
            50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
            115                 120                 125

Phe Thr Gln Tyr Asp Ile Glu Gln Ile Ser Gly Leu Ser Ser Ala Tyr
            130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
            195                 200                 205

Glu Gln His Lys Lys Gly Arg Val Ile Thr Gly Phe Ser Phe Lys Phe
            210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
            275                 280                 285

Gly Asp Glu Ser Ala Ile Asp Met Met Lys Arg Ile Gln Ser Glu Ile
            290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 9
<211> LENGTH: 324
<212> TYPE: PRT
<213> ORGANISM: Artificial Sequence
<220> FEATURE:
<223> OTHER INFORMATION: subject

<400> SEQUENCE: 9

Met Ser Glu Leu Ile Val Lys Asp Asn Ala Leu Met Asn Ala Ser Tyr
1               5                    10                   15

Asn Leu Asp Leu Val Glu Gln Arg Leu Ile Leu Leu Ala Ile Val Glu
            20                  25                  30

Ala Arg Glu Ser Gly Lys Gly Ile Asn Ala Asn Asp Pro Leu Thr Val
            35                  40                  45
```

-continued

```
His Ala Glu Ser Tyr Ile Asn Gln Phe Gly Val His Arg Thr Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ala Asn Ile Thr Ser Arg
                85                  90                  95

Trp Val Ser Gln Ile Ala Tyr Ile Asp Glu Thr Ala Thr Val Glu Ile
                100                 105                 110

Ile Phe Ala Pro Ala Val Val Pro Leu Ile Thr Arg Leu Glu Lys Gln
                115                 120                 125

Phe Thr Gln Tyr Asp Ile Glu Gln Ile Ser Gly Leu Ser Ser Ala Tyr
        130                 135                 140

Ala Val Arg Met Tyr Glu Leu Leu Ile Cys Trp Arg Ser Thr Gly Lys
145                 150                 155                 160

Thr Pro Val Ile Glu Leu Gly Glu Phe Arg Lys Arg Ile Gly Val Leu
                165                 170                 175

Asp Thr Glu Tyr Ile Arg Thr Asp Asn Leu Lys Met Arg Val Ile Glu
                180                 185                 190

Leu Ala Leu Lys Gln Ile Asn Asp His Thr Asp Ile Thr Ala Thr Tyr
        195                 200                 205

Glu Gln His Lys Lys Gly Arg Thr Ile Thr Gly Phe Ser Phe Lys Phe
    210                 215                 220

Lys Gln Lys Arg Lys Thr Glu Leu Glu Thr Pro Lys Asn Ser Asp Ser
225                 230                 235                 240

Asp Val Pro Lys Gln Lys Ser Val Glu Ile Pro Thr Asn Leu Val Lys
                245                 250                 255

Gln Pro Glu Asn Ala Asn Met Ser Asp Leu Gln His Arg Ala Ser Lys
                260                 265                 270

Ile Thr Gly Leu Ile Met Ser Asn Arg Leu Ser Asp Arg Phe Lys Gln
        275                 280                 285

Ser Asp Glu Ser Ile Met Gln Met Met Ala Arg Ile Gln Ser Glu Ile
    290                 295                 300

Thr Asp Glu Ala Ile Ala Asn Gln Trp Glu Asn Lys Leu Glu Glu Phe
305                 310                 315                 320

Gly Val Ile Phe
```

```
<210> SEQ ID NO 10
<211> LENGTH: 1766
<212> TYPE: DNA
<213> ORGANISM: Artificial Sequence
<220> FEATURE:
<223> OTHER INFORMATION: MSBI2.176

<400> SEQUENCE: 10
aagcttgctt agtcaaaaaa gtttgagcaa agcgaaaaca tagggcaatt ttcgtgatga      60
aaatgggctt ttaatgtttt taaatgcttt taaatgcttt tagacatgct gaaacgctta     120
tatagcaatg catacagagg acatatgtcc acgtttacct atcaatatgt ccacgtttac     180
ctatcaatat gtccacgttt acctatcaat atgtccacgt ttaccttgcg tatttacaca     240
catttaaata gtatggatat atccaatgaa attataatgt gtacttatga gcaaattagt     300
agtgaaagac aatgccctaa tgaacgctag ttacaacttg gatctcgttg aacagcgttt     360
aattctattg gcaatcatcg aagcaagaga atcaggcaaa ggaattaatg caaatgaccc     420
gcttacggtt catgcagaga gttatatcaa tcaatttggt gttcatcgag taactgcata     480
```

-continued

```
tcaagctctc aaagatgctt gtgataactt gtttgcacgt caattcagct accaatccaa      540
aagtgaaaaa gggaacatac aaaatcatcg ttcacgttgg gttagtgaaa ttatttacat      600
tgatacagaa gcaacagtaa aaataatatt tgcacctgct attgtcccac tgattacaag      660
gctagaagaa cagttcacca agtatgatat tgagcaaatt agtgatttat cgagtgctta      720
tgcaattcgc ttatacgagt tattgatttg ctggcgtagc acagggaaaa caccaattat      780
tgggctaggc gaatttagaa atcgggttgg tgtgttagat agtgaatatc atcgaattgc      840
acacttgaaa gaacgagtta ttgaacattc aattaaacag attaacgagc ataccgacat      900
cacagccacc tacgaacagc acaaaaaagg gcggacaatc acaggatttt cattcaagtt      960
taagcagaag aagcccaaac aagccgaaat tgctacagaa acgccaaaaa cagccacgaa     1020
tgacccagac acgacaaaac cccttacaga gcctcagatc gcaaaataca gcatgattct     1080
gtgcaaacta ggcagtattt cagacttgag taacttccca gactatccag cttttgcaaa     1140
ttggattggg aacattttga ggaaccctga aaaagcagat gaacaaatag caaaacggat     1200
tttcacagca ttgaaaacag aaaccgacta cagcaagaaa aactaatttt tagttgtgat     1260 gggtttttccc gaaataacat gaagggcgca cttacgcaaa attttttgcta cgccaaattt     1320 tgcaagtacg gtcagggaaa ccccgacacc ccaaaagcaa aaacactgta atcagggaaa     1380 aaacatttt gattttgatc cttgtttgtc actcgtagac actcgttttg ttttgctctt     1440
tctagaattc acaaaaaaga tattagcgag tgtctacgag cgactcaatg aaagttcgat     1500
tattccccct ctggaaaacc gctttttaaaa atattggctg ctagatggtt tttactatag     1560
tgaggttttg cttttaaaaa aacacgagca aagcgagttc atagttgctt ttgcttgttt     1620
tcgggtctta ggggaaatcc cctaacaagt cctcgaatat caaaatgtgg ctacattttg     1680
tatatacggg taggcttgct tatttgattt tttttcttct aaacctttga cttcttcccc     1740
attgtttgca gaaatgcccc ccgacc                                          1766
```

<210> SEQ ID NO 11
<211> LENGTH: 1284
<212> TYPE: DNA
<213> ORGANISM: Artificial Sequence
<220> FEATURE:
<223> OTHER INFORMATION: query

<400> SEQUENCE: 11

```
agtcaaaaaa gtttgagcaa agcgaaaaca tagggcaatt ttcgtgatga aaatgggctt       60
ttaatgtttt taaatgcttt taaatgcttt tagacatgct gaaacgctta tatagcaatg      120
catacagagg acatatgtcc acgtttacct atcaatatgt ccacgtttac ctatcaatat      180
gtccacgttt acctatcaat atgtccacgt ttaccttgcg tatttacaca catttaaata      240
gtatggatat atccaatgaa attataatgt gtacttatga gcaaattagt agtgaaagac      300
aatgccctaa tgaacgctag ttacaacttg gatctcgttg aacagcgttt aattctattg      360
gcaatcatcg aagcaagaga atcaggcaaa ggaattaatg caaatgaccc gcttacggtt      420
catgcagaga gttatatcaa tcaatttggt gttcatcgag taactgcata tcaagctctc      480
aaagatgctt gtgataactt gtttgcacgt caattcagct accaatccaa aagtgaaaaa      540
gggaacatac aaaatcatcg ttcacgttgg gttagtgaaa ttatttacat tgatacagaa      600
gcaacagtaa aaataatatt tgcacctgct attgtcccac tgattacaag gctagaagaa      660
cagttcacca agtatgatat tgagcaaatt agtgatttat cgagtgctta tgcaattcgc      720
```

-continued

```
ttatacgagt tattgatttg ctggcgtagc acagggaaaa caccaattat tgggctaggc      780
gaatttagaa atcgggttgg tgtgttagat agtgaatatc atcgaattgc acacttgaaa      840
gaacgagtta ttgaacattc aattaaacag attaacgagc ataccgacat cacagccacc      900
tacgaacagc acaaaaaagg gcggacaatc acaggatttt cattcaagtt taagcagaag      960
aagcccaaac aagccgaaat tgctacagaa acgccaaaaa cagccacgaa tgacccagac     1020
acgacaaaac cccttacaga gcctcagatc gcaaaataca gcatgattct gtgcaaacta     1080
ggcagtattt cagacttgag taacttccca gactatccag cttttgcaaa ttggattggg     1140
aacattttga ggaaccctga aaaagcagat gaacaaatag caaaacggat tttcacagca     1200
ttgaaaacag aaaccgacta cagcaagaaa aactaatttt tagttgtgat gggtttttccc     1260 gaaataacat gaagggcgca ctta                                           1284
```

<210> SEQ ID NO 12
<211> LENGTH: 1283
<212> TYPE: DNA
<213> ORGANISM: Artificial Sequence
<220> FEATURE:
<223> OTHER INFORMATION: subject

<400> SEQUENCE: 12

```
agtcaaaaaa gtttgagaga agcgaaaaca tagggcaatt tcatggtgag aatgggcttt       60
taaggttttt aaaagctttt aaatgctttt agacatgctg aaacgaccac acagcaaggc      120
atacagaggg catatgtcca cgtttaccta tcaatatgtc cacgtttacc tatcaatatg      180
tccacgttta cctatcaata tgtccacgtt taccttgcat agtcacacat atttaaataa      240
tatggatata tccaataaaa ttataatgtg tacttatgag taggttagta gtgaaagaca      300
atgccctaat gaacgctagt tataacttgg atctcgttga acagcgttta atcctattgg      360
caatcatcga agcgagggag tcaggcaaag gaattaacgc caatgaccct ctaacaatcc      420
atgcagagag ctacatcaat caatttggtg ttcatcgagt aactgcatat caagctctca      480
aagatgcttg tgataacctg tttgcacgtc aattcagcta tcagtccaaa agtgaaaaag      540
gaaacataca aaatcatcgt tcacgctggg ttagtgaaat tatttacatc gacacagaag      600
caacagtaaa aataatcttt gcacctgcta tcgtcccact gattacaaga ttagaagaac      660
agttcaccaa gtatgatatt cagcaaatta gtgatttatc gagtgcttat gcaatccgct      720
tatacgaatt attgatttgt tggcgtagca cagggaaaac gccaattatt gaattagctg      780
aatttaggaa tcgggttggt gtgttagata ctgaatatca tcgaattgcc cacttgaaag      840
agcgagttat tgaacattca attaaacaaa ttaacgaaca taccgacatc acagcgacct      900
acgaacagca taaaaaaggg cgagtgatta cagggttctc attcaaattt aagcagaaga      960
agcccaaaca agccgagatt gccacagaaa cgcccaaaac agccacgaat gacctagata     1020
cgataaaacc ccttacagag ccacagatcg caaaatacag catgattctg tgcaaactag     1080
gcagtatttc agacttgagt aacttcccag actatccagc ttttgcaaat tggattggga     1140
acattttgag gaaccctgaa aaagcagatg aacaaatagc aaaacggatt ttcacagcat     1200
tgaaaacaga aaccgactac agcaagaaaa ctaattttt agttgtgatg ggtttttcccg     1260 aaataacatg aagggcgcac tta                                            1283
```

<210> SEQ ID NO 13
<211> LENGTH: 125
<212> TYPE: DNA
<213> ORGANISM: Artificial Sequence

```
<220> FEATURE:
<223> OTHER INFORMATION: query

<400> SEQUENCE: 13
cctaacaagt cctcgaatat caaaatgtgg ctacattttg tatatacggg taggcttgct        60
tatttgattt tttttcttct aaacctttga cttcttcccc attgtttgca gaaatgcccc       120
ccgac                                                                   125

<210> SEQ ID NO 14
<211> LENGTH: 125
<212> TYPE: DNA
<213> ORGANISM: Artificial Sequence
<220> FEATURE:
<223> OTHER INFORMATION: subject

<400> SEQUENCE: 14
cctaacaagt ccccgaatat caaaatgtgg ctacattttg tatatacggg taggcttgct        60
tattgaatct aattcctttt taaacctttc gactttccct atcctttgca taaattgccc       120
ctgac                                                                   125

<210> SEQ ID NO 15
<211> LENGTH: 885
<212> TYPE: DNA
<213> ORGANISM: Artificial Sequence
<220> FEATURE:
<223> OTHER INFORMATION: query

<400> SEQUENCE: 15
attaacgagc ataccgacat cacagccacc tacgaacagc acaaaaaagg gcggacaatc        60
acaggatttt cattcaagtt taagcagaag aagcccaaac aagccgaaat tgctacagaa       120
acgccaaaaa cagccacgaa tgacccagac acgacaaaac cccttacaga gcctcagatc       180
gcaaaataca gcatgattct gtgcaaacta ggcagtattt cagacttgag taacttccca       240
gactatccag cttttgcaaa ttggattggg aacattttga ggaaccctga aaaagcagat       300
gaacaaatag caaaacggat tttcacagca ttgaaaacag aaaccgacta cagcaagaaa       360
aactaatttt tagttgtgat gggtttttccc gaaataacat gaagggcgca cttacgcaaa       420
atttttgcta cgccaaattt tgcaagtacg gtcagggaaa ccccgacacc ccaaaagcaa       480
aaacactgta atcagggaaa aaacattttt gattttgatc cttgtttgtc actcgtagac       540
actcgttttg ttttgctctt tctagaattc acaaaaaaga tattagcgag tgtctacgag       600
cgactcaatg aaagttcgat tattccccct ctggaaaacc gcttttaaaa atattggctg       660
ctagatggtt tttactatag tgaggttttg cttttaaaaa aacacgagca aagcgagttc       720
atagttgctt ttgcttgttt tcgggtctta ggggaaatcc cctaacaagt cctcgaatat       780
caaaatgtgg ctacattttg tatatacggg taggcttgct tatttgattt tttttcttct       840
aaacctttga cttcttcccc attgtttgca gaaatgcccc ccgac                       885

<210> SEQ ID NO 16
<211> LENGTH: 890
<212> TYPE: DNA
<213> ORGANISM: Artificial Sequence
<220> FEATURE:
<223> OTHER INFORMATION: subject

<400> SEQUENCE: 16
atcaacgagc acaccgacat cacagccacc tacgaacagc acaaaaaagg gcggacaatc        60
```

-continued

```
acaggatttt cattcaagtt taagcagaag aagcccaaac aagccgaaat tgctacagaa      120
acgccaaaaa cagccacgaa tgacccagac acgacaaaac cccttacaga gcctcagatc      180
gcaaaataca gcatgattct gtgcaaacta ggcagtattt cagacttgag taacttccca      240
gactatccag cttttgcaaa ttggattggg aacattttga ggaaccctga aaaagcagat      300
gaacaaatag caaaacggat tttcacagca ttgaaaacag aaaccgacta cagcaagaaa      360
aactaatttt tagttgtgat gggtttttccc gaaataacat gaagggcgca cttagccatt      420
gagaaaaatc ttcgattttt tcaatggaag tccgtggggg taaacccctc aaccccaaaa      480
gcaaaaacac tgtaatcagg gaaaaaacat ttttgatttt gatccttgtt tgtcactcgt      540
agacactcgt tttgttttgc tctttctaga attcacaaaa aagatattag cgagtgtcta      600
cgagcgactc aatgaaagtt cgattattcc ccctctggaa aaccgctttt aaaaatattg      660
gctgctagat ggttttttact atagtgaggt tttgctttta aaaaaacacg agcaaagcga      720
gttcatagtt gcttttgctt gttttcgggt cttaggggaa atcccctaac aagtcctcga      780
atatcaaaat gtggctacat tttgtatata cgggtaggct tgcttatttg attttttttc      840
ttctaaacct ttgacttctt ccccattgtt tgcagaaatt gccctcgac                890

<210> SEQ ID NO 17
<211> LENGTH: 324
<212> TYPE: DNA
<213> ORGANISM: Artificial Sequence
<220> FEATURE:
<223> OTHER INFORMATION: query

<400> SEQUENCE: 17
aagcttgctt agtcaaaaaa gtttgagcaa agcgaaaaca tagggcaatt ttcgtgatga       60
aaatgggctt ttaatgtttt taaatgcttt taaatgcttt tagacatgct gaaacgctta      120
tatagcaatg catacagagg acatatgtcc acgtttacct atcaatatgt ccacgtttac      180
ctatcaatat gtccacgttt acctatcaat atgtccacgt ttaccttgcg tatttacaca      240
catttaaata gtatggatat atccaatgaa attataatgt gtacttatga gcaaattagt      300
agtgaaagac aatgccctaa tgaa                                            324

<210> SEQ ID NO 18
<211> LENGTH: 324
<212> TYPE: DNA
<213> ORGANISM: Artificial Sequence
<220> FEATURE:
<223> OTHER INFORMATION: subject

<400> SEQUENCE: 18
aagcttgctt agtcaaaaaa gtttgagcaa agcgaaaaca tagggcaatt ttcgtgatga       60
aaatgggctt ttaatgtttt taaatgcttt taaatgcttt tagacatgct gaaacgctta      120
tatagcaatg catacagagg acatatgtcc acgtttacct atcaatatgt ccacgtttac      180
ctatcaatat gtccacgttt acctatcaat atgtccacgt ttaccttgcg tatttacaca      240
catttaaata gtatggatat atccaatgag attataatgt gtacttatga gcaaattagt      300
agtgaaagac aatgccctaa tcaa                                            324

<210> SEQ ID NO 19
<211> LENGTH: 319
<212> TYPE: PRT
<213> ORGANISM: Artificial Sequence
<220> FEATURE:
<223> OTHER INFORMATION: query
```

-continued

<400> SEQUENCE: 19

```
Met Ser Lys Leu Val Val Lys Asp Asn Ala Leu Met Asn Ala Ser Tyr
1               5                   10                  15

Asn Leu Asp Leu Val Glu Gln Arg Leu Ile Leu Leu Ala Ile Ile Glu
            20                  25                  30

Ala Arg Glu Ser Gly Lys Gly Ile Asn Ala Asn Asp Pro Leu Thr Val
        35                  40                  45

His Ala Glu Ser Tyr Ile Asn Gln Phe Gly Val His Arg Val Thr Ala
    50                  55                  60

Tyr Gln Ala Leu Lys Asp Ala Cys Asp Asn Leu Phe Ala Arg Gln Phe
65                  70                  75                  80

Ser Tyr Gln Ser Lys Ser Glu Lys Gly Asn Ile Gln Asn His Arg Ser
                85                  90                  95

Arg Trp Val Ser Glu Ile Ile Tyr Ile Asp Thr Glu Ala Thr Val Lys
                100                 105                 110

Ile Ile Phe Ala Pro Ala Ile Val Pro Leu Ile Thr Arg Leu Glu Glu
                115                 120                 125

Gln Phe Thr Lys Tyr Asp Ile Glu Gln Ile Ser Asp Leu Ser Ser Ala
        130                 135                 140

Tyr Ala Ile Arg Leu Tyr Glu Leu Leu Ile Cys Trp Arg Ser Thr Gly
145                 150                 155                 160

Lys Thr Pro Ile Ile Gly Leu Gly Glu Phe Arg Asn Arg Val Gly Val
                165                 170                 175

Leu Asp Ser Glu Tyr His Arg Ile Ala His Leu Lys Glu Arg Val Ile
            180                 185                 190

Glu His Ser Ile Lys Gln Ile Asn Glu His Thr Asp Ile Thr Ala Thr
            195                 200                 205

Tyr Glu Gln His Lys Lys Gly Arg Thr Ile Thr Gly Phe Ser Phe Lys
    210                 215                 220

Phe Lys Gln Lys Lys Pro Lys Gln Ala Glu Ile Ala Thr Glu Thr Pro
225                 230                 235                 240

Lys Thr Ala Thr Asn Asp Pro Asp Thr Thr Lys Pro Leu Thr Glu Pro
                245                 250                 255

Gln Ile Ala Lys Tyr Ser Met Ile Leu Cys Lys Leu Gly Ser Ile Ser
            260                 265                 270

Asp Leu Ser Asn Phe Pro Asp Tyr Pro Ala Phe Ala Asn Trp Ile Gly
            275                 280                 285

Asn Ile Leu Arg Asn Pro Glu Lys Ala Asp Glu Gln Ile Ala Lys Arg
    290                 295                 300

Ile Phe Thr Ala Leu Lys Thr Glu Thr Asp Tyr Ser Lys Lys Asn
305                 310                 315
```

```
<210> SEQ ID NO 20
<211> LENGTH: 312
<212> TYPE: PRT
<213> ORGANISM: Artificial Sequence
<220> FEATURE:
<223> OTHER INFORMATION: subject
```

<400> SEQUENCE: 20

```
Met Arg Glu Leu Val Val Lys Asp Asn Ala Leu Ile Asn Ala Ser Tyr
1               5                   10                  15

Asn Leu Asp Leu Val Glu Gln Arg Leu Ile Leu Leu Ala Ile Val Glu
            20                  25                  30
```

-continued

Ala Arg Glu Ser Gly Lys Gly Ile Asn Ala Asn Asp Pro Leu Val Val
        35                  40                  45

His Ala Glu Ser Tyr Ile Asn Gln Phe Asn Val His Arg Asn Thr Ala
    50                  55                  60

Tyr Gln Ala Leu Lys Asp Ala Cys His Asp Leu Phe Val Arg Gln Phe
65                  70                  75                  80

Ser Tyr Gln Lys Val Asn Asp Arg Gly Asn Val Glu His Tyr Arg Ser
                85                  90                  95

Arg Trp Val Ser Glu Ile Gly Tyr Val Asp Asn Glu Ala Ile Val Lys
                100                 105                 110

Leu Ile Phe Ala Pro Ala Ile Val Pro Leu Ile Thr Arg Leu Glu Glu
            115                 120                 125

Gln Phe Thr Lys Tyr Glu Leu Gln Gln Val Ser Gln Leu Thr Ser Ala
        130                 135                 140

Tyr Ala Val Arg Leu Tyr Glu Leu Leu Ile Ala Trp Arg Ser Thr Gly
145                 150                 155                 160

Lys Thr Pro Val Ile Glu Leu Ala Asp Phe Arg Lys Arg Ile Gly Ile
                165                 170                 175

Leu Glu Thr Glu Tyr Lys Arg Met Glu Arg Phe Lys Thr Ser Val Leu
            180                 185                 190

Glu Leu Ala Ile Asn Gln Ile Asn Glu His Thr Asp Ile Asn Val Ala
        195                 200                 205

Tyr Glu Gln His Lys Lys Gly Arg Ser Ile Val Gly Phe Ser Phe Asn
        210                 215                 220

Phe Ser Gln Lys Glu Lys Lys Lys Ile Leu Glu Lys Ala Gln Val Ser
225                 230                 235                 240

Glu Gly Phe Lys Lys Leu Thr Glu Ala Gln Ile Thr Lys Tyr Ser Thr
                245                 250                 255

Val Leu Ser Lys Leu His Glu Leu Ser Asp Leu Ser Thr Phe Gln Asp
                260                 265                 270

Tyr Gln Ser Phe Ser Ile Trp Ile Gly Asn Ile Leu Arg Glu Pro Glu
            275                 280                 285

Ser Val Arg Phe Glu Thr Ala Glu Arg Ile Phe Ser Ser Leu Phe Lys
        290                 295                 300

Arg Thr Asp Phe Ala Ser Pro Asn
305                 310

<210> SEQ ID NO 21
<211> LENGTH: 319
<212> TYPE: PRT
<213> ORGANISM: Artificial Sequence
<220> FEATURE:
<223> OTHER INFORMATION: query

<400> SEQUENCE: 21

Met Ser Lys Leu Val Val Lys Asp Asn Ala Leu Met Asn Ala Ser Tyr
1               5                   10                  15

Asn Leu Asp Leu Val Glu Gln Arg Leu Ile Leu Leu Ala Ile Ile Glu
                20                  25                  30

Ala Arg Glu Ser Gly Lys Gly Ile Asn Ala Asn Asp Pro Leu Thr Val
        35                  40                  45

His Ala Glu Ser Tyr Ile Asn Gln Phe Gly Val His Arg Val Thr Ala
    50                  55                  60

Tyr Gln Ala Leu Lys Asp Ala Cys Asp Asn Leu Phe Ala Arg Gln Phe
65                  70                  75                  80

```
Ser Tyr Gln Ser Lys Ser Glu Lys Gly Asn Ile Gln Asn His Arg Ser
            85              90              95

Arg Trp Val Ser Glu Ile Ile Tyr Ile Asp Thr Glu Ala Thr Val Lys
            100             105             110

Ile Ile Phe Ala Pro Ala Ile Val Pro Leu Ile Thr Arg Leu Glu Glu
            115             120             125

Gln Phe Thr Lys Tyr Asp Ile Glu Gln Ile Ser Asp Leu Ser Ser Ala
    130             135             140

Tyr Ala Ile Arg Leu Tyr Glu Leu Leu Ile Cys Trp Arg Ser Thr Gly
145             150             155             160

Lys Thr Pro Ile Ile Gly Leu Gly Glu Phe Arg Asn Arg Val Gly Val
            165             170             175

Leu Asp Ser Glu Tyr His Arg Ile Ala His Leu Lys Glu Arg Val Ile
            180             185             190

Glu His Ser Ile Lys Gln Ile Asn Glu His Thr Asp Ile Thr Ala Thr
            195             200             205

Tyr Glu Gln His Lys Lys Gly Arg Thr Ile Thr Gly Phe Ser Phe Lys
    210             215             220

Phe Lys Gln Lys Lys Pro Lys Gln Ala Glu Ile Ala Thr Glu Thr Pro
225             230             235             240

Lys Thr Ala Thr Asn Asp Pro Asp Thr Thr Lys Pro Leu Thr Glu Pro
            245             250             255

Gln Ile Ala Lys Tyr Ser Met Ile Leu Cys Lys Leu Gly Ser Ile Ser
            260             265             270

Asp Leu Ser Asn Phe Pro Asp Tyr Pro Ala Phe Ala Asn Trp Ile Gly
            275             280             285

Asn Ile Leu Arg Asn Pro Glu Lys Ala Asp Glu Gln Ile Ala Lys Arg
    290             295             300

Ile Phe Thr Ala Leu Lys Thr Glu Thr Asp Tyr Ser Lys Lys Asn
305             310             315
```

```
<210> SEQ ID NO 22
<211> LENGTH: 312
<212> TYPE: PRT
<213> ORGANISM: Artificial Sequence
<220> FEATURE:
<223> OTHER INFORMATION: subject

<400> SEQUENCE: 22
```

```
Met Arg Glu Leu Val Val Lys Asp Asn Ala Leu Ile Asn Ala Ser Tyr
1               5               10              15

Asn Leu Asp Leu Val Glu Gln Arg Leu Ile Leu Leu Ala Ile Val Glu
            20              25              30

Ala Arg Glu Ser Gly Lys Gly Ile Asn Ala Asn Asp Pro Leu Val Val
            35              40              45

His Ala Glu Ser Tyr Ile Asn Gln Phe Asn Val His Arg Asn Thr Ala
    50              55              60

Tyr Gln Ala Leu Lys Asp Ala Cys His Asp Leu Phe Val Arg Gln Phe
65              70              75              80

Ser Tyr Gln Lys Val Asn Asp Arg Gly Asn Val Glu His Tyr Arg Ser
            85              90              95

Arg Trp Val Ser Glu Ile Gly Tyr Val Asp Asn Glu Ala Ile Val Lys
            100             105             110

Leu Ile Phe Ala Pro Ala Ile Val Pro Leu Ile Thr Arg Leu Glu Glu
            115             120             125
```

-continued

```
Gln Phe Thr Lys Tyr Glu Leu Gln Gln Val Ser Gln Leu Thr Ser Ala
    130                 135                 140

Tyr Ala Val Arg Leu Tyr Glu Leu Leu Ile Ala Trp Arg Ser Thr Gly
145                 150                 155                 160

Lys Thr Pro Val Ile Glu Leu Ala Asp Phe Arg Lys Arg Ile Gly Ile
                165                 170                 175

Leu Glu Thr Glu Tyr Lys Arg Met Glu Arg Phe Lys Thr Ser Val Leu
            180                 185                 190

Glu Leu Ala Ile Asn Gln Ile Asn Glu His Thr Asp Ile Asn Val Ala
            195                 200                 205

Tyr Glu Gln His Lys Lys Gly Arg Ser Ile Val Gly Phe Ser Phe Asn
    210                 215                 220

Phe Ser Gln Lys Glu Lys Lys Lys Ile Leu Glu Lys Ala Gln Val Ser
225                 230                 235                 240

Glu Gly Phe Lys Lys Leu Thr Glu Ala Gln Ile Thr Lys Tyr Ser Thr
                245                 250                 255

Val Leu Ser Lys Leu His Glu Leu Ser Asp Leu Ser Thr Phe Gln Asp
            260                 265                 270

Tyr Gln Ser Phe Ser Ile Trp Ile Gly Asn Ile Leu Arg Glu Pro Glu
    275                 280                 285

Ser Val Arg Phe Glu Thr Ala Glu Arg Ile Phe Ser Ser Leu Phe Lys
    290                 295                 300

Arg Thr Asp Phe Ala Ser Pro Asn
305                 310

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
ggattaatgc caatgatcc                                                19

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
ctttgcctgt ttctctcg                                                 18

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
gttctcgttt tcttggtaa                                                19

<210> SEQ ID NO 26
<211> LENGTH: 24
<212> TYPE: DNA
<213> ORGANISM: Artificial Sequence
<220> FEATURE:
<223> OTHER INFORMATION: primer
```

-continued

```
<400> SEQUENCE: 26
gaggacgaat taatattaca agtc                                                24

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ttaccaagaa aagcgagaac                                                     20

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
cgagagaaac aggcaaag                                                       18
```